(12) United States Patent
Leburton

(10) Patent No.: US 10,345,289 B2
(45) Date of Patent: Jul. 9, 2019

(54) METHOD AND APPARATUS FOR ANALYZING A TARGET MATERIAL

(71) Applicant: THE BOARD OF TRUSTEES OF THE UNIVERSITY OF ILLINOIS, Urbana, IL (US)

(72) Inventor: Jean-Pierre Leburton, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 372 days.

(21) Appl. No.: 15/063,095

(22) Filed: Mar. 7, 2016

(65) Prior Publication Data

US 2016/0187290 A1 Jun. 30, 2016

Related U.S. Application Data

(63) Continuation-in-part of application No. 14/781,106, filed on Sep. 29, 2015.
(Continued)

(51) Int. Cl.
*G01N 27/447* (2006.01)
*G01N 33/487* (2006.01)
*G01N 30/88* (2006.01)

(52) U.S. Cl.
CPC ..... *G01N 33/48721* (2013.01); *G01N 27/447* (2013.01); *G01N 27/4473* (2013.01); *G01N 2030/8827* (2013.01)

(58) Field of Classification Search
CPC ......... G01N 33/48721; G01N 27/4473; G01N 27/447; G01N 2030/8827
See application file for complete search history.

(56) References Cited

U.S. PATENT DOCUMENTS

| 8,713,607 B2 | 4/2014 | McEnroe et al. |
| 2004/0055875 A1* | 3/2004 | Siwy ..................... B01D 57/02 204/252 |

(Continued)

FOREIGN PATENT DOCUMENTS

| WO | 2012/138357 | 10/2012 |
| WO | 2013/016486 | 1/2013 |

OTHER PUBLICATIONS

A. Rycerz, et al. "Valley filter and valley valve in graphene", Nature Physics, vol. 3, p. 172-175, Mar. 2007.*
(Continued)

*Primary Examiner* — J. Christopher Ball
(74) *Attorney, Agent, or Firm* — Guntin & Gust, PLC; Mark Wilinski

(57) ABSTRACT

Aspects of the subject disclosure may include, for example, an apparatus having a material having a through-hole, a gate coupled to the material for controlling a charge concentration of the material, a sensor, and a controller coupled to the material, the gate and the sensor. The controller can perform operations including applying a first voltage potential to the material to induce a flow of current in the material, applying a second voltage potential to the gate to adjust the charge concentration of the material, and receiving sensing data from the sensor responsive to a change in electrical properties of the material caused by a target traversing the first through-hole of the material. The through-hole causes a plurality of structural portions of the target to be misaligned with a direction of the flow current in the material. Additional embodiments are disclosed.

20 Claims, 34 Drawing Sheets

Related U.S. Application Data

(60) Provisional application No. 61/813,220, filed on Apr. 18, 2013.

(56) References Cited

U.S. PATENT DOCUMENTS

| | | | |
|---|---|---|---|
| 2008/0187915 A1* | 8/2008 | Polonsky | B82Y 15/00 435/6.13 |
| 2010/0327847 A1* | 12/2010 | Leiber | B82Y 15/00 324/71.1 |
| 2014/0174927 A1 | 6/2014 | Bashir et al. | |
| 2014/0190833 A1 | 7/2014 | Lieber et al. | |
| 2015/0028846 A1* | 1/2015 | Zhu | G01N 27/3275 324/71.5 |

OTHER PUBLICATIONS

Branton, Daniel et al., "The potential and challenges of nanopore sequencing", Nature Biotechnology, 26(10), pp. 1146-1153, Oct. 2008.

Dekker, Cees, "Solid-state nanopores", Kavli Institute of Nanoscience, 2007.

Girdhar, A. et al., "Graphene quantum point contact transistor for DNA sensing", PNAS—Proceedings of the National Academy of Sciences, vol. 110, No. 42, Sep. 30, 2013, 16748-16753.

Gracheva, et al., "Simulation of the Electric Response of DNA Translocation Through a Semiconductor Nanopore-Capacitor", Nanotechnology, 2006, 622-633.

Humphrey, William et al., "VMD: Visual Molecular Dynamics", J. of Molecular Graphics, 1996, 33-38.

Li, Jiali et al., "DNA Molecules and Configurations in a Solid-State Nanopore Microscope", Nat. Mater, 2003, 611-615.

Mali, P. et al., "The dnaSET: a novel device for single-molecule DNA sequencing", IEEE Transactions on Electron Devices, vol. 51, No. 12, 2004.

Ozyilmaz, et al., "Electronic transport in locally gated graphene nanoconstrictions", Applied Physics Letters, vol. 91, No. 19, 2007.

Stampfer, C. et al., "Tunable graphene single electron transistor", NANO Letters, vol. 8, No. 8, 2008.

Storm, et al., "Fabrication of Solid-State nanopores with Single-Nanometre Precision", Nat. Mater., 2003, 537-540.

Postma, Henk W. , Rapid sequencing of individual DNA molecules in graphene nanogaps. Nano letters 10.2 (2010): 420-425.

Venkatesan, Bala M. et al., Stacked graphene-Al2O3 nanopore sensors for sensitive detection of DNA and DNA protein complexes. ACS nano 6.1 (2011): 441-450.

Branton, Daniel et al., "The Potential and Challenges of Nanopore Sequencing", Nature Biotechnology, vol. 26, No. 10, pp. 1146-1153, 2008, 8 pages.

Ozyilmaz, et al., "Electronic transport in locally gated graphene nanoconstrictions", Applied Physics Letters, vol. 91 pp. 192107-1 through 192107-3, 2007, 4 pages.

* cited by examiner

1400

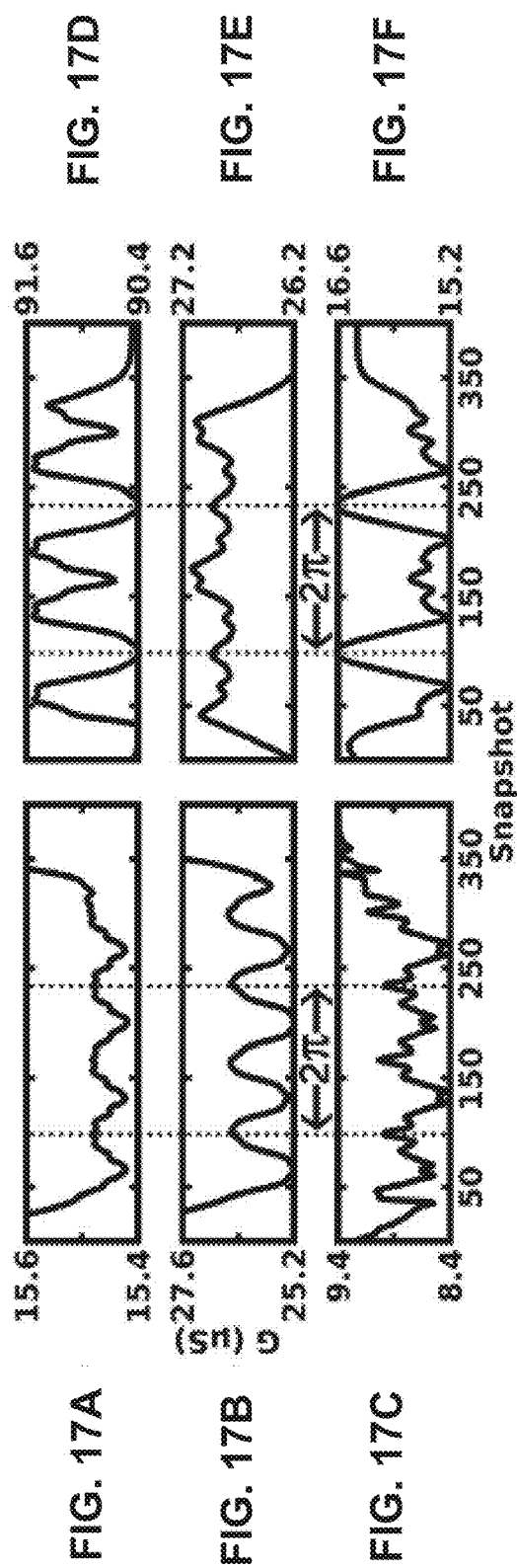

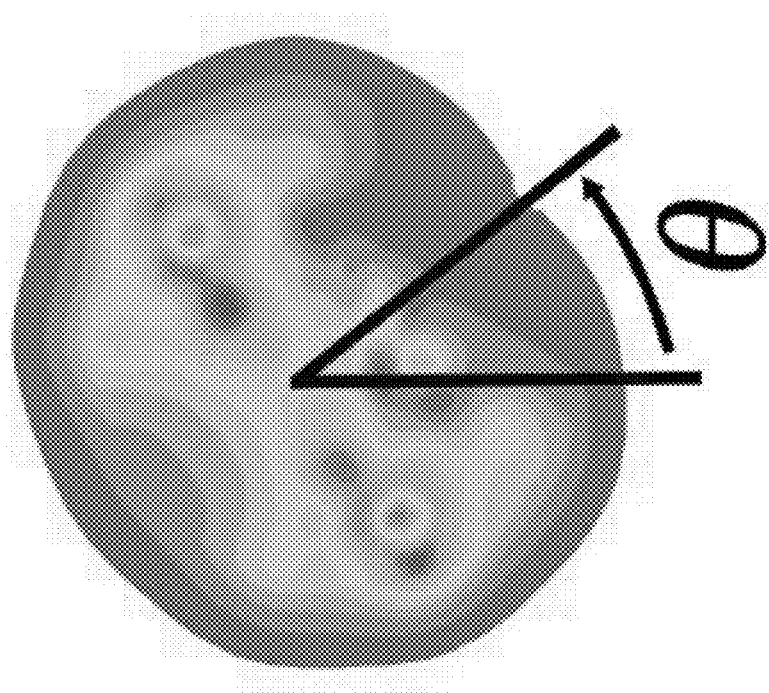

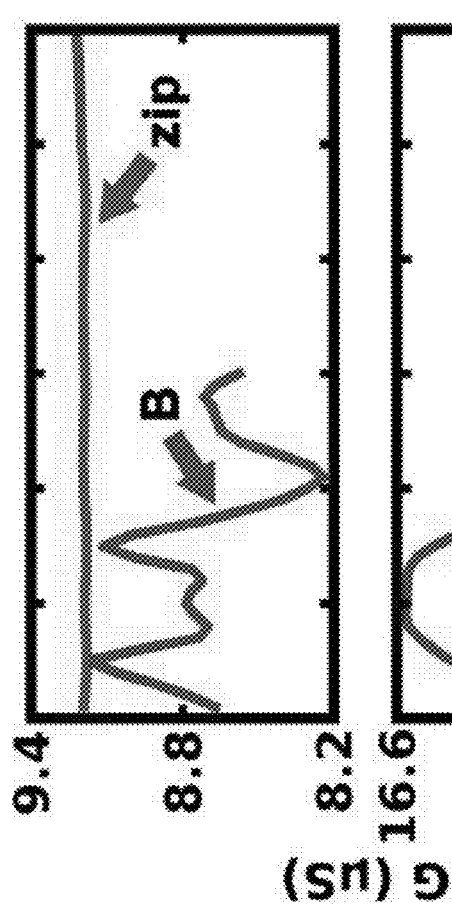
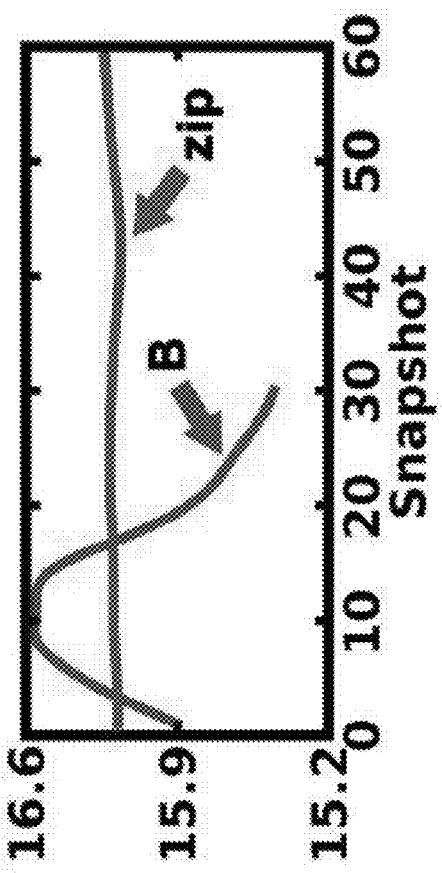

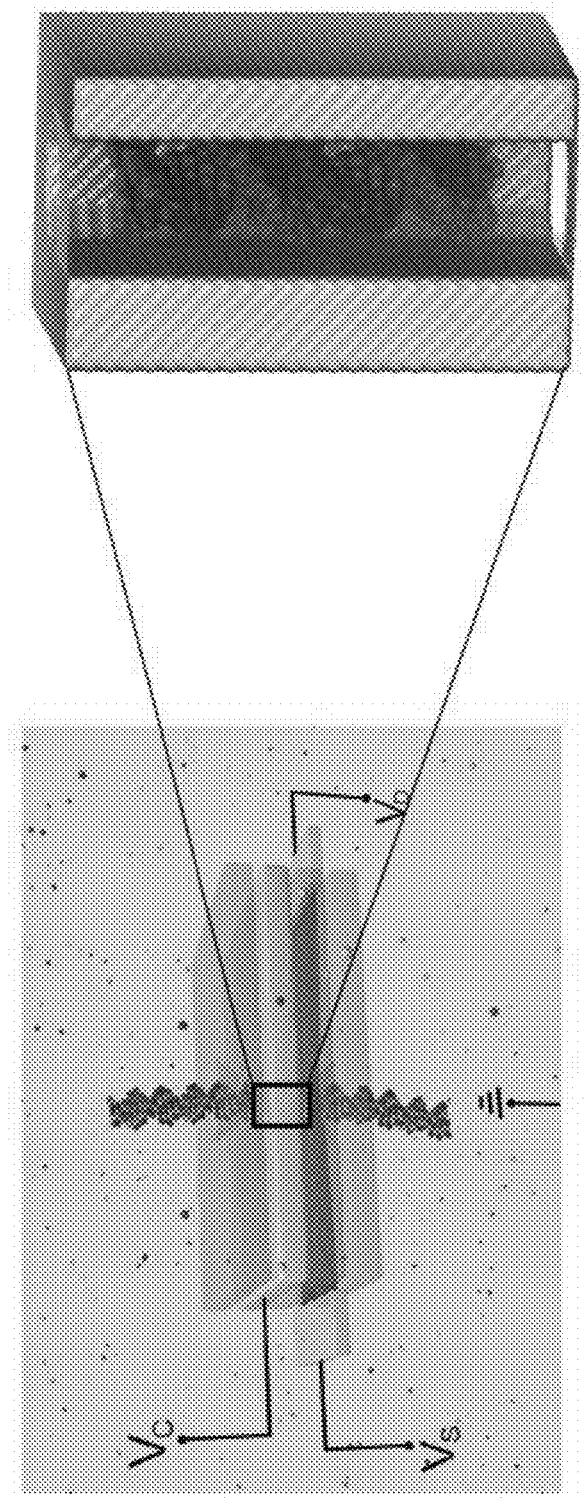

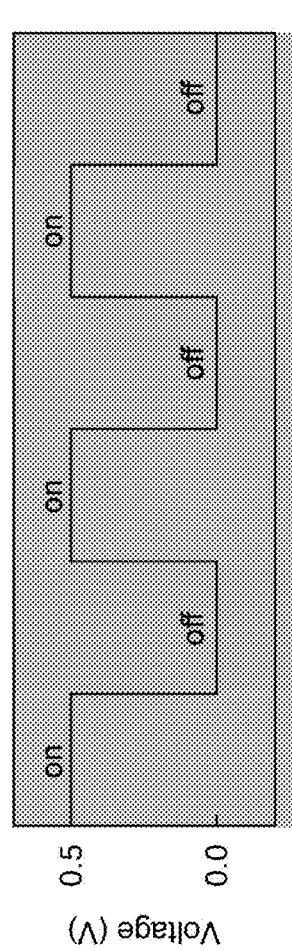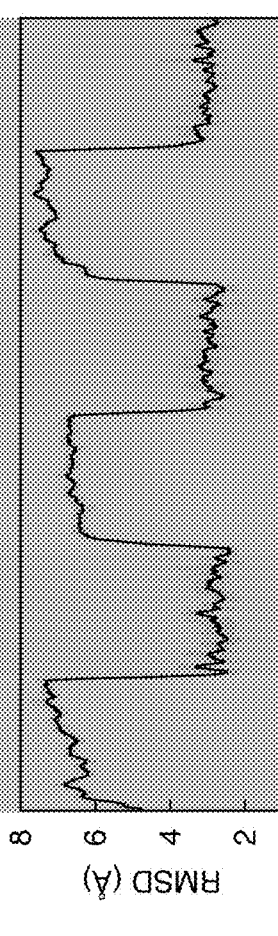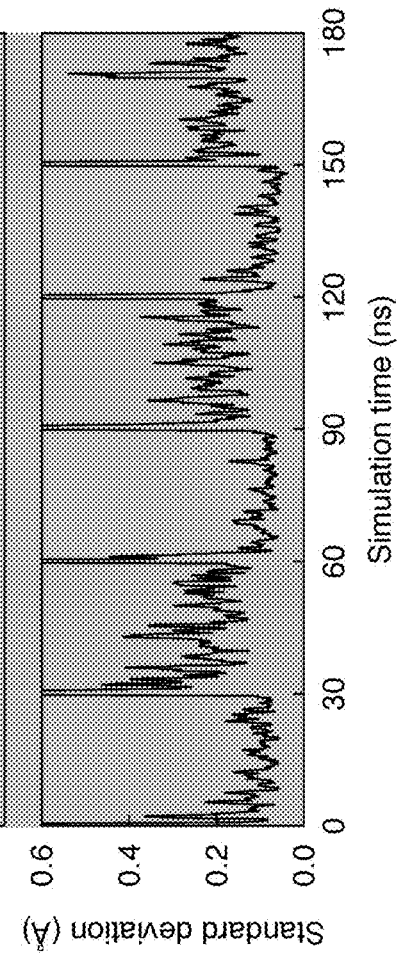
FIG. 24A
FIG. 24B
FIG. 24C

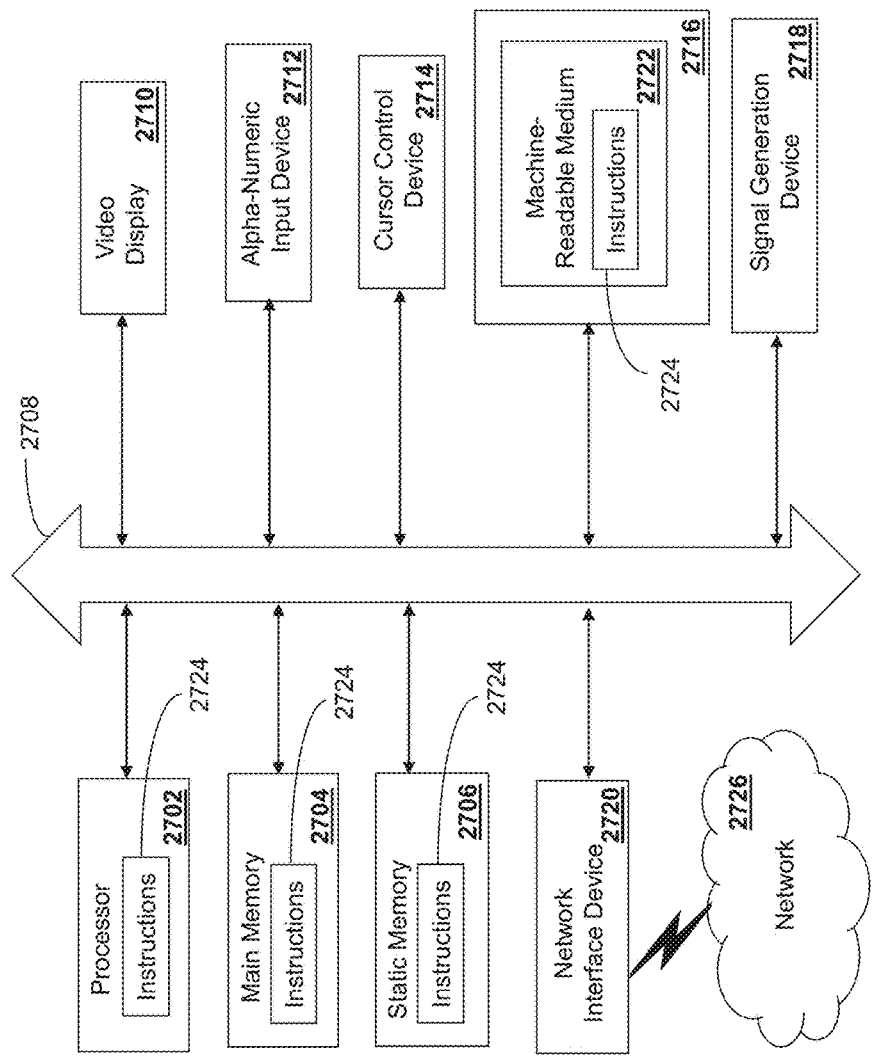

METHOD AND APPARATUS FOR ANALYZING A TARGET MATERIAL

PRIOR APPLICATIONS

The present application is a Continuation-in-Part of U.S. patent application Ser. No. 14/781,106, filed Oct. 4, 2013, which claims the benefit of priority to PCT Application Serial No. PCT/US13/63379, filed Oct. 4, 2013, which claims priority to U.S. Provisional Application No. 61/813,220 filed on Apr. 18, 2013, the disclosures of which are hereby incorporated by reference in their entirety.

FIELD OF THE DISCLOSURE

The subject disclosure relates generally to a method and apparatus for analyzing a target material.

BACKGROUND

Sequencing of biological materials such as, deoxyribonucleic acid, also known as DNA, is expected to become a vital means for diagnosing and in some instances predicting susceptibility to disease. The cost of instrumentation and the speed of sequencing by such instrumentation is an important driver for the availability of this technology to the general public Improvements and innovation of instrumentation of this kind is therefore desirable. It is also expected that such instruments can also be used for analyzing other forms of biological and non-biological materials.

BRIEF DESCRIPTION OF THE DRAWINGS

Reference will now be made to the accompanying drawings, which are not necessarily drawn to scale, and wherein:

FIGS. 17A, 17B, 17C, 17D, 17E, 17F, and 17G depict a conductance of g-QPCa for a) p=$p_1$, b) p=$p_2$, and c) n=$n_1$, and conductance of g-QPCb at d) p=$p_1$, e) p=$p_2$, and f) n=$n_1$ as a dsDNA helix is translocated through the nanopore. One full period of the helix rotation is shown between the dotted lines. g) Cross section of dsDNA potential in nanopore plane at rotational position θ;

FIGS. 18A, 18B and 18C depict a conductance of a) g-QPCa and b) g-QPCb at n=$n^+$ as a B-DNA (red) and a zip-DNA (green) is translocated through the nanopore. c) The initial (B-DNA) and final (zip-DNA) conformation of the morphological transformation;

FIGS. 21A, 21B, 21C and 21D depict (a) Schematic of a prototypical multilayer transistor with a nanopore for DNA manipulation and detection. A metallic control layer (yellow), sandwiched between two insulating oxide layers (blue), is biased at a voltage $V_C$. A conducting sensing membrane such as a graphene monolayer, biased at $V_D$ and $V_S$, is used to detect the motion of the passing DNA molecule. The system is biased with respect to a common ground. (b) System of molecular dynamics simulations in this study. The system consists of a dsDNA confined within a nanopore in a metallic membrane. To render the DNA molecule visible, the front part of the membrane is left transparent. (c,d) Electrostatic potential (c) and magnitude of electric field (d), in the xy cross-section plane (top panel) and along a line across nanopore diameter (bottom panel), of a 0.5 V biased cylindrical nanopore. Arrows denote the directions of local electric fields.

FIGS. 24A, 24B and 24C depict controllable stabilization of dsDNA by a pulsed voltage of 0.5 V. (a-c) Voltage applied to the electrode (a), calculated RMSD from the starting configuration (b) and the associated standard deviation (c) versus simulation time;

FIG. 27 depicts an illustrative diagrammatic representation of a machine in the form of a computer system within which a set of instructions, when executed, may cause the machine to perform any one or more of the methodologies disclosed herein.

DETAILED DESCRIPTION

Figure 1:
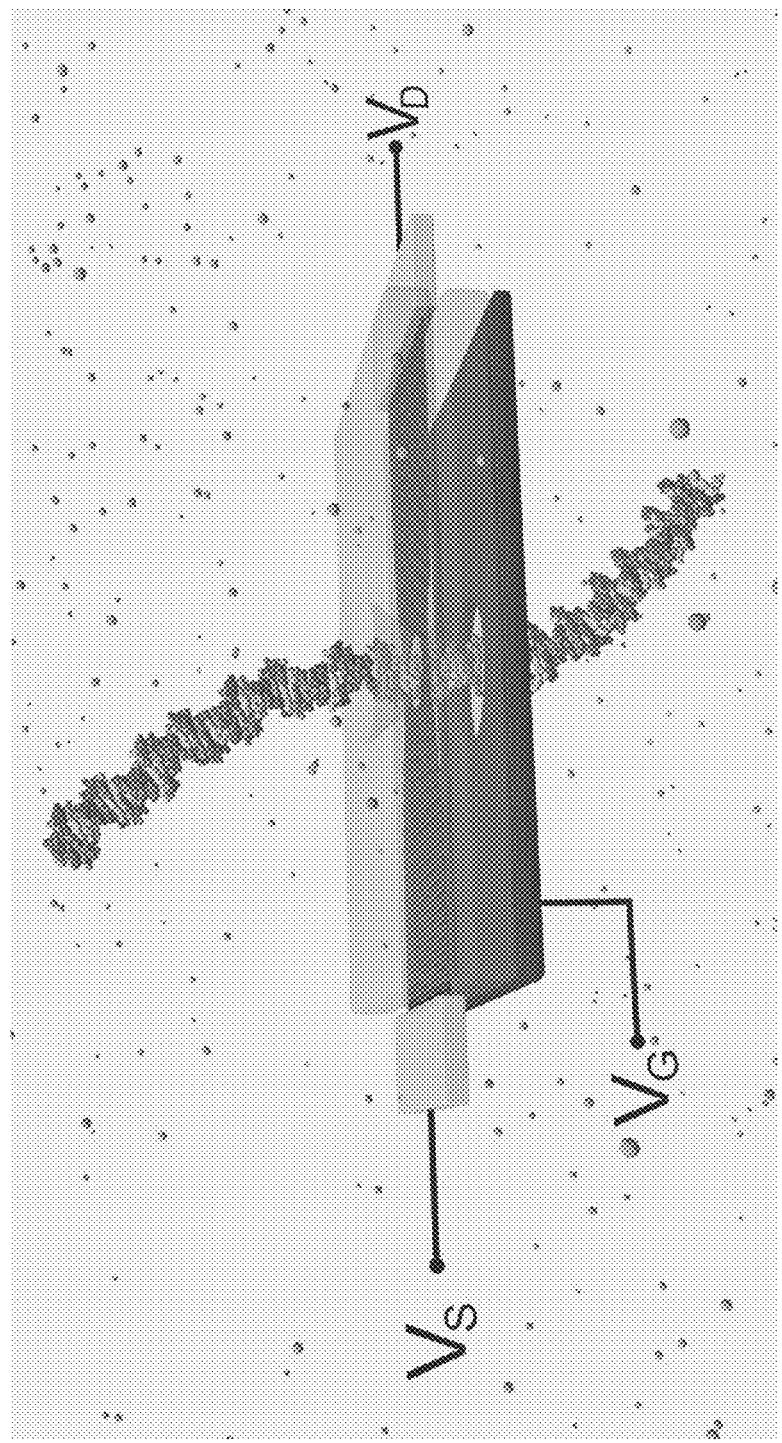
FIG. 1: Schematic diagram of a prototypical solid-state, multilayer device containing a GNR layer (black) with a nanopore, sandwiched between two oxides (transparent) atop a heavily doped Si back-gate, $V_G$ (green). The DNA is translocated through the pore, and the current is measured with the source and drain leads, $V_S$ and $V_D$ (gold). (See FIG. 12 for a cross-sectional schematic diagram)

One embodiment of the subject disclosure entails a method for coupling a first end of a material to a first electrode; coupling a second end of the material to a second electrode; coupling a gate to the material; forming in the material a first through-hole having a non-circular structure; forming in the gate a second through-hole; introducing a target material at one of the first through-hole or the second through-hole to analyze the target material; applying a first voltage potential to the first electrode and the second electrode coupled to the material; applying a second voltage potential to the gate to adjust a charge concentration of the material; and measuring a change in electrical properties of the material responsive to the target material traversing the first through-hole of the material.

One embodiment of the subject disclosure entails an apparatus having a material; and a gate coupled to the material for controlling charge concentration of the material. The material includes a first through-hole comprising an irregular structure, and a first port and a second port for conduction of charges in the material. The gate includes a second through-hole that is at least partially aligned with the first through-hole. A first voltage potential applied to the first port and the second port, and a second voltage potential applied to the gate adjusts a charge concentration of the material. A sensor can be used to measure a change in electrical properties of the material caused by a target material traversing the first through-hole of the material.

One embodiment of the subject disclosure entails an apparatus having a material having a first through-hole, a gate coupled to the material for controlling a charge concentration of the material, the gate including a second through-hole. The apparatus can further include a sensor, and a controller coupled to the material, the gate and the sensor. The controller can perform operations including applying a first voltage potential to the material to induce a flow of current in the material, applying a second voltage potential to the gate to adjust the charge concentration of the material, and receiving sensing data from the sensor responsive to a change in electrical properties of the material caused by a target traversing the first through-hole of the material. The first through-hole causes a plurality of structural portions of the target to be misaligned with a direction of the flow current in the material.

One embodiment of the subject disclosure entails a method for providing a material having one or more atomic layers with two or less degrees of freedom for motion of charges in the material, constricting the material to generate a constriction in the material to configure electrical properties in the material, coupling a first end of the material to a first electrode, coupling a second end of the material to a second electrode, coupling a gate to the material, providing a first through-hole in the material near a vicinity of the constriction, providing a second through-hole in the gate, wherein the first through-hole and the second through-hole are substantially coaxially aligned, introducing a target material at one of the first through-hole or the second through-hole to analyze the target material, applying a first voltage potential to the first electrode and the second electrode to the material, applying a second voltage potential to the gate to adjust a charge concentration of the material, and measuring a change in electrical properties of the material responsive to the target material traversing the first through-hole of the material.

One embodiment of the subject disclosure entails an apparatus including a material having one or more atomic layers with two or less degrees of freedom for motion of charges in the material, and a gate coupled to the material for controlling charge concentration of the material. The material can have constricted sides, a first through-hole, and a first port and a second port for conduction of charges in the material. The gate can have a second through-hole that is at least partially aligned with the first through-hole. A first voltage potential can be applied to the first port and the second port, along with a second voltage potential applied to the gate which adjusts the charge concentration of the material. A sensor can be used to measure a change in electrical properties of the material caused by a target material traversing the first through-hole of the material.

One embodiment of the subject disclosure entails an apparatus including a material having one or more atomic layers with two or less degrees of freedom for motion of charges in the material, wherein the material comprises constricted sides and a first through-hole, a gate coupled to the material for controlling charge concentration of the material, wherein the gate comprises a second through-hole, a sensor, and a controller coupled to the material, the gate and the sensor. The controller can perform operations comprising applying a first voltage potential to the material, applying a second voltage potential to the gate to adjust a charge concentration of the material, and receiving sensing data from the sensor responsive to a change in electrical properties of the material caused by a target traversing the first through-hole of the material.

Over the past few years the need has grown for low-cost, high-speed, and accurate biomolecule sensing, propelling the so-called third generation of genome sequencing devices. Many associated technologies have been developed, but recent advances in the fabrication of solid-state nanopores have shown that the translocation of biomolecules such as DNA through such pores is a promising alternative to traditional sensing methods. Some of these methods include measuring (1) ionic blockade current fluctuations through nanopores in the presence of nucleotides, (2) tunneling-currents across nanopores containing biomolecules, and (3) direct transverse-current measurements. Graphene is a candidate for such measurements. Studies suggest that functionalized graphene nanopores can be used to differentiate passing ions, demonstrating the potential use of graphene membranes in nanofluidics and molecular sensing. In addition, its atomic-scale thickness allows a molecule passing through it to be scanned at the highest possible resolution, and the feasibility of using graphene nanopores for DNA detection has been demonstrated experimentally. Lastly, electrically-active graphene can, in principle, both control and probe translocating molecules, acting as a gate as well as a charge sensor which passive, oxide-based nanopore devices are incapable of doing.

Molecular dynamics studies describing the electrophoresis of DNA translocation through graphene nanopores demonstrated that DNA sequencing by measuring ionic current blockades is possible in principle. Additionally, several groups have reported first-principles-based studies to identify base-pairs using tunneling currents or transverse conductance-based approaches. Saha et al. (see Saha K, Drndić M, Nikolić B (2011) DNA base-specific modulation of microampere transverse edge currents through a metallic graphene nanoribbon with a nanopore. Nano Lett 12(1):50-55) reported transverse edge current variations of the order of 1 µA through graphene nanoribbons (GNR) caused by the presence of isolated nucleotides in a nanopore and reported base-pair specific edge currents. These studies, however, do not account for solvent or screening effects; the latter effects are due to the presence of ions in the solution and can reduce the ability of the nanoribbon to discern individual nucleotides. Very recently, Avdoshenko et al. (see Avdoshenko S, Nozaki D, Gomes da Rocha C, Gonzalez J, Lee M et al. (2013) Dynamic and electronic transport properties of DNA translocation through graphene nanopores. Nano Lett 13(5): 196949'76) investigated the influence of single-stranded DNA on sheet currents in GNRs with nanopores. However, their study does not consider the carrier concentration modulation of the current, the influence of the GNR-edge boundary-condition on the nanopore sensitivity, or a self-consistent treatment of screening due to charged ions in solution.

GNRs are strips of graphene with a finite width that quantizes the energy states of the conduction electrons. Unlike traditional quantum wells, the boundary conditions of GNRs are complicated functions of position and momentum resulting from the dual sublattice symmetry of graphene, giving rise to a unique band structure. Because of this, the shape of the boundary as well as the presence of nanopores profoundly affects the electronic states of GNRs, for example, leading to a difference in band structure for zigzag and armchair-edged GNRs.

The edge of a GNR can be patterned with near-atomic precision, opening up the possibility to investigate different geometries. In the case of complicated edge shapes, the current displays an extremely nonlinear and not strictly increasing dependence on carrier concentration. The graphene Quantum Point Contact (g-QPC) is an example in this regard, as its irregular edge yields a complex band structure and rich conductance spectrum with many regions of high sensitivity and negative differential transconductance (NDTC) as shown below. In addition, the g-QPC electronic properties are not limited by stringent GNR uniformity (armchair or zigzag) in the boundary conditions. Moreover, the carrier concentration itself, which can be controlled by the presence of a back-gate embedded within a g-QPC device, can affect the sensitivity and nonlinearity of the current. As a result, changes in external electric fields, including changes due to rotation and translation of external molecular charges, alter the local carrier concentration and can influence the g-QPC conductance.

The subject disclosure demonstrates complex and nonlinear effects of altering boundary shapes, graphene carrier concentrations, and electric potentials due to DNA translocation on the conductance of such a device. The subject disclosure presents illustrative embodiments for sensing DNA by performing transport measurements in a g-QPC device and demonstrating that the sensitivity of the conductance can be geometrically and electronically tuned to detect small differences in the charge geometry of biomolecules such as DNA.

FIG. 1 shows a monolayer g-QPC device in an ionic water solution, containing a single layer of patterned graphene connected to source and drain leads and sandwiched between two oxide layers to isolate the graphene from the aqueous environment. The graphene and oxide layers have coaxial nanopores ranging from 2 to 4 nm, allowing charges, molecules, or polymers to pass through. An aspect of the device shown is a back gate underneath the lower oxide substrate made of a metal or heavily-doped semiconductor or another graphene layer to control the charge carrier concentration in graphene (the gate layer could in practice be capped by an oxide layer to avoid unwanted electrochemistry); the back-gate enhances its electrical sensitivity to DNA translocation. The diameter of the nanopore is small enough to attain the required sensitivity, but is wide enough to let the biomolecules translocate.

Figure 2:
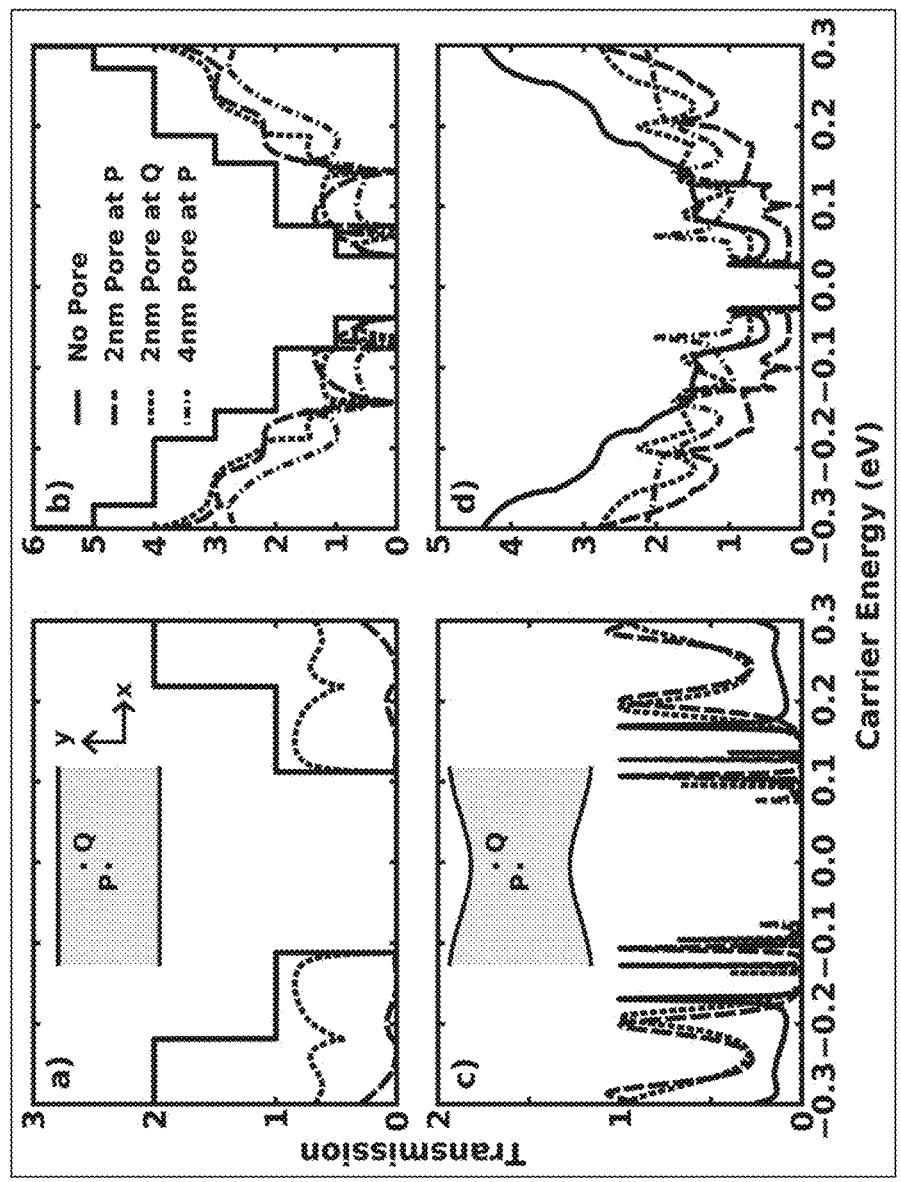
FIG. 2: Transmission functions for various edge geometries and pore configurations: a) 5 nm (5-GNR) and b) 15 nm (15-GNR) wide GNR-edged devices, c) 8 nm (8-QPC) and d) 23 nm (23-QPC) wide QPC-edged devices. Pristine (solid), a 2 nm pore at point P (long dash), a 2 nm pore at point Q (short dash), and a 4 nm pore at point P (dot dash)

The subject disclosure presents four edge geometries, namely a 5 nm wide (FIG. 2a) and a 15 nm wide (FIG. 2b) pure armchair-edge GNR (FIG. 2a inset) as well as an 8 nm wide (FIG. 2c) and a 23 nm wide (FIG. 2d) QPC edge (FIG. 2c inset). These geometries will herein be referred to as 5-GNR, 15-GNR, 8-QPC, and 23-QPC. The QPC geometries have pinch widths of 5 nm and 15 nm (⅔ total width), the same as the widths of the armchair-edged GNRs. For each edge geometry, four pore configurations are considered: pristine (no pore), a 2 nm pore in the center (point P in FIG. 2), a 2 nm pore centered at 75% of the total (pinch) width for the GNR (QPC) (point Q in FIG. 2), and a 4 nm pore at the center (point P in FIG. 2).

FIG. 2 demonstrates the effects of the different edge geometries and pore configurations previously described on the transmission spectra for suspended graphene nanoribbons in vacuum. A Fermi energy range is chosen from 0 to or smaller than 0.5 eV, which corresponds to carrier concentrations varying from ~$10^{11}$ cm$^{-2}$ to 5-7×$10^{12}$ cm$^{-2}$ at a temperature of 300 K, easily achievable in a conventional g-FET. The transmission for the pristine (no pore) 5-GNR edge exhibits the classic staircase shape resulting from the armchair-edge boundary conditions (FIG. 2a). The presence of a nanopore introduces a scatterer in the GNR, which manifests itself as additional boundary conditions at the pore edge, restricting the transmission in two ways: first, the number of allowed electronic states becomes reduced due to the need of satisfying more stringent boundary conditions; second, the electronic states that do satisfy these boundary conditions generally have smaller probability currents due to scattering off the nanopore. The resulting transmission probability varies largely within narrow carrier energy ranges and exhibits resonances at particular carrier energies, revealing the strong dependence of transmission probability on carrier energy. Increasing the pore diameter enhances the scattering nature of the nanopore, thereby reducing the transmission probability, as can be seen in FIG. 2a, where the 5-GNR with a 4 nm pore has an almost negligible transmission probability for most carrier energies in the represented range. By changing the nanopore positions, the particular wavelengths of the electronic states that satisfy the boundary conditions vary, which further affects the transmission probability. For instance, the transmission of the GNR with the pore at Q is higher at lower energies compared to the GNR with the pore at P, since the allowed electronic states at these lower energies have larger wavelengths.

Similar trends can be seen for the transmission probability determined for the 15-GNR (FIG. 2b). Because of the larger width compared to that of 5-GNR, there are significantly more electronic states within a particular carrier energy range, increasing the transmission probability for all pore configurations. This results in more closely-spaced transmission steps in the pristine GNR. As for 5-GNR with and without pore, pore edge boundary conditions destroy the stair-case behavior of the transmission seen for pristine 15-GNR as well as reduce the magnitude of the transmission probability. In contrast, because of the larger width, the density of allowed electronic states in the 15-GNR is larger at high energies compared to the respective density in the 5-GNR. As a result, both pore configurations P and Q in the 15-GNR have a similar number of allowed electronic states within a specific energy range, minimizing the difference in transmission between the two configurations at higher carrier energies.

FIG. 2c shows the transmission probability for the 8-QPC which exhibits strong variations as compared to that in the 5 or 15-GNR, because the non-uniform QPC edge introduces more stringent boundary conditions on the electronic states, especially when the QPC contains a nanopore. The transmission probability curves for the pristine 8-QPC and for the 8-QPC with a pore exhibit many resonance peaks throughout the Fermi energy range. It can be seen that the 4 nm pore (green curve) exhibits negligible transmission probability over the whole Fermi energy range, except around the band gap, which is reflected in two resonance peaks in both the conduction and valence bands. Increasing the width in going from the 8- to 23-QPC increases the density of states within an energy range, smoothing out the transmission at higher carrier energies as in the case of the 15-GNR (FIG. 2d). The influence of the position and size of the nanopore on the transmission function follows the same trend as with the 15-GNR at high carrier energies as mentioned above.

Figure 3:
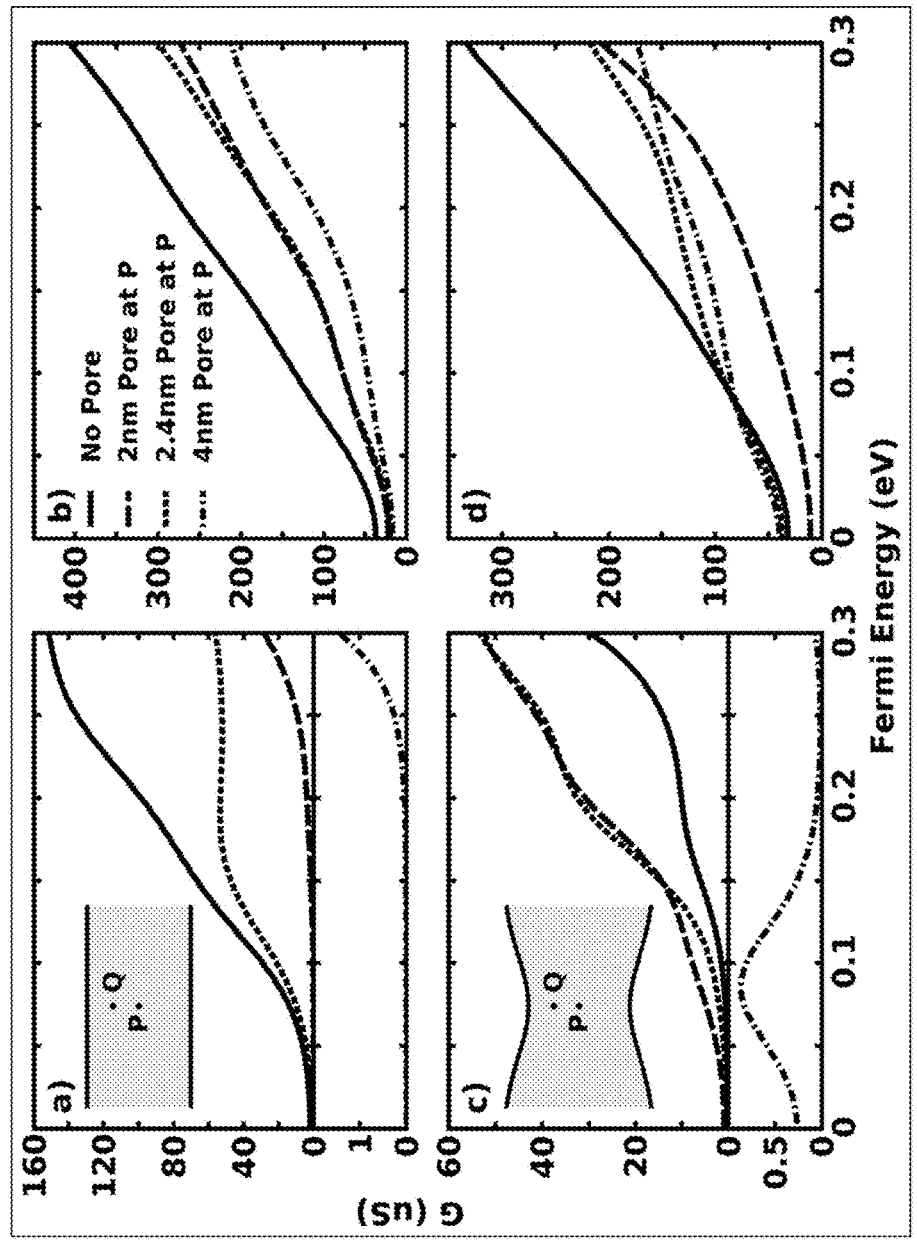
FIG. 3: Conductance versus Fermi energy (as a function of carrier concentration) for the four edge geometries with four pore configurations for each geometry. a) 5-GNR, b) 15-GNR, c) 8-QPC and d) 23-QPC. Pristine (solid), 2 nm pore at point P (long dash), 2 nm pore at point Q (short dash), and 4 nm pore at point P (dot dash)

The electronic conductance as a function of the Fermi energy of charge carriers is shown in FIG. 3. The conductance at a particular Fermi energy is the average of the transmission probability around that carrier energy weighted by the Fermi-Dirac distribution as described in equation (4). FIG. 3a demonstrates that the conductance of the 5-GNR as a function of carrier energy is strongly dependent on nanopore size and position. As expected, the pristine 5-GNR has the largest conductance and increases relatively monotonically over a wide range of carrier energies. Compared to the pristine 5-GNR, the conductance curve of the 2 nm pore at P is much lower over the range of Fermi energies up to 0.3 eV, while the curve with the pore at Q is at least one order of magnitude higher, exhibiting a plateau beyond 0.15 eV. The 4 nm pore in the 5-GNR displays the lowest conductance values compared to all other 5-GNRs (pristine, 2 nm hole at P, 2 nm hole at Q) because of its suppressed transmission probability as discussed earlier (FIG. 2). FIG. 3b shows the conductance curves for the 15-GNR geometries. All four systems (15-GNR: pristine, 2 nm hole at P, 2 nm hole at Q, 4 nm hole at P) show a relatively monotonic increase in conductance with Fermi energy. All conductance curves achieve values about three times larger than seen for the 5-GNR, exhibiting the expected scaling with GNR width. The positional effects are mitigated as the 2 nm Q and P curves are almost identical. However, the pore size effects are retained, illustrated by a decrease in the conductance with increased (4 nm) pore size.

FIG. 3c shows the conductance properties of the 8-QPC systems. The conductance changes at varying rates throughout a range of Fermi energies. The introduction of a 2 nm pore at either P or Q enhances the magnitude of the conductance dramatically compared to that of the pristine 8-QPC, contradicting an intuitive notion that the pore acts as a scattering barrier. This behavior can be attributed to the rich interaction of the electronic states with the edge and pore boundaries as seen in FIG. 2c. Also, detected is the appearance of a NDTC region in the conductance in the case of the 8-QPC with a 4 nm hole, a feature unobserved for the GNR systems. Apparently, tailoring the pore properties within a QPC geometry can result in large changes in the conductance behavior.

FIG. 3d shows the conductance properties of the four 15-QPC systems investigated. Comparison with the 8-QPC results shows that the increased width renders the conductance less sensitive to pore geometry; in particular, NDTC regions are not recognized in the 15-QPC with a 4 nm pore. However, conductance values at Fermi energies above 0.15 eV differ greatly for different pore sizes. Paradoxically, it is observed that the conductance at low Fermi energies of the 15-QPC with a 4 nm pore is larger than in the case of the 15-QPC with a 2 nm pore at P. This behavior is due to enhanced transmission probability at low Fermi energies, caused by the particular shape of 4 nm nanopore.

Most of the conductance curves in the four panels of FIG. 3 exhibit different regions of high and low "sensitivity," which the subject disclosure defines as the slope of the conductance with Fermi energy. As a result, small changes in the Fermi energy can result in large variations in conductance similar to the transconductance in a field-effect transistor (FET).[33] Because the local carrier potential energy will be influenced by a nearby charge, which can translate into Fermi energy changes, deviations in such a charge's position can significantly modify the device conductance. This behavior can be exploited to build an ultra-sensitive charge sensing device.

Figure 4:
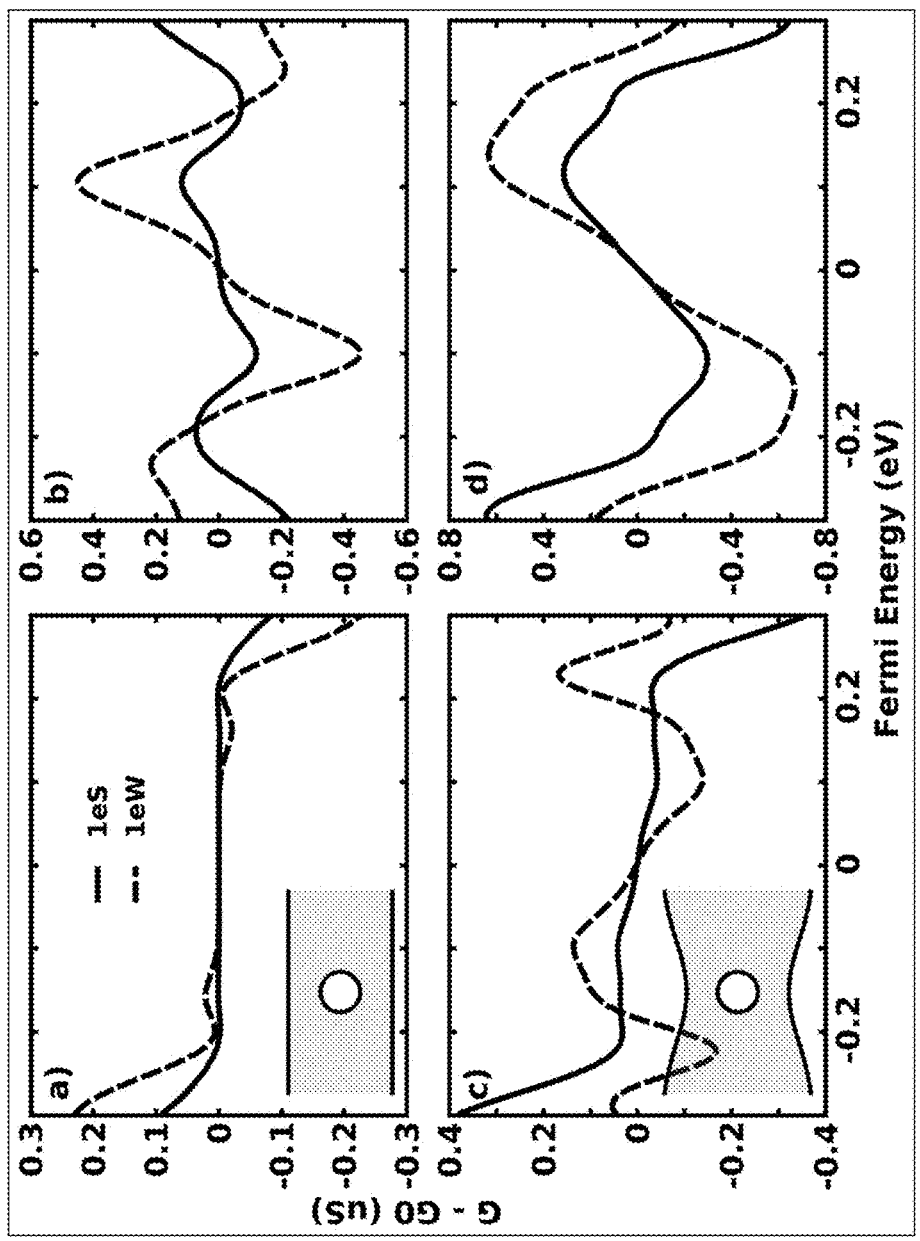
FIG. 4: Change in the conductance due to adding an external charge within the 2 nm pore. 'S' means the charge is placed one half radius south of the center of the pore, and 'W' means the charge is placed one half radius west of the center of the pore. a) 5-GNR, b) 15-GNR, c) 8-QPC and d) 23-QPC.

The influence of a solvent is treated as a mean-field approximation based on Boltzmann-statistics in the electrolyte to determine the on-site potentials on graphene as described in the methods section. Electrochemical interactions are ignored between graphene and solution, since in practice the graphene will be capped by an insulator, preventing, for the most part, direct interaction between graphene and the solvent. The effect of a test charge, placed within a pore, on electronic transport in graphene is illustrated in FIG. 4. Shown are the conductance changes upon placing a single electron charge (e) at two positions within a 2 nm pore at P; one position is at ½ radius to the west of the pore center (W or west) and the other at ½ radius south of the pore center (S or south). FIGS. 4a and 4b display the conductance response for the 5-GNR and 15-GNR respectively, while FIGS. 4c and 4d display conductance responses for the 8-QPC and 23-QPC, respectively. The difference in conductance upon charge placement varies between 0 and 0.8 μS for all geometries, which is well within the sensing range of most current probes. Conductance change for the 5-GNR (FIG. 4a) are negligible over most of the energy range for both angular charge (W & S) positions, due to the suppressed transmission probability at low carrier energies (blue curve of FIG. 2a); for the 15-GNR, 8-QPC, and 23-QPC cases (FIGS. 4b, 4c, and 4d) the angular position of the charge within the pore has a significant effect on the conductance, causing not only large differences in conductance over the investigated energy range but also a different sensitivity of the conductance to the Fermi energy. In these cases, the maximum difference in conductance occurs for a test charge in the west (south) position at smaller (larger) Fermi energies. The conductance can be either enhanced or reduced by the test charge, depending on the value of the Fermi energy. In the case of the 15-GNR (FIG. 4b), for example, when the Fermi energy lies between 0 and 0.18 eV, the conductance change for the electron test charge in the west position is positive, while the change is negative for Fermi energies above this range. Similar behavior is seen for the 8-QPC and 23-QPC, but over different Fermi energy ranges (FIGS. 4c and 4d).

It is observed that in FIG. 4, for all cases, the differences in conductance are anti-symmetric with respect to the Fermi energy. This is a direct consequence of the symmetry between electrons and holes in graphene. Because of this symmetry, electrons and holes tend to react to the same potential with opposite sign, such that the conductance changes are an odd function of Fermi energy. For instance, in FIG. 4b, there is a peak in the conductance change for the 15-GNR around 0.1 eV for all four charge configurations; a similarly shaped peak, but with opposite sign, is located at −0.1 eV. Similarly, one finds for the 23-QPC, as shown in FIG. 4d, peaks at 0.15 eV and opposite peaks at −0.15 eV. The different parity between the differential conductance curves at low energy in FIGS. 4c and 4d can be observed, which are negative for the 8-QPC (FIG. 4c) and positive for the 23-QPC (FIG. 4d). Similar conductance curves for a reduced electron charge are described below that display the same behavior as the full electron test charge but scaled by a constant factor as expected.

Figure 5:
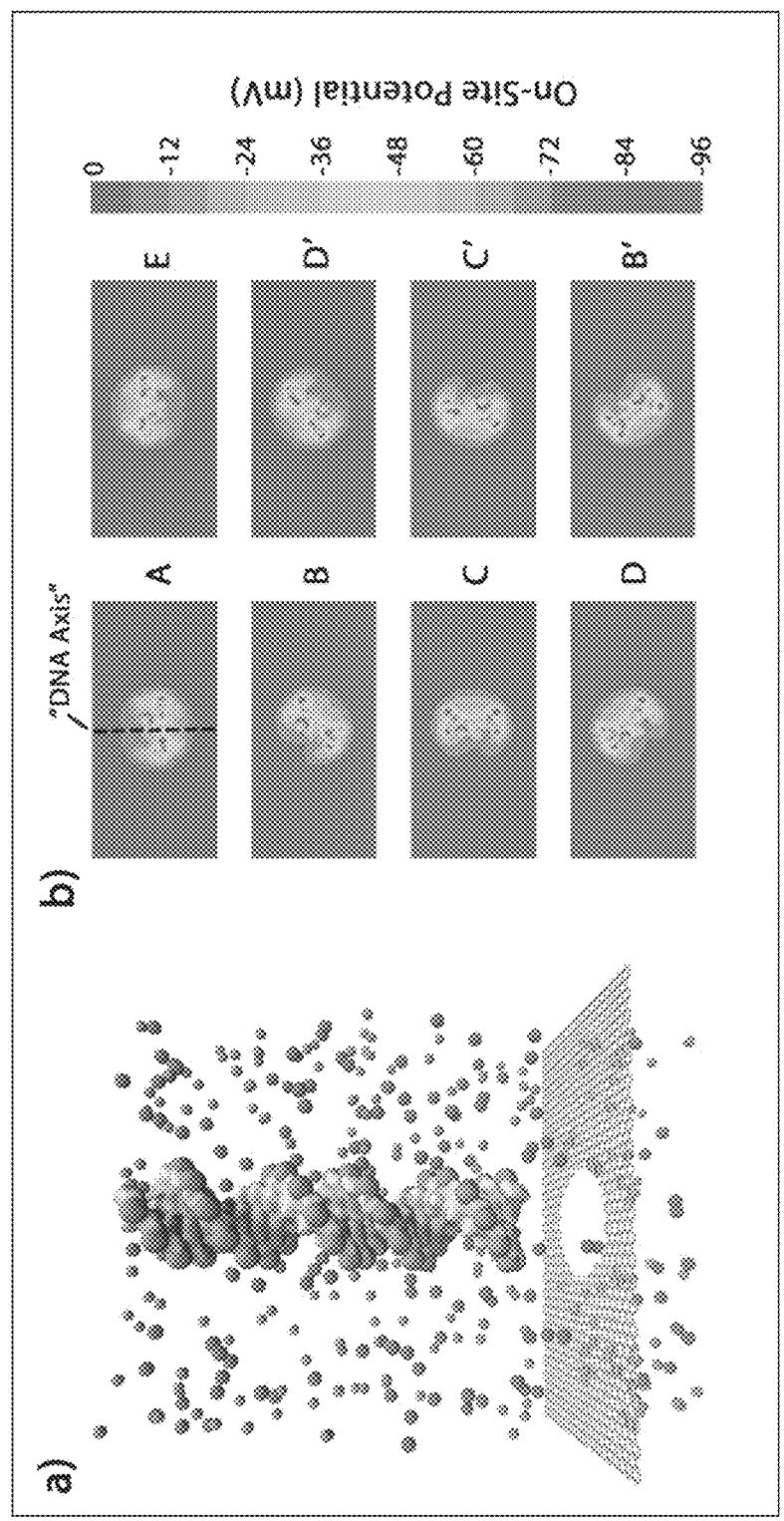
FIG. 5: a) Schematic of an AT DNA strand translocating through a pore. b) Potential maps in the graphene plane due to the DNA molecule at eight successive snapshots throughout one full rotation of the DNA strand.

In order to demonstrate a potential application of a charge-sensing device exploiting the sensitivity of geometrically-tuned GNRs, the translocation of a strand of DNA through a 2.4 nm pore located at the center (point P above) of the four edge geometries is simulated. A 24 base-pair B-type double-stranded DNA segment consisting of only AT nucleotide base-pairs is translocated. The DNA is initially placed such that the bottom of the strand is 3.5 Å above the graphene membrane, and the axis of the DNA passes through the center of the nanopore (FIG. 5a). The DNA is then rigidly translocated through the nanopore at a rate of 0.25 Å per time step (snapshot) until the DNA has passed through the pore completely. After the last (400th) snapshot the top of the DNA strand is 13.5 Å below the graphene membrane. The charge distribution from the DNA at each time step (snapshot) is mapped into the Poisson solver, and the electric potential on the graphene membrane is calculated for each snapshot as the DNA rigidly translocates through the pore.

Due to strong screening from ions and water near the graphene membrane, the on-site electric potential of the nanopore is dominated by charges contained within a slice coplanar with the graphene membrane and directly inside the nanopore. Hence, during the translocation of the biomolecule through the nanopore, the graphene membrane will sense a succession of DNA slices, which appear as an in-place rotation of the double helix in the absence of translocation. Since it is only the charges in the pore that matter (due to the strong screening effects), the electric potentials around the pore due to the DNA being pulled through are virtually identical to the potential arising if the DNA slice coplanar with the membrane was rotated without translocation. FIG. 5b shows the on-site potentials for eight successive positions of the DNA (A-B-C-D-E-D'-C'-B') in the graphene plane, representing one half cycle of this pseudo-rotational behavior.

As mentioned above, the lattice including a nanopore may not be both x-axis and y-axis reflection symmetric with the pore at the center due to the discrete nature of the lattice. For example, the 15-GNR with a 2.4 nm pore exhibits y-axis (FIG. 2a inset) reflection symmetry, but not x-axis (FIG. 2a inset) reflection symmetry, as in the shape of the letter "Y." In contrast, the 5-GNR, 8-QPC, and 23-QPC geometries with a 2.4 nm pore exhibit both y-axis and x-axis reflection symmetry, as in the shape of the letter "X." These symmetries have an effect on the electronic conductance in GNRs when the DNA strand is introduced. When calculating the conductance from the transmission probability, it is important to note that the transmission probability itself does not represent a particular direction of current flow. In other words, a reflection about either the x- or y-axis of the lattice and its on-site electric potential map leaves the transmission probability, and hence the conductance, unchanged. When the DNA strand is translocated, the electric potential maps of successive snapshots look like A->B->C->D in FIG. 5b corresponding to the translocation of one half pitch of the DNA helix, and for the second half of the cycle the successive snapshots look like E->D'->C'->B'. The D', C', and B' potential maps are effectively the mirror images (y-axis reflected) of D, C, and B, respectively. As a result, assuming the DNA potential is reflection symmetric about its own axis ("DNA axis"), the conductance curves corresponding to geometries with only y-axis reflection symmetry should display a half-cycle "mirror" effect, repeating only after a full A->E->A rotation, i.e. the conductance should be identical for snapshots D and D', C and C', etc. On the other hand, because the electric potential maps B and D (and therefore B' and D') are identical after an x-axis reflection, the conductance should mirror after a quarter-cycle translation of the DNA and should repeat itself after a half-cycle (A->B->C->D) in the 5-GNR, 8-QPC, and 23-QPC.

Figure 6:
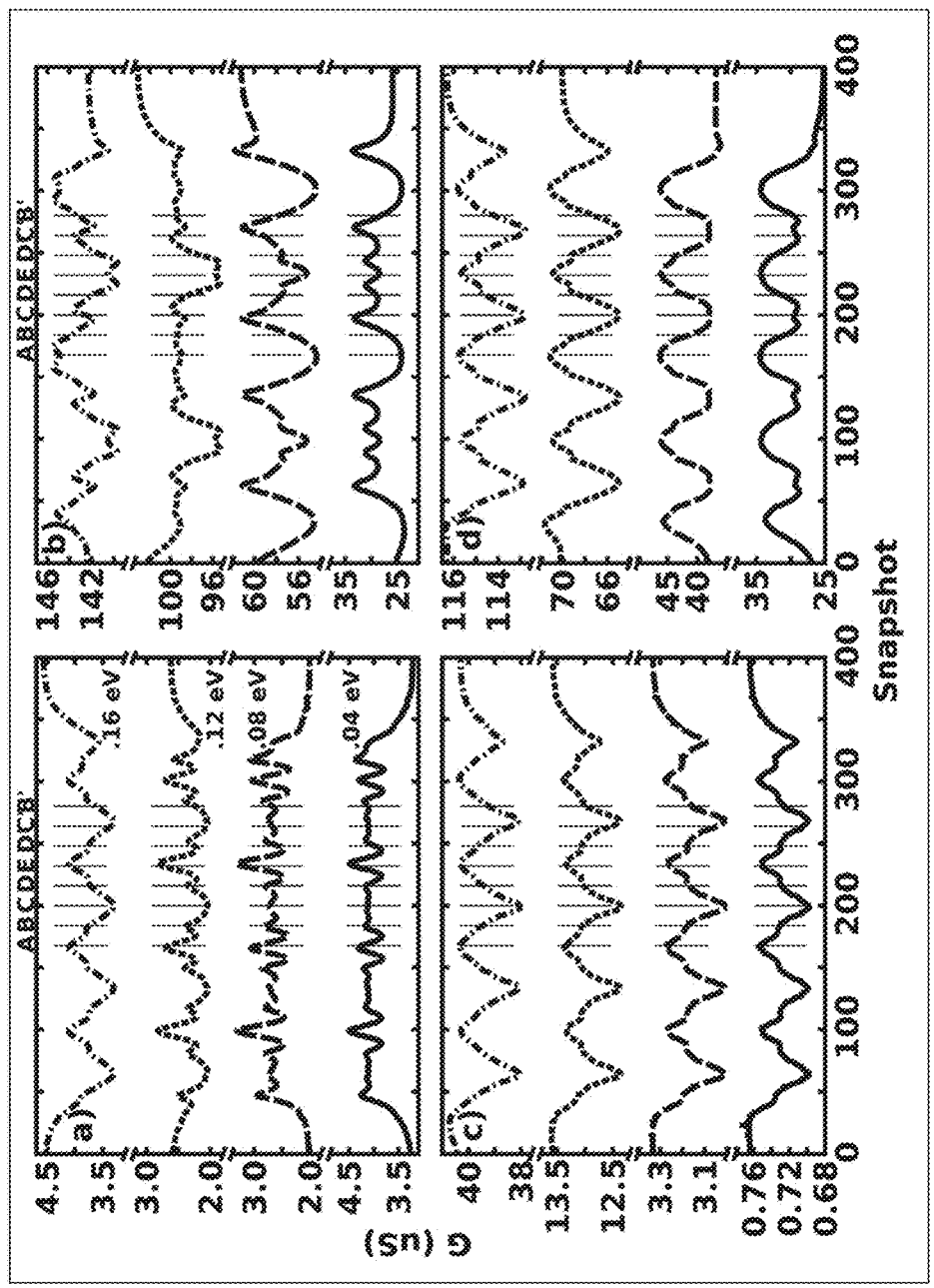
FIG. 6: Conductance as a function of DNA position (snapshot) for multiple Fermi energies, 0.04 eV (solid), 0.08 eV (long dash), 0.12 eV (short dash), and 0.16 eV (dot dash), as the DNA strand rigidly translocates through a 2.4 nm nanopore pore located at the device center (point P). a) 5-GNR, b) 15-GNR, c) 8-QPC and d) 23-QPC.

FIGS. 6a-d show the conductance as a function of the snapshot number (time) for Fermi energies 0.04 eV, 0.08 eV, 0.12 eV, and 0.16 eV above the Dirac point for each of the four geometries with a 2.4 nm pore at point P. The lines marked A-B-C-D-E-D'-C'-B' correspond to the eight potential maps in FIG. 5b, representing the translation of one full helix of the DNA. As can be seen in FIG. 6b, the 15-GNR displays the half-cycle mirroring behavior described above, only repeating after each full helix translocates through the pore. On the other hand, the 5-GNR, 8-QPC, and 23-QPC conductances shown in FIGS. 6a, 6c, and 6d respectively, display the quarter-cycle mirror effect; lines A-C represent one quarter of the helix, C-E represent the second quarter, etc. The DNA molecule in FIG. 5a, contains 24 AT base pairs, which give rise to 2.5 full turns of the double-helix. As a result, full translocation of the DNA molecule should result in 2.5 periods in the conductance curves of the 15-GNR, and 5 periods in the case of 5-GNR, 8-QPC and 23-QPC which is indeed the case as shown in FIG. 6. In these latter conductance curves, the peaks of each cycle correspond to potential map A, when the DNA axis is parallel to the y-axis, while the troughs correspond to potential map C, when the DNA axis is parallel to the x-axis. The DNA molecule is not perfectly symmetric, as the bases in a base-pair are different nucleotides; additionally, there may be a small discretization asymmetry in the potential map of the DNA. The cumulative effect is a slight difference in the conductance after a y-axis reflection, which can be recognized in FIGS. 6a, 6c, and 6d.

The large conductance variations accompanying DNA translocation through the pore demonstrate the high sensitivity of the device to external charges and their conformation. With a source-drain bias of 5 mV, the conductance (current) displays maximum variations of 0.8 to 8 μS (4 to 40 nA) depending on the particular geometry (FIG. 6), well detectable with present technology. These large variations reinforce the idea that angular position and Fermi level, in concert with each other, can strongly change the magnitude of the electrical sensitivity of the devices. Additionally, for some geometries, such as the 8-QPC (FIG. 6c), a small change in Fermi energy (0.12 eV to 0.16 eV) results in a threefold change in the magnitude of the conductance (13 μS to 40 μS) and a threefold increase in the magnitude of conductance variations (0.9 μS to 2.8 μS). Interestingly, because of the presence of NDTC regions within the investigated Fermi energy range, an increase of Fermi energy may actually decrease the conductance, as in case of the 5-GNR (FIG. 6a). Studies on electrochemical activity at the edge of graphene nanopore have been reported recently,[34] which can lead to an electrochemical sheet current in graphene of the order of 0.5 nA for a pore diameter of 2.4 nm. Although this is a large electrochemical current, the sensitivity reported here to DNA translocation is much larger than the electrochemical current measured, especially at larger Fermi energies.

Based on a simulation, a new nucleotide is within the plane of the nanopore after ~13 time steps. However, no such periodic modulation is visible in the conductance curves of FIG. 6. The reason for this is the strong screening due to the phosphate backbone on the DNA strand. As a result, the conductance variation reflects the positional changes of the backbone charges as opposed to the movement of the nucleotide charges themselves. In order to sequence DNA, one must be able to detect these nucleotides, either by translocating a single strand of DNA to prevent screening of the nucleotides by the backbone, or by making the DNA and its backbone undergo nucleotide-specific conformational changes, a topic which we are currently investigating as well as the influence of the thermal fluctuations of the DNA molecule on the g-FET conductance.

Figure 7:
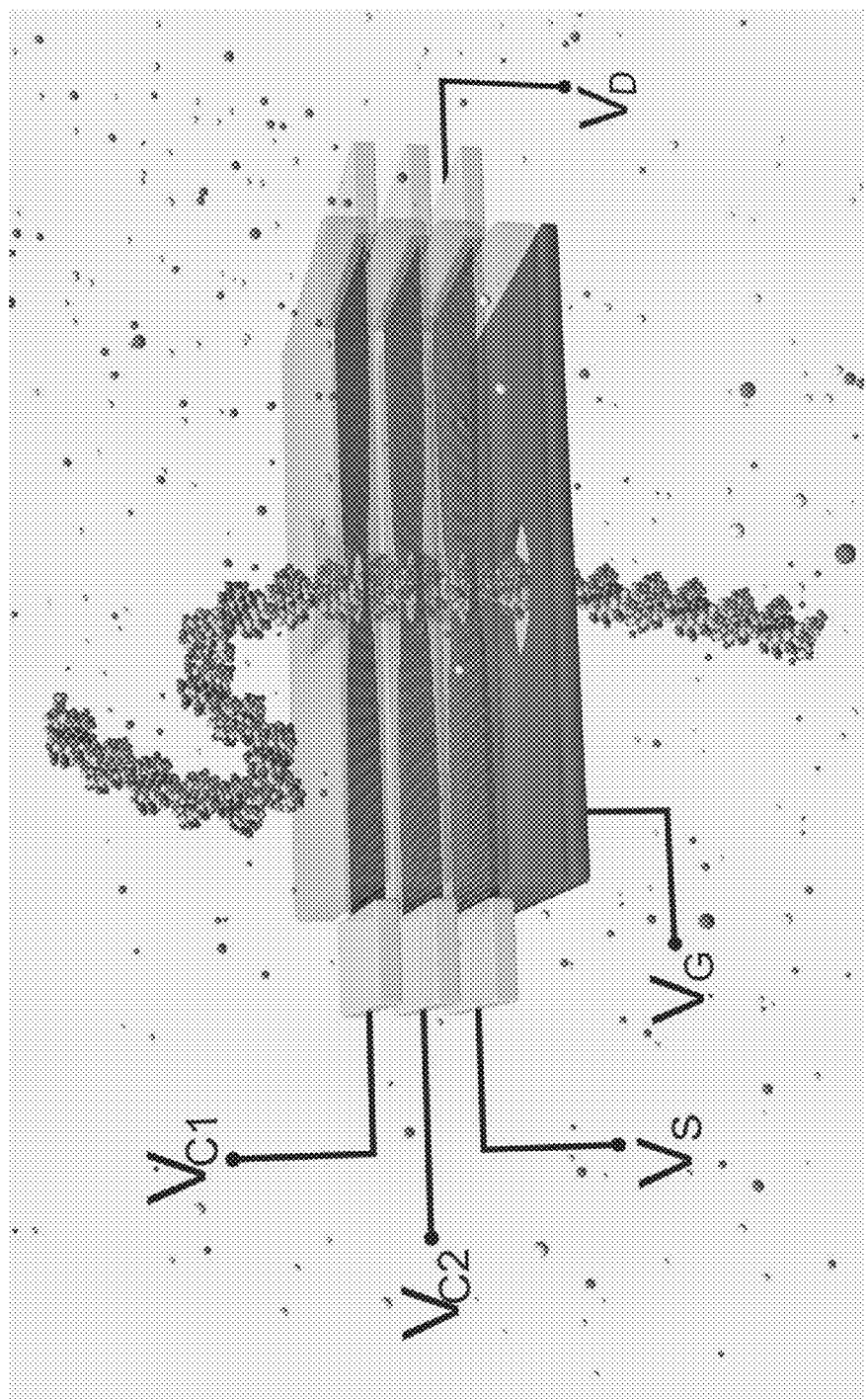
FIG. 7: Schematic diagram of a 4 layer device containing a two graphene layers (black) to control the translational motion of DNA through the nanopore. The top graphene layer ($V_{C1}$) controls the translational speed of the DNA, while the second ($V_{C2}$) controls the lateral confinement of the DNA within the nanopore. The third graphene layer ($V_{DS}$) measures the sheet current. Finally, a heavily-doped back gate (green) lies underneath the sheet current layer to control the carrier concentration. Oxide barriers (transparent) between different graphene layers provide electrical isolation. (See FIG. 13 for a cross-sectional schematic diagram)

The subject disclosure describes a strategy for sensing the molecular structure of bio-molecules by using a nanopore in electrically active mono-layer graphene shaped with a lateral constriction or QPC, employing an electrically tunable conductance to optimize detection sensitivity. The suggested measurement has been analyzed by using a self-consistent model that integrates the NEGF formalism for calculating electronic transport in the g-QPC with a detailed description of the electrical potential due to solvent, ions, and molecular charges in the nanopore. In particular, we have demonstrated that graphene QPCs are capable of detecting DNA molecules translocating through the nanopore, with a sensitivity controlled by the graphene carrier concentration. In order to achieve QPC carrier tunability, the subject disclosure describes a solid-state membrane design made of a graphene QPC sandwiched between two dielectrics to isolate the active g-layer from the electrolyte as well as suppress mechanical fluctuations of the membrane itself; the design permits simultaneous control of the carrier concentration by an external gate. The electrically active multi-layer membrane device furnishes a starting design for enhanced performance and multi-functional membranes that use more than one layer of graphene sandwiched between dielectrics or active semiconducting or metallic regions to simultaneously control and record signature of DNA passing through the nanopore (FIG. 7). Controlling the motion and translocation velocity of DNA is a currently a impediment to sequencing DNA using nanopores. One can envision that to slow down DNA translocation a bias voltage ($V_{C1}$) can be applied on one of the multiple graphene layers, which would then operate as a control gate to trap the DNA inside the pore as shown in FIG. 7. Another graphene layer ($V_{C2}$) could be used to generate a focusing field to trap the DNA and thus could help in reducing flossing of the DNA inside the pore. Finally, a third graphene layer ($V_{DS}$) could be employed to read sheet currents and discern passing nucleotides.

The electrostatic potential $\varphi(r)$ due to external charge carried by DNA is modeled as the solution of the self-consistent classical Poisson equation.

$$\nabla \cdot [\varepsilon(r) \nabla \varphi(r)] = -e[K^+(r,\varphi) - Cl^-(r,\varphi)] - \rho_{test}(r) \qquad (1)$$

Here, ε is the local permittivity. The RHS charge term comprises of ions in solution (K$^+$, Cl$^-$), test charges, or DNA charges and is written accordingly. The ion distributions obey Boltzmann statistics, namely[7]

$$K^+(r,\varphi)=c_0 \exp(-e\varphi/k_BT), Cl^-(r,\varphi)=c_0 \exp(e\varphi/k_BT) \quad (2)$$

Here, K$^+$ and Cl$^-$ are the local ion concentrations, e is the electronic charge, and $c_0$ is the molar concentration of KCl, which we have set to 1 M. Equation (1) is solved numerically as explained in the Supporting Information.

In order to model electronic transport sensitivity through a constriction in a g-QPC, the electronic properties of the patterned graphene layer through the tight-binding Hamiltonian are described (see also subject disclosure below)

$$H = \Sigma_{<i,j>} t_{ij} b_j^\dagger a_i + h.c. + \Sigma_i V_i c_i^\dagger c_i \quad (3)$$

Any charge configuration present in the nanopore modifies the on-site potentials in graphene, changing the Hamiltonian (3) and thereby the transmission probability (see Supporting Information). The conductance at the Fermi energy $E_F$ in the g-QPC can be calculated as $$G(E_F) = \frac{2e}{V_b h} \int_{-\infty}^{\infty} T(E)[f(E) - f(E + eV_b)] \quad (4)$$

where, $f(E)=[\exp((E-E_F)/k_BT)+1]^{-1}$ is the Fermi-Dirac distribution. The carrier concentration n is controlled by the external gate bias $V_G$, i.e. en=$C_D(V_G-V_T)$ where $C_D$ is the dielectric capacitance and $V_T$ is the threshold voltage for electron or hole conduction in the QPC. Since $E_F=E_F(n)$, the carrier concentration and the Fermi energy can be interchangeable, even though the Fermi energy is the relevant parameter. A source-drain bias ($V_b$) of 5 mV and a system temperature of 300 K can be assumed. Conductance may be reduced by non-ideal boundaries of the QPC. However, the main conclusions pertain to the response of the conductance to changes in the overall geometry and carrier concentration, and they are expected to remain valid if the conductance is significantly reduced, even by an order of magnitude.

By using the Non-Equilibrium Green's Function technique the subject disclosure shows that the shape of the edge, the carrier concentration, and the position and size of a nanopore in graphene nanoribbons can strongly affect its electronic conductance as well as its sensitivity to external charges. This technique, combined with a self-consistent Poisson-Boltzmann formalism to account for ion charge screening in solution, is able to detect the rotational and positional conformation of a DNA strand inside the nanopore. The subject disclosure shows that a graphene membrane with quantum point contact (QPC) geometry exhibits greater electrical sensitivity than a uniform armchair geometry provided that the carrier concentration is tuned to enhance charge detection. The subject disclosure generally describes a membrane design that contains an electrical gate for a graphene-based DNA sensing device.

Rapidly sequencing the human genome in a cost-effective manner can revolutionize modern medicine. This subject describes a new paradigm for sensing DNA molecules by threading them through an electrically active solid-state nanopore device containing a constricted graphene layer. The subject disclosure shows that the electrical sensitivity of the graphene layer can be easily tuned by both shaping its geometry and modulating its conductance by means of an electric gate integrated in the membrane.

The tight-binding graphene Hamiltonian is given by $$H = \sum_{\langle i,j \rangle} t_{ij} b_j^\dagger a_i + h.c. \quad (S5)$$

where $t_{ij}$ is the site-dependent hopping parameter and $b_j^\dagger a_i$ represents an electron hopping from an A sublattice site i to a nearest-neighbor B sublattice site j. After transforming this to a momentum-space representation and solving for the band structure, we notice that the Fermi energy of the system lies at two non-equivalent points in the first Brillouin zone designated K and K', respectively. After expanding around these two points, for low energies, we obtain the Dirac equation and the corresponding full wavefunction Ψ for each sublattice.

$$H_q = \mp i\hbar v_F \sigma \cdot q \quad (S6)$$

$$\Psi_{q,A/B}(r) = e^{iK\cdot r}\psi_{q,A/B}(r) + e^{iK'\cdot r}\psi'_{q,A/B}(r) \quad (S7)$$

Here, ∓ refers to the K,K' points respectively (known as the two Dirac points), and ψ,ψ' are the eigenspinors corresponding to the K,K' Hamiltonians. To study graphene nanoribbons (GNRs), we assume both translational invariance and that the total wavefunction goes to zero at the boundaries on each sublattice independently. Because each component of the total wavefunction needs to be zero at the boundary simultaneously, the relationship between components can become quite complicated, especially when considering a non-uniform GNR edge.[2] This will result in a very nonlinear and complex transmission function when compared to the uniform GNR case (FIG. 2).

A tight-binding Hamiltonian can be implemented as a sparse matrix M where the matrix element $M_{ij}$ represents the interaction between lattice sites i and j. The hexagonal lattice is represented as square lattice by a simple transformation, preserving the topology of the lattice. The non-equilibrium Green's function (NEGF) formalism, associated with the Hamiltonian (S1) permits one to calculate the transport properties of the g-QPC device. Including the effects of the leads, the Green's function for the full device reads $$G_D = \left[E + i\eta - H_D - \sum_p V_{pD} g_p V_{Dp}\right]^{-1} = \left[E + i\eta - H_D - \sum_p S_p\right]^{-1} \quad (S8)$$

where $H_D$ is the device Hamiltonian without leads, $V_{pD}$ and $V_{Dp}$ are interaction potentials between the isolated device and the lead p, and $g_p$ is the Green's function of the isolated lead p. $S_p$ is the self-energy of lead p. To calculate $g_p$ of the semi-infinite lead p, we use the recursive technique described by Sancho et al. An algorithm was executed for 200 recursions, beyond what is required for convergence. The transmission probability from lead p to lead q is $$T_{pq}(E) = Tr(\Gamma_p G_D \Gamma_q G_D^\dagger) \text{ with } \Gamma_p = i(S_p - S_p^\dagger) \quad (S9)$$

from which one can calculate the conductance. The matrix equations are solved using the sparse matrix linear solving algorithms included in a Scipy v0.11.0 package, linked against the UMFPACK v5.2 sparse matrix routines.

The non-linear Poisson equation described above is solved using a Newton-multigrid scheme. The anisotropy in the permittivity of the system requires a finite volume discretization with operator-based interpolation for the grid operators used in the multigrid scheme. The system employs a non-uniform mesh with a mesh size ranging from (Å/3 near the pore mouth and 3 Å/2 far away from the pore mouth). The maximum size of the mesh points used in the simulation was 256×512×256. The relativity permittivity of water and graphene were set to 78 and 6 respectively. The system was subject to Dirichlet conditions along the $\hat{z}$ direction, and Neumann boundary conditions are applied in $\hat{x}$ and $\hat{y}$ (FIG. 2) directions. The simulated system size varies from 10×5×20 nm$^3$ to 10×23×20 nm$^3$.

The initial structure of the DNA was generated using the program X3DNA and the psfgen module of VMD. The atomic coordinates and charge from the DNA were then mapped onto a 3D grid, which was used as the input charge configuration for the Poisson solver.

Figure 8:
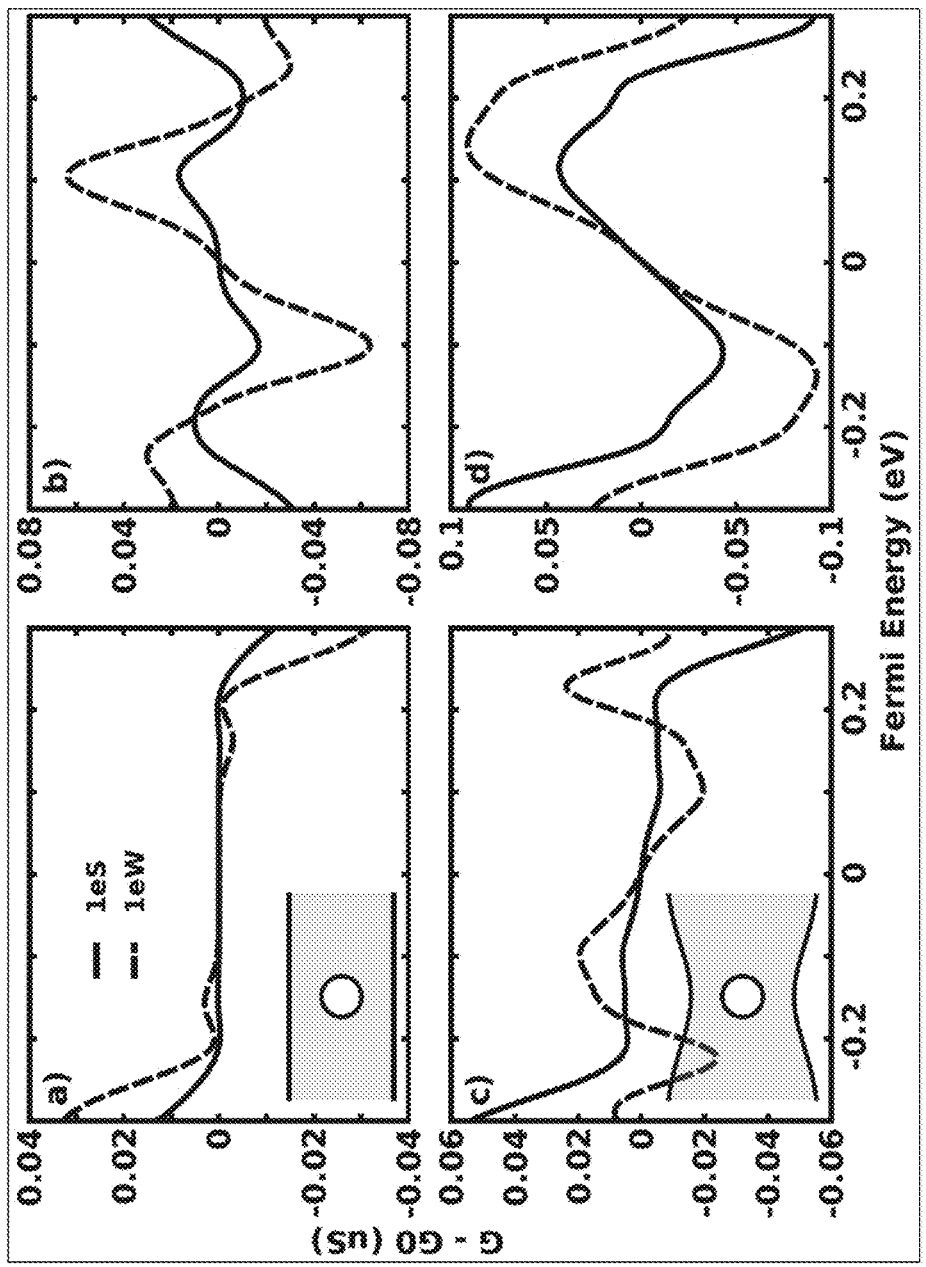
FIG. 8: Conductance variations of placing an eighth of an electron test charge in the south and west positions of a 2 nm nanopore located at point P (figure inset) in a a) 5-GNR, b) 15-GNR, c) 8-QPC, and d) 23-QPC.

FIG. 8 shows the conductance variation of placing an eighth of an electron test charge in the west and south positions of the 2 nm nanopore located at point P (FIG. 8 inset). As mentioned above, the variations follow virtually the same trend as for the full electron test charge, except for a scaling by factor ⅛, as expected due to the linear scaling of the potential with test charge magnitude.

Figure 9:
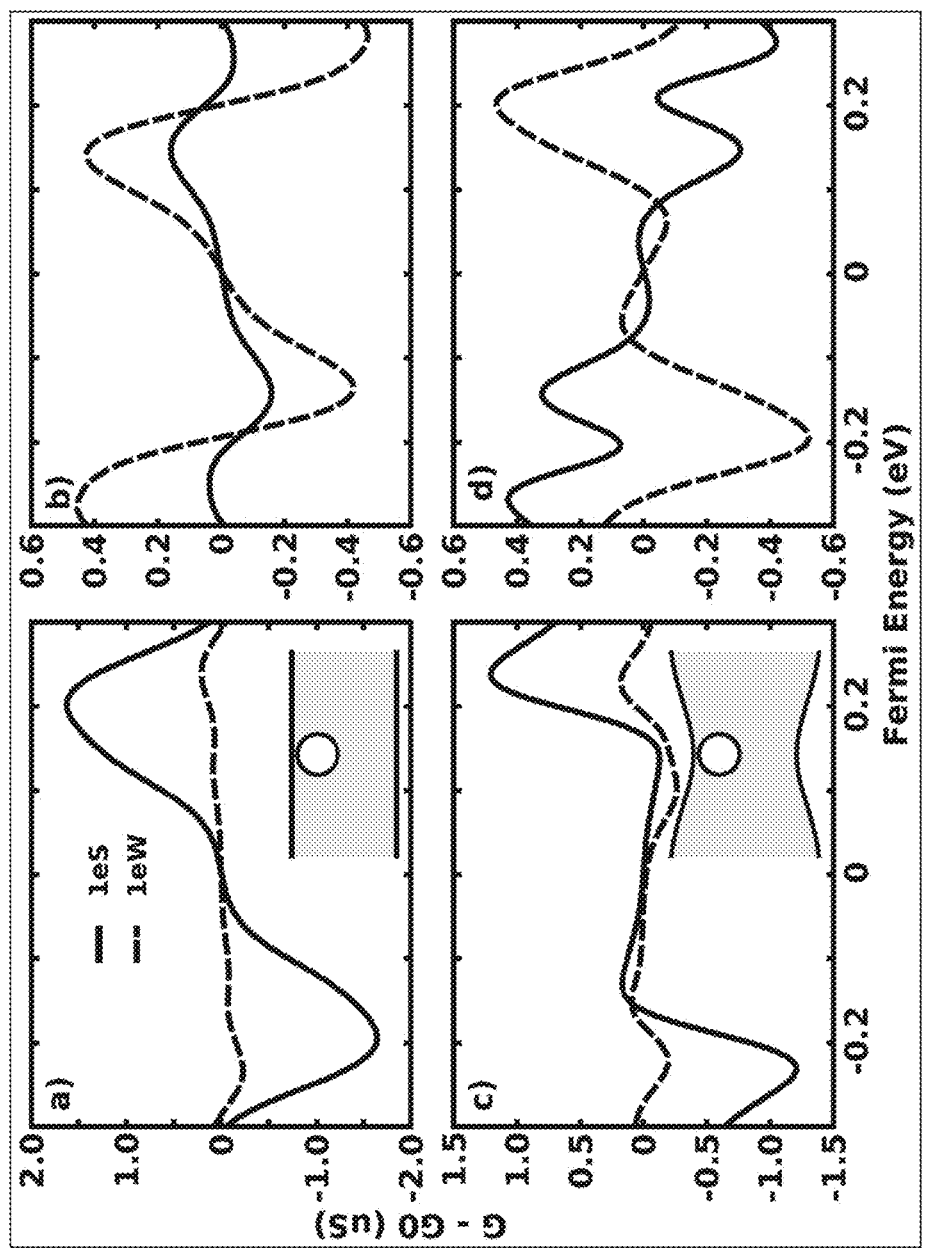
FIG. 9: Conductance variations of placing a full electron test charge in the south and west positions of a 2 nm nanopore located at point Q (figure inset) in a a) 5-GNR, b) 15-GNR, c) 8-QPC, and d) 23-QPC.

FIG. 9 shows the conductance variation of placing a full electron test charge in the west and south positions of the 2 nm nanopore located at point Q (FIG. 9 inset) of each of the four edge geometries. Similar to the case with the pore at P, the variations are strongly dependent on the position of the charge within the nanopore as well as the Fermi level. The magnitudes of the conductance variations in the 5-GNR (FIG. 9a) and 8-QPC (FIG. 9c) geometries are larger than those of the same geometries with the pore at point P. Here, for the 5-GNR, the largest variations are almost 1.7 μS for a charge placed in the south position of the pore in the 5-GNR, and are almost 1.3 μS for a charge placed in the south position of the 8-QPC pore. When the charge is placed in the west position of the pore, on the other hand, the conductance variations are much smaller, being 0.25 μS and 0.2 μS for the 5-GNR and 8-QPC, respectively. This once again demonstrates the large sensitivity of the conductance to the angular position of the charge within the nanopore.

Figure 10:
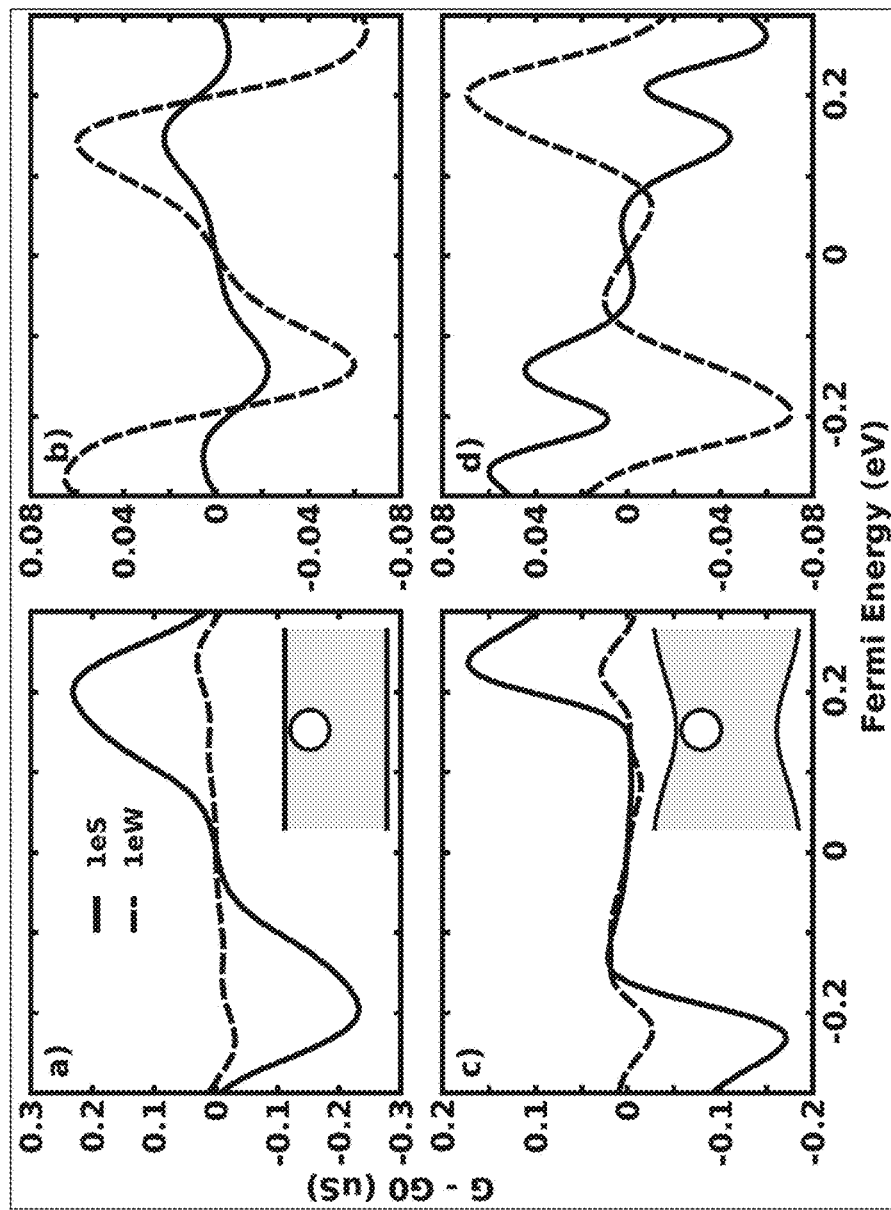
FIG. 10: Conductance variations of placing an eighth of an electron test charge in the south and west positions of a 2 nm nanopore located at point Q (figure inset) in a) 5-GNR, b) 15-GNR, c) 8-QPC, and d) 23-QPC.
Figure 11:
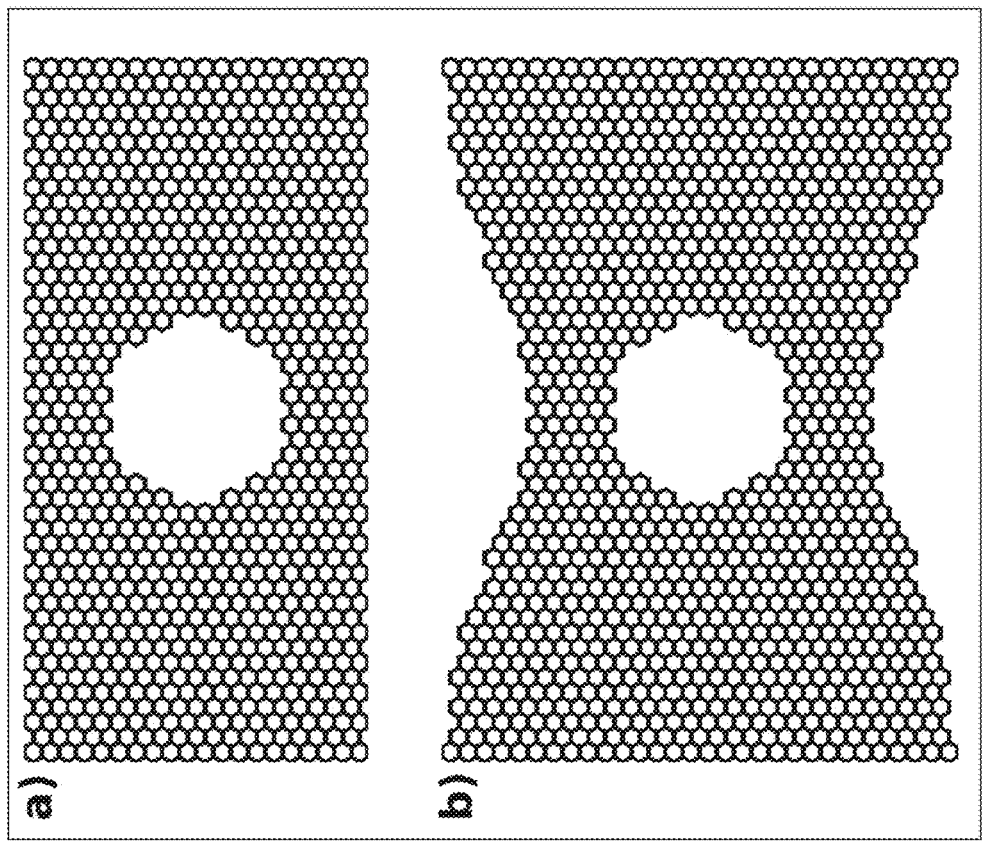
FIG. 11: Illustration depicting the precise lattice configuration used to simulate the a) 5-GNR and b) 8-QPC nanoribbons with a 2.4 nm diameter nanopore.
Figure 12:
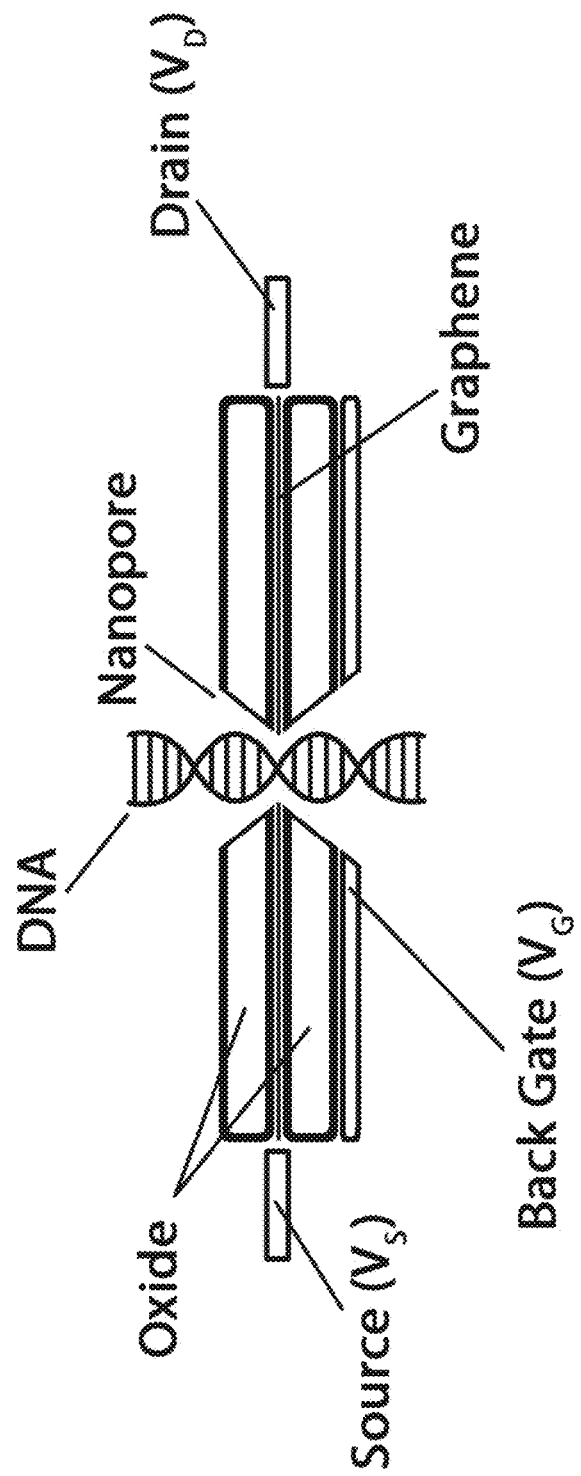
FIG. 12: Cross-sectional schematic diagram through the central axis of the nanopore of the multilayer device illustrated in FIG. 1 showing source ($V_S$) and drain ($V_D$) contacts as well as the back gate ($V_G$)
Figure 13:
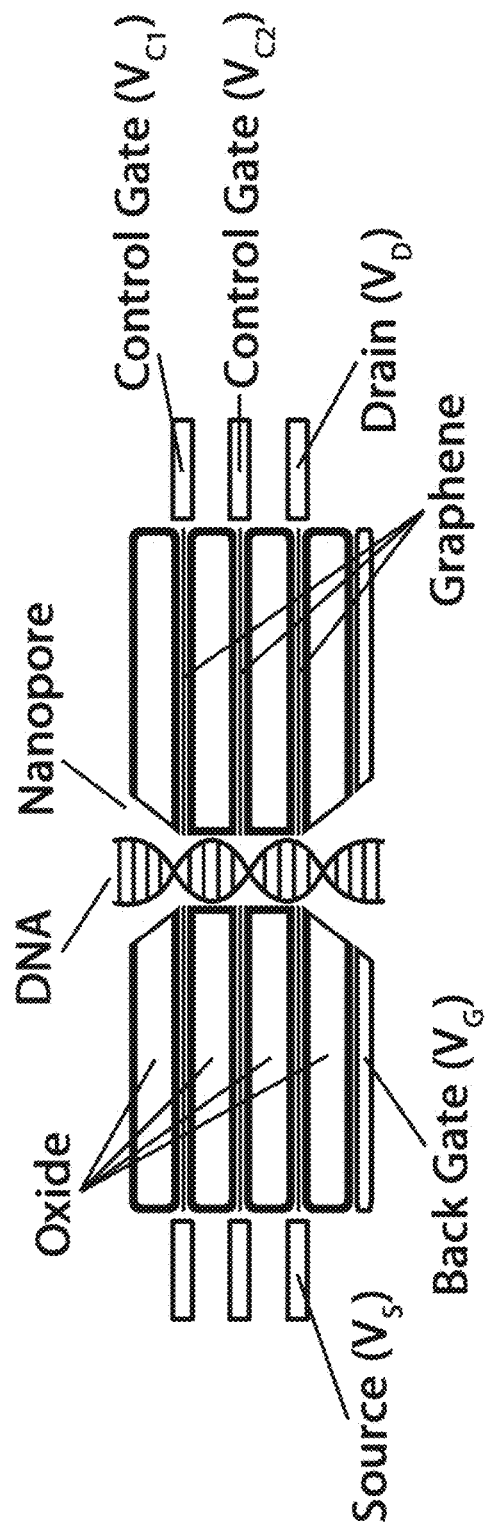
FIG. 13: Cross-sectional schematic diagram through the central axis of the nanopore of the multilayer device illustrated in FIG. 7 showing source ($V_S$), drain ($V_D$), and control ($V_{C1}$ and $V_{C2}$) contacts, as well as a back gate ($V_G$)

For the wider 15-GNR (FIG. 9b) and 23-QPC (FIG. 9d) geometries, the conductance variations are similar in magnitude for the geometries with the pore at point P. For the 15-GNR, the maximum conductance variations are 0.45 μS and 0.18 μS for a test charge placed in the west and south positions of the pore, respectively. For the 23-QPC, the largest variations are 0.5 μS and 0.45 μS for a test charge placed in the west and south positions in the pore, respectively. In all four cases, the conductance variations do not follow a strictly increasing relationship with Fermi energy, displaying many regions of negative differential resistance, sometimes of large magnitude. For example, as seen in FIG. 9b, the conductance variation drops by 0.8 μS, a factor of over 200%, when the Fermi energy is changed from 0.15 eV to 0.25 eV. As a result, the Fermi energy plays a strong role in determining the sensitivity of these devices to external electric potentials. FIG. 10 shows the conductance variations for an eighth of an electron test charge placed in a 2 nm pore at point Q (FIG. 10 inset) for all four geometries. Similarly to the other case, the charge variations are almost identical to the full electron case, scaled by a factor ⅛, as expected.

Figure 14:
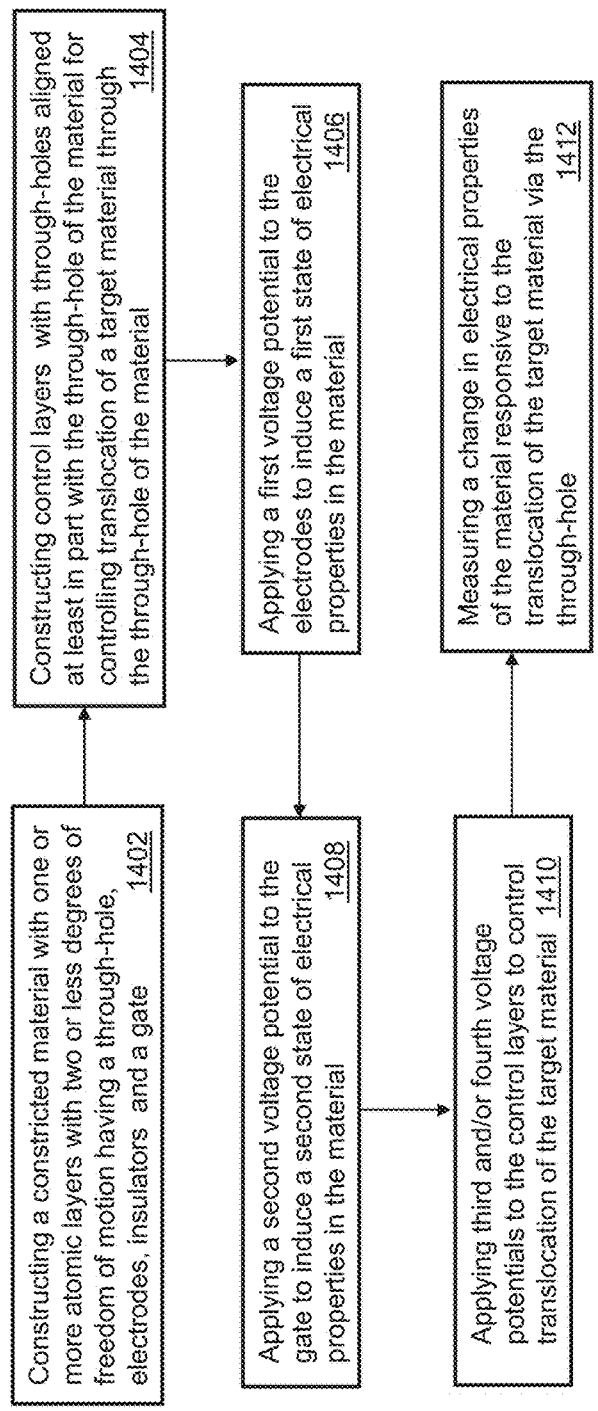
FIG. 14 depicts an illustrative method for constructing and utilizing the embodiments in the subject disclosure.

FIG. 14 depicts an illustrative method 1400 for constructing and utilizing the embodiments in the subject disclosure. Method 1400 can begin with constructing at step 1402 a constricted material having a through-hole and electrodes and insulators such as shown in FIG. 1. The material can be any material having one or more atomic layers with two or less degrees of freedom of motion of charges in the material such as, for example, grapheme, molybdenum disulfide, transition metal chalcogenides, or combinations thereof. The insulators can comprise an oxide material or dielectric material such as aluminum oxide, a hafnium oxide, a silicon dioxide, or combinations thereof, and the dielectric material can be, for example, silicon nitride. The through-hole can be a nanopore with a regular or irregular shape. The constriction can also be of a regular or irregular shape. The gate can be constructed from any material that can cause a change in carrier concentration in the material having the constriction such as, for example, a metal, a doped semiconductor, graphene, or combinations thereof. The target material can be embedded in a liquid solution (such as an ionic solution) for assisting the translocation of the target material in the through-holes. At step 1404, control layers can be constructed in addition to the structure of described at step 1402 with through-holes aligned at least in part with the through-hole of the constricted material for controlling translocation of the target material through the through-hole of the constricted material such as shown in FIG. 7. The target material can be a biological or non-biological material, which is intended to be analyzed while traversing the through-hole of the material having the constriction.

To analyze the target material, a first voltage potential can be applied at step 1406 to the electrodes of the constricted material to induce a first state of electrical properties in the material (e.g., Vs and Vd). The state of electrical properties can include, for example, inducing conductance of charges (holes and/or electrons) in the constricted material, or inducing an electric field applied to the charges in the constricted material which may or may not result in the conduction of the charges. At step 1408, a second voltage potential can be applied to the gate (Vg) to induce a second state of electrical properties in the material. The second state can include inducing a change in charge concentration of charges in the constricted material. To control translocation of the target material, third and fourth voltage potentials (Vc1 and Vc2) can be applied to the control layers at step 1410. As the target material traverses the through-hole of the constricted material, segments of the target material can in turn cause changes in the electrical properties of the constricted material. Such changes can be measured at step 1412 according to a change in voltage, current or both in the constricted material of step 1402.

From the foregoing descriptions, it would be evident to an artisan with ordinary skill in the art that the aforementioned embodiments can be modified, reduced, or enhanced without departing from the scope and spirit of the claims described below. For example, a controller (such as a microcomputer or state machine) can be used to control variable voltage sources that apply the voltage potentials described in method 1400. A sensor such as a voltmeter or ammeter can be used and controlled by the controller for measuring changes in the electrical properties of the constricted material. Other suitable modifications can be applied to the subject disclosure. Accordingly, the reader is directed to the claims for a fuller understanding of the breadth and scope of the subject disclosure.

References Cited in the Disclosure Below

[1] D. Branton, D. W. Deamer, A. Marziali, H. Bayley, S. A. Benner, T. Butler, M. D. Ventra, S. Garaj, A. Hibbs, X. Huang, S. B. Jovanovich, P. S. Krstic, S. Lindsay, X. S. Ling, C. H. Mastrangelo, A. Meller, J. S. Oliver, Y. V. Pershin, J. M. Ramsey, R. Riehn, G. V. Soni, V. Tabard-Cossa, M. Wanunu, M. Wiggin, and J. A. Schloss. Distinguishing Single- and Double-Stranded Nucleic Acid Molecules Using Solid-State Nanopore. *Nature Biotechnology*, 26:1146-1153, 2008.

[2] J. A. Schloss. How to get genomes at one ten-thousandth the cost. *Nature Biotechnology*, 26:1113, 2008.

[3] E. E. Schadt, S. Turner, and A. Kasarskis. A window into third-generation sequencing. *Human molecular genetics*, 19:R227-R240, 2010.

[4] S. Howorka and Z. Siwy. Nanopore analytics: sensing of single molecules. *Chem. Soc. Rev.*, 38:2360-2384, 2009.

[5] J. J. Kasianowicz, E. Brandin, D. Branton, and D. W. Deamer. Characterization of individual polynucleotide molecules using a membrane channel. *Proceedings of the National Academy of Sciences, USA*, 93:13770-13773, 1996.

[6] M. E. Gracheva, A. Xiong, A. Aksimentiev, K. Schulten, G. Timp, and J.-P. Leburton. Simulation of the electric response of DNA translocation through a semiconductor nanopore-capacitor. *Nanotechnology*, 17:622-633, 2006.

[7] M. Zwolak and M. D. Ventra. Electronic signature of dna nucleotides via transverse transport. *Nano Letters*, 5:421-424, 2005.

[8] A. C. Neto, F. Guinea, N. Peres, K. S. Novoselov, and A. K. Geim. The electronic properties of graphene. *Reviews of modern physics*, 81:109, 2009.

[9] K. K. Saha, M. Drndić, and B. K. Nikolić. DNA base-specific modulation of microampere transverse edge currents through a metallic graphene nanoribbon with a nanopore. *Nano Letters*, 12:50-55, 2012.

[10] S. M. Avdoshenko, D. Nozaki, C. Gomes da Rocha, J. W. Gonzàlez, M. H. Lee, R. Gutierrez, and G. Cuniberti. Dynamic and electronic transport properties of DNA translocation through graphene nanopores. *Nano Letters*, 13:1969-1976, 2013.

[11] G. F. Schneider, S. W. Kowalczyk, V. E. Calado, G. Pandraud, H. W. Zandbergen, L. M. K. Vandersypen, and C. Dekker. DNA translocation through graphene nanopores. *Nano Letters*, pages 3163-3167.

[12] C. A. Merchant, K. Healy, M. Wanunu, V. Ray, N. Peterman, J. Bartel, M. D. Fischbein, K. Venta, Z. Luo, A. T. C. Johnson, and M. Drndić. DNA translocation through graphene nanopores. *Nano Letters*, 10:2915-2921, 2010.

[13] S. Garaj, W. Hubbard, A. Reina, J. Kong, D. Branton, and J. A. Golovchenko. Graphene as a subnanometer trans-electrode membrane. *Nature*, 467:190-193, 2010.

[14] S. Garaj, S. Liu, J. A. Golovchenko, and D. Branton. Molecule-hugging graphene nanopores. 110:12192-12196, 2013.

[15] M. Ezawa. Peculiar width dependence of the electronic properties of carbon nanoribbons. *Physical Review B*, 73:045432, 2006.

[16] L. Brey and H. Fertig. Electronic states of graphene nanoribbons studied with the dirac equation. *Physical Review B*, 73:235411, 2006.

[17] M. Y. Han, B. Özyilmaz, Y. Zhang, and P. Kim. Energy band-gap engineering of graphene nanoribbons. *Physical review letters*, 98:206805, 2007.

[18] F. Cervantes-Sodi, G. Csanyi, S. Piscanec, and A. Ferrari. Edge-functionalized and substitutionally doped graphene nanoribbons: Electronic and spin properties. *Physical Review B*, 77:165427, 2008.

[19] A. Girdhar, C. Sathe, K. Schulten, and J.-P. Leburton. Graphene quantum point contact transistor for DNA sensing. *Proceedings of the National Academy of Sciences, USA*, 110:16748-16753, 2013.

[20] M. Puster, J. A. Rodríguez-Manzo, A. Balan, and M. Drndić. Toward sensitive graphene nanoribbon-nanopore devices by preventing electron beam-induced damage. *ACS Nano*, 7:11283-11289, 2013.

[21] F. Traversi, C. Raillon, S. Benameur, K. Liu, S. Khlybov, M. Tosun, D. Krasnozhon, A. Kis, and A. Radenovic. Detecting the translocation of DNA through a nanopore using graphene nanoribbons. *Nature nanotechnology*, 8:939-945, 2013.

[22] A. Girdhar, C. Sathe, K. Schulten, and J.-P. Leburton. Gate-modulated graphene quantum point contact device for DNA sensing. *Journal of Computational Electronics*, 13:839-846, 2014.

[23] M. E. Gracheva, J. Vidal, and J.-P. Leburton. p-n semiconductor membrane for electrically tunable ion current rectification and filtering. *Nano letters*, 7:1717-1722, 2007.

[24] M. E. Gracheva, D. V. Melnikov, and J.-P. Leburton. Multilayered semiconductor membranes for nanopore ionic conductance modulation. *ACS nano*, 2:2349-2355, 2008.

[25] X.-J. Lu and W. K. Olson. 3DNA: a software package for the analysis, rebuilding and visualization of three-dimensional nucleic acid structures. *Nucleic Acids Research*, 31:5108-5121, 2003.

[26] J. C. Phillips, R. Braun, W. Wang, J. Gumbart, E. Tajkhorshid, E. Villa, C. Chipot, R. D. Skeel, L. Kale, and K. Schulten. Scalable molecular dynamics with NAMD. *Journal of Computational Chemistry*, 26:1781-1802, 2005.

[27] A. D. MacKerell, Jr., D. Bashford, M. Bellott, R. L. Dunbrack, Jr., J. D. Evanseck, M. J. Field, S. Fischer, J. Gao, H. Guo, S. Ha, D. Joseph, L. Kuchnir, K. Kuczera, F. T. K. Lau, C. Mattos, S. Michnick, T. Ngo, D. T. Nguyen, B. Prodhom, I. W. E. Reiher, B. Roux, M. Schlenkrich, J. Smith, R. Stote, J. Straub, M. Watanabe, J. Wiorkiewicz-Kuczera, D. Yin, and M. Karplus. All-atom empirical potential for molecular modeling and dynamics studies of proteins. *Journal of Physical Chemistry B*, 102:3586-3616, 1998.

[28] W. L. Jorgensen, J. Chandrasekhar, J. D. Madura, R. W. Impey, and M. L. Klein. Comparison of simple potential functions for simulating liquid water. *Journal of Chemical Physics*, 79:926-935, 1983.

[29] G. J. Martyna, D. J. Tobias, and M. L. Klein. Constant pressure molecular dynamics algorithms. *Journal of Chemical Physics*, 101:4177-4189, 1994.

[30] M. Sotomayor and K. Schulten. Single-molecule experiments in vitro and in silico. *Science*, 316:1144-1148, 2007.

[31] E. H. Lee, J. Hsin, M. Sotomayor, G. Comellas, and K. Schulten. Discovery through the computational microscope. *Structure*, 17:1295-1306, 2009.

[32] B. Isralewitz, M. Gao, and K. Schulten. Steered molecular dynamics and mechanical functions of proteins. *Current Opinion in Structural Biology*, 11:224-230, 2001.

[33] M. Gao, M. Sotomayor, E. Villa, E. Lee, and K. Schulten. Molecular mechanisms of cellular mechanics. *Physical Chemistry—Chemical Physics*, 8:3692-3706, 2006.

[34] T. B. Boykin, M. Luisier, G. Klimeck, X. Jiang, N. Kharche, Y. Zhou, and S. K. Nayak. Accurate six-band nearest-neighbor tight-binding model for the π-bands of bulk graphene and graphene nanoribbons. *Journal of Applied Physics*, 109, 2011.

[35] S. Konschuh, M. Gmitra, and J. Fabian. Tight-binding theory of the spin-orbit coupling in graphene. *Physical Review B*, 82:245412, 2010.

[36] S. Datta. *Electronic transport in mesoscopic systems*. Cambridge university press, 1997.

[37] C. Sathe, A. Girdhar, J.-P. Leburton, and K. Schulten. Electronic detection of dsdna transition from helical to zipper conformation using graphene nanopores. *Nanotechnology*, 25:445105, 2014.

[38] J. Mathé, A. Aksimentiev, D. R. Nelson, K. Schulten, and A. Meller. Orientation discrimination of single stranded DNA inside the α-hemolysin membrane channel. *Proceedings of the National Academy of Sciences, USA*, 102:12377-12382, 2005.

A graphene membrane conductor containing a nanopore in a quantum point contact (QPC) geometry is a promising candidate to sense, and sequence, DNA molecules translocating through the nanopore. Within this geometry, the shape, size, and position of the nanopore as well as the edge configuration influences the membrane conductance caused by the electrostatic interaction between the DNA nucleotides and the nanopore edge. It is shown that the graphene conductance variations resulting from DNA translocation can be enhanced by choosing a particular geometry as well as by modulating the graphene Fermi energy, which demonstrates the ability to detect conformational transformations of a double-stranded DNA, as well as the passage of individual base pairs of a single-stranded DNA molecule through the nanopore.

In recent years, there has been immense interest in finding a low-cost, rapid genome sequencing method [1, 2, 3]. Amongst such methods, the use of solid-state nanopore (SSN) membranes is a new technology that can lead to tremendous advancement in the field of personalized medicine [4]. In a SSN device, a nanometer-sized membrane with a nanopore separates an ionic solution into two chambers. When a DNA molecule is electrophoretically driven across the membrane through the nanopore, it can be probed electronically, allowing the passing nucleotides to be detected. The detection methods include measuring ionic blockade currents [5], recording the electrostatic potential induced by the DNA using a semiconductor capacitor [6], and using transverse currents to probe translocating DNA in a plane perpendicular to the translocation direction [7].

For these approaches, biomolecular sensors with graphene membranes can be well suited for DNA sequencing. Graphene is a two-dimensional allotrope of carbon, whose thickness of ~3.35 Å is comparable to the base separation and can resolve translocating DNA at a very high resolution, revealing detailed information about its nucleotides [8, 9, 10]. Recent experiments have demonstrated the successful detection of both double-stranded DNA (dsDNA) [11, 12, 13] and single-stranded DNA (ssDNA) [14] using graphene-based nanopores. Unlike many solid-state membranes, graphene is electrically active and can readily conduct electronic currents. Moreover, it can be cut into narrow strips called graphene nanoribbons (GNRs), for which edge shape determines their electronic properties [15, 16, 17, 18]. The size of the graphene band-gap and the density of electronic states at a particular energy can be altered by changing the width, edge shape, lattice chirality, and presence of any nanopores. In addition, the position and shape of a nanopore can similarly affect the electronic states, influencing the magnitude of the graphene electrical conductance as well as its behavior under electrostatic disturbances [19].

Theoretical and first-principles-based calculations suggest micro-Ampere edge currents pass through GNR membranes as well as the possibility of distinguishing base pairs of DNA with graphene nanopores [9, 10]. Experiments have demonstrated that micro-ampere sheet currents can arise in GNRs with nanopores [20]. Such structures have the ability to detect DNA molecules by observing variation in the sheet current when the biomolecules pass through the pore [21]. In this context, a multi-layer graphene nanopore transistor with a gate-controlled, electrically active GNR membrane shaped as a quantum point contact (QPC) was recently proposed to detect the rotational and positional orientation of dsDNA [19, 22]. The QPC edge shape offers advantages over pristine edges as it introduces stringent boundary conditions on the electronic wave functions with selective sensitivity on the electrostatic environment. This property results in a large enhancement of the conductance sensitivity whenever the carrier density is modulated by a transistor gate, thereby improving the capability of discerning a nucleotide signal from the background noise. The multiscale model relies on a Poisson-Boltzmann formalism to account for DNA electrostatics in an ionic solution combined with a transport model based on Non-Equilibrium Greens Function (NEGF) theory. The proposed device architecture also allows for the presence of additional electronic layers within the membrane to alter the electrostatic profile of the nanopore, such as for the control of DNA motion, as has been shown in a previous study with doped silicon capacitor layers [23, 24].

The subject disclosure outlines a comprehensive review on the ability of GNRs with a QPC geometry (g-QPC) to detect and characterize the passage of both double and single-stranded DNA molecules in a variety of configurations. In particular, the subject disclosure demonstrates the ability of a g-QPC to detect the helical nature of dsDNA, to sense the conformational transitions of dsDNA subjected to forced extension, and to distinctively count base pairs of a passing ssDNA molecule through the nanopore. The subject disclosure also shows that both the position of the nanopore as well as the electrical bias on a gate electrode can drastically influence the conductance variation in response to the charge carried by a biomolecule. In addition, subject disclosure shows that the diameter and shape of the pore both play a significant role in the sensitivity of the conductance signal to the nucleotides of a ssDNA molecule.

In order to investigate the conductance response to the translocation of a DNA molecule through a g-QPC nanopore, we have developed a comprehensive multi-scale, multi-phase model. First, a molecular dynamics simulation is performed to obtain the trajectories of the translocating DNA molecule. Next, we extract the ionic and molecular charge configuration to find the electrostatic potential in the g-QPC membrane for each trajectory time step (snapshot) by solving the Poisson equation over the whole electrolyte-membrane domain. Finally, the electrostatic potential is used to calculate the electronic and transport properties of the g-QPC during the DNA translocation. Each of these three steps is outlined below.

DNA Atomic Charge Model

The atomic coordinates and charges of a DNA molecule are described using all-atom molecular dynamics (MD) simulations. There are three DNA charge models employed in the subject disclosure, namely, an ideal 24 base pair dsDNA model, conformations of a 15 base pair dsDNA strand obtained from a forced extension from a helical (B-form) to a zipper (zip-form) conformation, and one linear conformation of a 16 base pair ssDNA obtained from MD simulations.

The atomic coordinates of the initial structure of the DNA molecules were built using the program X3DNA [25], and the topology of the DNA, along with missing hydrogen atoms, was generated using psfgen [26]. The 15 base pair dsDNA (16 base pair ssDNA) molecule was placed in a water box and neutralized at 1 M KCl (0.3 M KCl). The dimensions of the solvated system was 70 Å×70 Å×110 Å

(60 Å×60 Å×180 Å) and contained about 52,000 atoms (64,000 atoms). All molecular dynamics simulations were performed using NAMD 2.9 [26], using periodic boundary conditions. CHARMM27 force field parameters were employed for DNA [27], ions and TIP3P water molecules [28]. The integration time step used was 2 fs with particle-mesh Ewald (PME) full electrostatics with grid density of 1/Å$^3$. Van der Waals energies were calculated using a 12 Å cutoff, and a Langevin thermostat was assumed to maintain constant temperature at 295 K [29].

The system was first minimized for 4000 steps, then heated to 295 K in 4 ps. After heating, the DNA was constrained, and a 500 ps-equilibration was conducted under NPT ensemble conditions, using the Nosé-Hoover Langevin piston pressure control at 1 bar [29]. After the system acquired a constant volume in the NPT ensemble, 1.5 ns-equilibration was conducted in an NVT ensemble. Steered Molecular Dynamics (SMD) simulations [30, 31] were employed to induce forced extension of DNA molecule. The dsDNA was stretched by pulling both strands on one end of the dsDNA at a constant velocity of 1 Å/ns along the z-direction, while harmonically restraining the other end. In the case of the ssDNA molecule the 5' end of the strand was pulled at a constant velocity of 10 Å/ns, restraining the 3' end of the strand. The pulled atoms were attached to one end of a virtual spring; the other end of the spring, a dummy atom, was moved at a constant pulling speed along the pulling direction. The pulled atoms experience a force $f = -k[z(t) - z(t0) - v(t - t0)]$, where $z(t0)$ is the initial position of the dummy atom attached to the spring. The spring constant k was chosen to be equal to $3k_B T_0/Å^2$ ($k_B$ is the Boltzmann constant; $T_0 = 295$ K), corresponding to a thermal RMSD deviation of $k_B T_0/k \approx 0.6$ Å, typical for SMD simulations [30, 31, 32, 33]. After a 60 ns (6 ns) SMD simulation, the dsDNA molecule (ssDNA molecule) underwent a molecular extension of 53 Å (73 Å).

Self-Consistent Determination of Electric Potential

The electronic transport properties of the g-QPC depend on the induced electrostatic potential $\varphi(r)$ on the membrane due to the DNA charges in the nanopore. The local potential can be obtained self-consistently by solving the Poisson equation, $$\nabla \cdot [\varepsilon(r)\nabla \phi(r)] = -e[K^+(r) - Cl^-(r)] - \rho_{DNA}(r) \quad (1)$$

and using a Newton-multigrid method inside a 3D box containing the g-QPC in solution [19]. In eq. 1, e is the local permittivity, and the RHS includes the charge of ions in solution ($K^+$, $Cl^-$) as well as $\rho_{DNA}$, the DNA charges present in the system. The electrolyte distributions obey Boltzmann statistics [6]

$$K^+(r) = c_0 \exp\left[-\frac{e\phi(r)}{k_B T}\right], \quad (2)$$

$$Cl^-(r) = c_0 \exp\left[\frac{e\phi(r)}{k_B T}\right]$$

Here, $K^+$ and $Cl^-$ are the local electrolyte concentrations, where $c_0$ is the nominal concentration of the solution. A typical translocation bias across the membrane is less than 0.5 V, a regime in which eq. 2 is valid [14]. A non-uniform 3D grid with 256 points in each dimension is used to discretize the system. The grid near the nanopore has a larger resolution to improve accuracy in the electrostatic potential induced by the DNA. Neumann boundary conditions are enforced on the sides of the box, while Dirichlet boundary conditions are used for the top and bottom of the box ($V_{TOP} = V_{BOTTOM} = 0$ V).

Electronic Transport Properties of Graphene Nanoribbons

The fluctuations of the potential $\varphi(r)$, induced by DNA translocation as obtained from eq. 1, are used to calculate the transport properties of the g-QPC within the tight-binding approximation, for which the Hamiltonian reads [8, 34]

$$H = \sum_{i,\mu} [\epsilon_\mu - e\phi(r_i)]a_i^{\mu\dagger}a_i^\mu + \sum_{\langle ij \rangle \atop \mu\nu} V_{\mu\nu}(\vec{n})a_i^{\mu\dagger}b_j^\nu + V_{\nu\mu}(\vec{n})b_j^{\nu\dagger}a_i^\mu \quad (3)$$

Here, $e_\mu$ is the on-site energy of an electron in state $\mu$ located at position i, $\varphi(r_i)$ is the electrostatic potential at position i, and $a_i^{\mu\dagger}/b_i^{\mu\dagger}$ and $a_i^\mu/b_i^\mu$ are creation and annihilation operators for an electron in state $\mu$ at position i for the graphene A/B sub-lattice, respectively. The states $\mu$, $\nu$ are the $p_z$, $d_{yz}$, and $d_{zx}$ orbitals of atomic carbon [35]. The inclusion of the d states in the basis improves the description of the electronic structure by allowing for the inclusion of edge-passivation by hydrogen. The transfer integrals V(n), where n is the unit displacement between positions i and j, are determined by fitting to ab initio calculations [35]. All tight-binding parameters are taken from Boykin et al [34].

After determining the Hamiltonian, the electronic properties of the g-QPC are obtained using the non-equilibrium Green's functions (NEGF) formalism. The Green's function G is written $$G(E) = [E - H]^{-1} \quad (4)$$

In real space, it is written $$[E \pm i\eta - H(r,r')]G(r,r') = \delta(r - r') \quad (5)$$

H is the Hamiltonian, and $\eta$ is an infinitesimally small number to ensure solutions are found. One can divide the g-QPC lattice into three sections, two leads (L) on either side of a conductor (C). Then, eq. 4 can be written $$\begin{bmatrix} G_L & G_{LC} & 0 \\ G_{CL} & G_C & G_{LC} \\ 0 & G_{CL} & G_L \end{bmatrix} = \begin{bmatrix} E - H_L & V_{LC} & 0 \\ V_{CL} & E - H_C & V_{LC} \\ 0 & V_{CL} & E - H_L \end{bmatrix}^{-1} \quad (6)$$

Taking $V_{LC} = V_{CL}^\dagger$ yields $$G_C = \left[(E + i\eta)I - H_C - \sum_\alpha \Sigma_\alpha\right]^{-1} \quad (7)$$

where $\Sigma_\alpha \equiv V_{\alpha C}^\dagger [E - H_\alpha]^{-1} V_{\alpha C}$ is the "self energy" of lead $\alpha$.

The transmission $\bar{T}(E)$ between the leads 1 and 2 is given by [36]

$$\bar{T}_{12} = -T_r[(\Sigma_1 - \Sigma_1^\dagger) G_C (\Sigma_2 - \Sigma_2^\dagger) G_C^\dagger]. \quad (8)$$

and is used to find the conductance at a source-drain bias $V_{DS}$ $$G = \frac{2e}{V_{DS} h} \int_{-\infty}^{\infty} \bar{T}(E)[f_1(E) - f_2(E)] dE \quad (9)$$

Here, $f_\alpha(E) = f(E - \mu_\alpha)$ is the probability of an electron occupying a state at energy E in the lead $\alpha$, and $(\mu_1 - \mu_2)/e = V_{DS}$ is the bias across the conductor. We take f(E) as the Fermi-Dirac distribution function and the temperature as 295 K. The Fermi energy $E_F$ is set equal to $\mu_1$. In practice, $E_F$ can be adjusted by an external gate bias as proposed in a previous work [22]. In this analysis, it is taken to be an external parameter without any loss of generality.

Electronic Detection of dsDNA Helicity

Figures 15A, 15B:
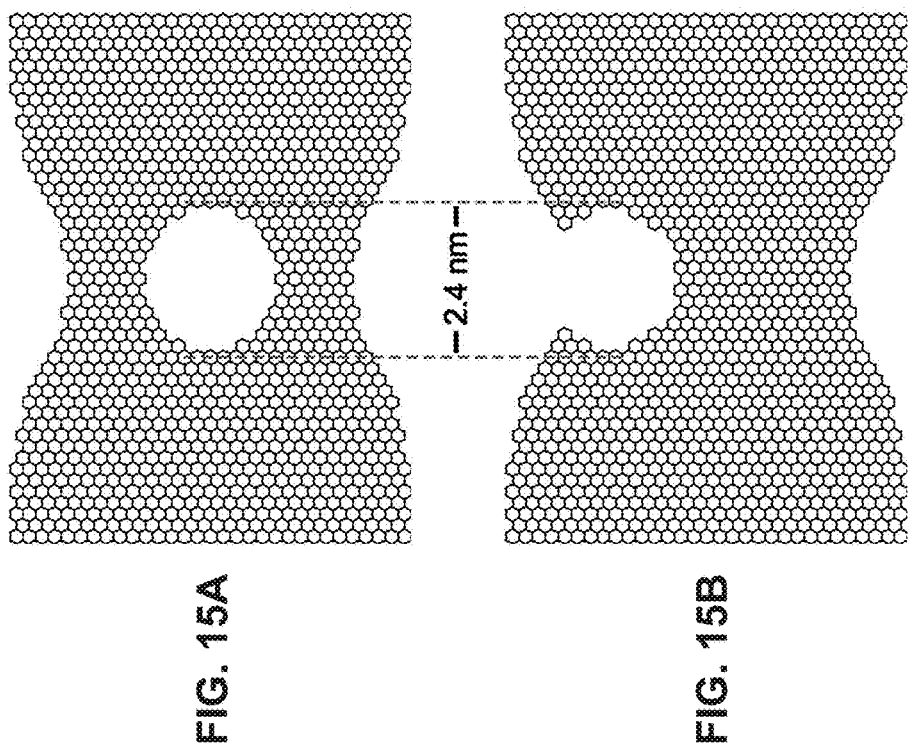
FIG. 15A depicts a lattice of a 5 nm g-QPC with a 2.4 nm diameter centered nanopore (g-QPCa)
FIG. 15B depicts a lattice of a 2.4 nm diameter edge nanopore (g-QPCb)
Figure 16:
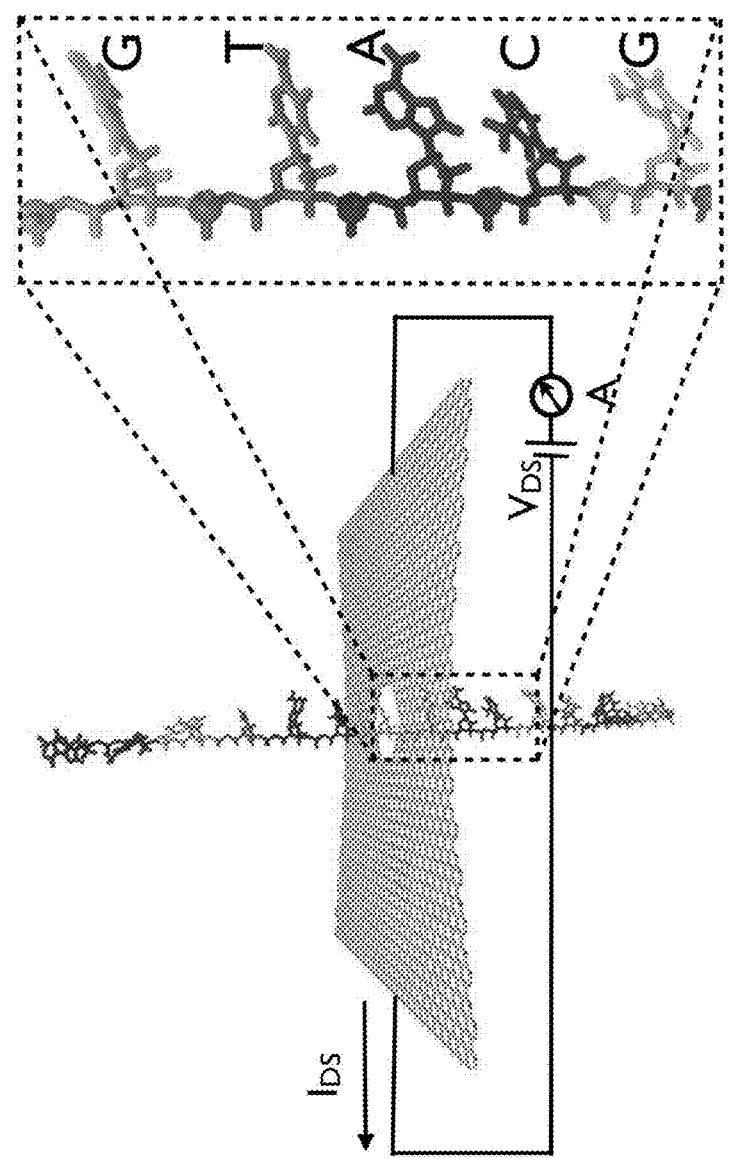
FIG. 16 depicts a schematic of the g-QPC system used to calculate transverse electronic conductance. Shown in the figure is an ssDNA, which arose from a MD simulation of forced extension, being translocated through the nanopore under a translocation bias. Transverse electronic conductance was computed for the five base pairs shown in the inset of the figure.

In the subject disclosure, we consider g-QPCs with leads measuring ~8 nm wide and a constriction measuring ~5 nm wide (FIGS. 15A-15B). Each g-QPC has a 2.4 nm diameter nanopore located in one of two positions: the geometric center of the g-QPC (FIG. 15A) or vertically offset (y direction) from the geometric center (FIG. 15B). A schematic diagram of a DNA molecule electrophoretically translocating across the g-QPC membrane through a nanopore is shown in FIG. 16.

The charge distributions from an ideal 24 base pair B type dsDNA, containing only adeninie and thymine base pairs, in a 1 M KCl solution were translocated through the nanopores of the described g-QPCs. The corresponding potential distributions in the plane of the graphene membrane were obtained as outlined in eq. 1.

At the start of the translocation (snapshot 0), the bottom of the strand is at a distance 3.5 Å above the g-QPC membrane, and the translocation axis of the dsDNA is coaxial with the center of the nanopore. The dsDNA is then rigidly translocated 0.25 Å per time step (snapshot) through the nanopore until the DNA has passed through the pore completely. After the last snapshot, the top of the DNA strand is 13.5 Å below the g-QPC membrane. The charge distribution arising from the dsDNA at each snapshot is fed into the Poisson solver, yielding the electrostatic potential on the g-QPC membrane at each time step.

Because of the heavy screening due to the electrolytic ions in solution, the potential on the g-QPC membrane is mainly induced by the charges in the immediate vicinity of the nanopore. As a result, the charge distribution inside the pore is effectively due to a thin slice of the DNA strand located within the membrane plane. In effect, the electrostatic potential "rotates" in-place (see e.g. [19]). Since each slice of the DNA strand has a reflection symmetry, the resulting potential should also have the same symmetry.

FIGS. 17A-17G show the conductance in the g-QPC during the translocation of the dsDNA while the g-QPC is gate biased so as to achieve three different carrier concentrations: $p_1 \approx 7 \times 10^{12}$ cm$^{-2}$ ($E_F = -0.25$ eV), $p_2 \approx 1 \times 10^{12}$ cm$^{-2}$ ($E_F = 0$ eV), and $n_1 \approx 4 \times 10^{12}$ cm$^{-2}$ ($E_F = 0.25$ eV). The g-QPC geometries considered had the nanopore in one of two positions, the first of which is located in the center of the g-QPC (g-QPCa) (FIG. 15A). As seen in FIG. 17A, for $p = p_1$, the average conductance $\overline{G}$ was found to be ~15 µS, and the conductance variations dG have a magnitude of less than 0.1 µS, which is <1% of $\overline{G}$. As the hole concentration is reduced to $p_2$, $\overline{G}$ jumps to ~26 µS, while dG similarly increases to ~1.4 µS, or more than 5% of $\overline{G}$. Finally, for the n-type concentration $n_1$, $\overline{G} \approx 9$ µS, while the dG$\approx 0.5$ µS, or 6% of $\overline{G}$. Though the conductance is indeed smaller, the variations dG increase relative to the overall signal The significant change in both conductance magnitude and magnitude variation dG are due to the complex boundary conditions introduced by the QPC and nanopore edge. These boundary conditions give rise to a non-uniform electron density around the nanopore, which changes as the carrier concentration is adjusted by the gate bias. The DNA, then, interacts differently with the electron (and hole) density at different carrier concentrations, as well as at different points during the translocation through the pore, eliciting a marked difference in the behavior of the conductance. As a result, small gate voltage adjustments can cause significant improvements in the ability to identify the DNA signal from the background. Additionally, it is worth noticing that though changes in carrier concentrations can largely reduce the magnitude of the conductance signal, as seen when switching from p-type ($p_2$) to n-type ($n_1$), the variations dG can actually increase with respect to the overall signal, enhancing the detection of the DNA helix.

In the case of g-QPCb (FIG. 15B), when the pore is positioned 2 nm above the location of the center of the GNR constriction, the behavior of the mean conductance $\overline{G}$ is significantly different from the conductance behavior of g-QPCa. For $p_1$, $\overline{G}$ is ~91 µS, about six times the conductance of g-QPCa at the same concentration, while dG$\approx 1.1$ µS, less than 2% of the signal. When p is changed to $p_2$, $\overline{G}$ drops to ~27 µS, in contrast to the conductance increase in g-QPCa for the same carrier concentration change. The variations dG are only ~0.3 µS, which is negligible when compared to the signal magnitude. For the n-type GNR ($E_F = 0.25$ eV), $\overline{G}$ drops even further to ~16 µS, but dG increases to 1.4 µS, or 9% of the signal. This different behavior of G at the same values of n is another consequence of the complex boundary conditions of the QPC edge and nanopore. In particular, moving the pore around the QPC center changes the sign of the differential transconductance for the p-type g-QPCs. However, the conductance behavior of g-QPCb is similar to that of g-QPCa in the sense that small changes in carrier concentration can cause significant modulation of $\overline{G}$ and dG. A more in-depth discussion on the interaction of the boundary and electronic properties of the g-QPC can be found elsewhere [19, 22]

For all carrier concentrations and nanopore positions, the conductance traces display a periodic behavior, repeating after a period of ~130 snapshots, as a consequence of helical nature of the dsDNA itself. The electrostatic potential rotation converges to its original position after one full helical pitch has translocated, which for 130 snapshots at 0.25 Å per snapshot yields a distance of ~3.3 nm for the DNA pitch. In addition, the initial and final halves of each period are related by a mirror symmetry, as shown in FIGS. 17A-17G. The g-QPC lattice's y-axis reflection symmetry, coupled with the DNA molecule's own reflection symmetry, yields an identical conductance after the DNA potential is reflected about the y-axis, or when $\theta$ is transformed to $2\pi - \theta$ (FIG. 17G). In other words, potentials at an angle $\theta$ yield the same conductance for potentials at angles $2\pi - \theta$. The mirror effect within each period is present in all conductance curves.

Detection of Helical to Zipper Conformational Transformation

Another potential application of the g-QPC as a biomolecular sensor is the detection of the conformational changes DNA undergoes inside the nanopore. A poly(AT)$_{15}$ dsDNA molecule was stretched using SMD simulations to achieve forced extension of the DNA molecule. SMD simulations were performed by harmonically restraining both 3' and 5' terminal phosphate atoms on one end, while the corresponding atoms at the other end were pulled at a constant velocity of 1 Å/ns. The length of the dsDNA molecule changed from 52 Å to 103 Å over the course of a 60 ns SMD simulation. The dsDNA undergoes a series of conformational changes, starting in the helical form (B-DNA) and gradually unwinding into a planar zipper-like form (zip-DNA). In the zip-DNA conformation, the hydrogen bonds on the complementary base pairs are broken, and the base pairs interlock in a zipper-like fashion. The conformations of both dsDNA type can be seen in FIG. 18A. The transformation between the helical and zipper conformations of the dsDNA molecule can be detected by the g-QPC device by calculating the transverse electronic conductance of the graphene membrane [37]. Each conformation was rigidly translocated (translocated at a rate of 0.5 Å per snapshot) through the nanopores in both g-QPCa and g-QPCb at $p=p_2$ over a series of snapshots, and the electrostatic potential from the DNA charges was calculated for each snapshot.

Figure 18C:
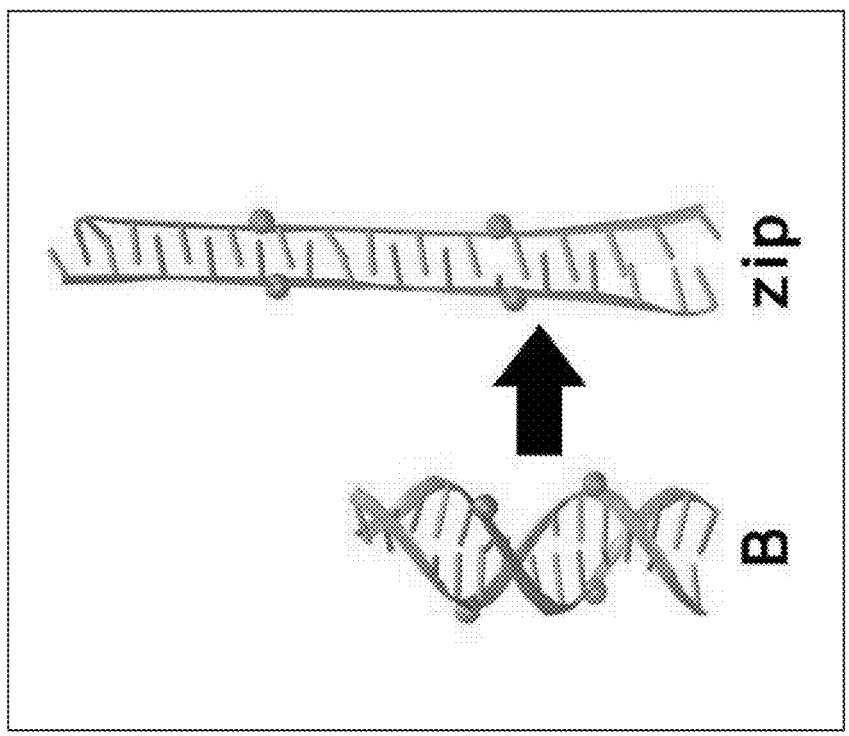

FIG. 18B shows the conductance in g-QPCa as a function of the electrostatic potential of each snapshot. When the dsDNA is helical in shape, the proximity of the DNA charges to the nanopore edge generates significant potential variations on the g-QPC membrane, and as described earlier, the electrostatic potential induced by the DNA charge effectively rotates in the plane of the membrane. As a result, the conductance variation dG is ~0.8 μS, or 9% of the mean conductance $\overline{G} \approx 9$ μS. On the other hand, when the dsDNA is in the zip-type, its cross-sectional area becomes smaller than that of B-DNA, resulting in a greater distance between the DNA charge and the nanopore edge. Thus, the electrolyte (Debye length ~3 Å) screens the electrostatic potential on the nanopore edge significantly. In addition, because the zip-type DNA is no longer helical, the membrane potential does not vary significantly as the DNA translocates. As a result dG vanishes, and the signal is virtually constant at $\overline{G} = 9.2$ μS. When the dsDNA is pulled through g-QPCb, a similar behavior occurs. Hence, in B conformation, dG is 1.2 μS, i.e. ~8% of $\overline{G} = 16$ μS. In the zip conformation, on the other hand, the conductance G is flat at a constant value of 16.2 μS.

Our simulations indicate that the g-QPC can clearly differentiate between the two types of DNA. At both pore positions, the change from a significant conductance variation of ~8-9% of the signal to a constant value can be readily observed. In addition, moving the nanopore position in a g-QPC can enhance the value of the conductance, as well as the variation amplitude, especially when combined with a tunable gate electrode. An interesting point to note is the gating effect of the DNA strand itself on the g-QPC. Because of the DNA's proximity to the nanopore edge in the B-DNA conformation, its electrical charges actually bias the constriction, inducing a different mean conductance, which is an additional confirmation the transformation has occurred.

Electronic Detection of ssDNA Nucleotide Translocation

We also use SMD to stretch a 16 base pair ssDNA, comprising of 4 repetitions of the DNA segment A-T-G-C, from a canonical helical conformation to a linear, ladder-like form. The ssDNA molecule was solvated in a 0.3 M KCl electrolyte solution, and the terminal phosphate atom on the 5' end of the ssDNA was pulled with a constant velocity of 10 Å/ns. The terminal phosphate atom on the 3' end of the DNA was harmonically constrained to its initial position, until the nucleotides in the central region of the ssDNA acquired a linear conformation. The molecular length of the ssDNA changed from 55 Å to 128 Å over the course of the simulation, and the base pairs collectively tilted towards the 5' end of the DNA [38].

The stretched ssDNA, which adopts a linear configuration due to forced extension, was placed inside a nanopore within a g-QPC and translocated at a rate of 1 Å per snapshot along a direction perpendicular to the graphene plane to mimic electrophoretic translocation of the DNA through the graphene nanopore (see FIG. 16). As mentioned earlier, we showed that the rotation of the electrical potential of the DNA charge distribution, arising from DNA helicity, within the graphene plane causes a modulation in the electronic conductance through the graphene membrane. In the present study, we choose a ladder-like conformation for ssDNA to ensure that the conductance modulations are solely due to the linear translocation of the DNA as opposed to any effective rotation of the electrostatic potential in the graphene plane.

First, we investigate the ssDNA translocation through a circular nanopore with a 1.2 nm diameter at three different locations in the g-QPC at a carrier concentration $p=p_2$. FIGS. 19A-19D show the transverse electronic conductance of the g-QPC as a function of ssDNA snapshot. We consider two orientations of the DNA molecule, one where the base pairs are aligned in the direction of transverse electronic current, herein referred to as ssDNA-x (see FIG. 19D), and the second where the base pairs are aligned in the direction perpendicular to the transverse electronic currents, herein referred to as ssDNA-y (see FIG. 19D).

Figures 19A, 19B, 19C:
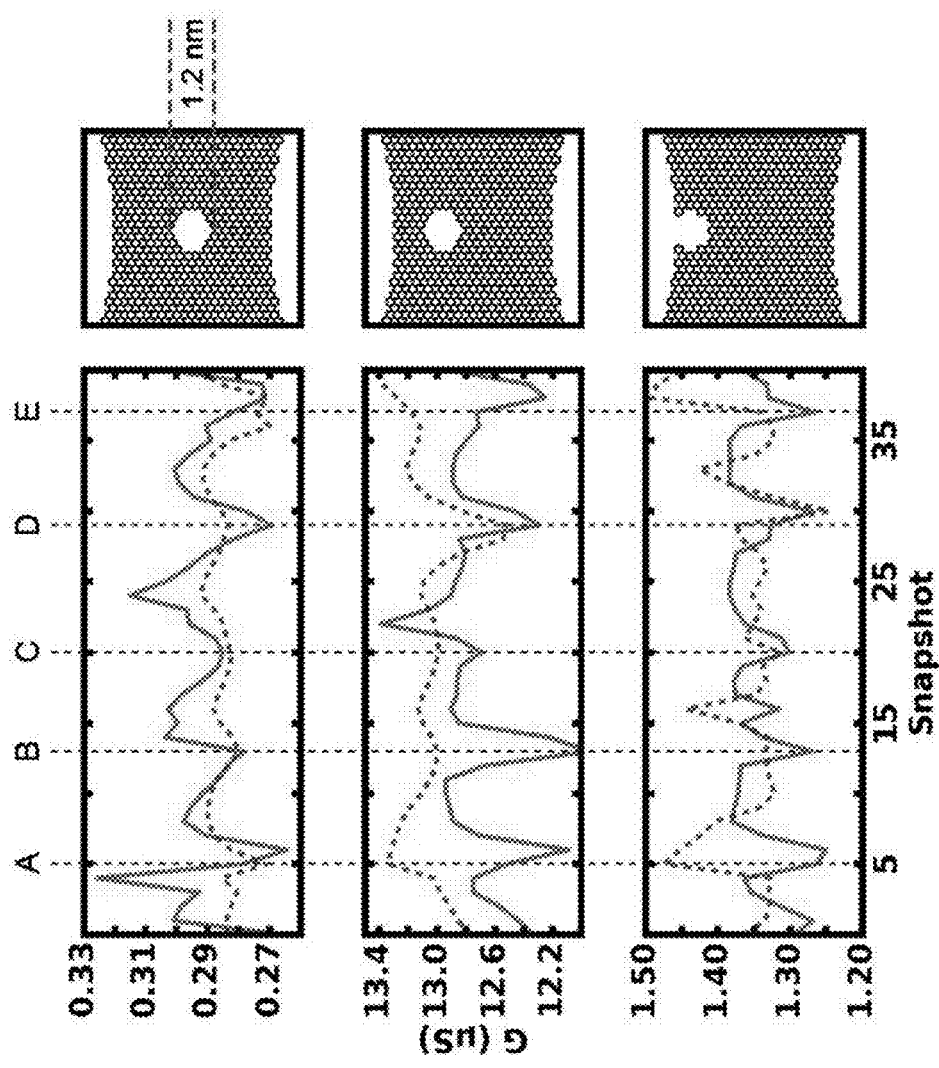
FIGS. 19A, 19B, 19C and 19D depict a conductance as a function of DNA position (snapshot) arising in a g-QPC due to translocation of 5 base pairs of a ssDNA molecule in a linear ladder-like conformation (see inset FIG. 16). The dips in the conductance correspond to the translocation of a single base pair through the nanopore. Three different 1.2 nm diameter nanopore geometries are investigated: the nanopore center is (a) aligned to the geometric center of the graphene membrane, (b) offset by 1 nm from the geometric center, and (c) offset by 2 nm from the geometric center. (d) A schematic of the g-QPC nanopore with ssDNA inside. For each of the geometries the base pairs were translocated in two different configurations: ssDNA-x, where the base pairs are aligned in the direction of transverse electronic current (x direction) and ssDNA-y where the base pairs are aligned in direction perpendicular to the transverse electronic currents (y direction)
Figure 19D:
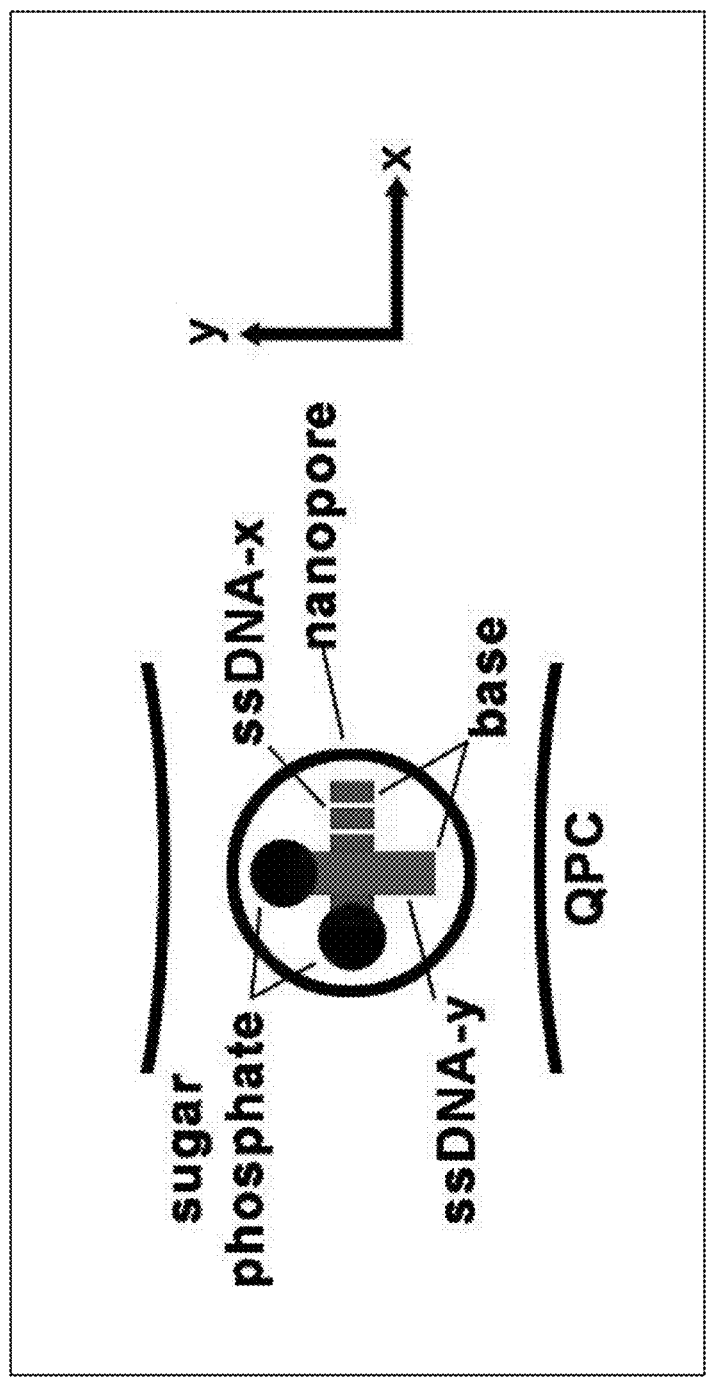

FIG. 19A displays the conductance traces for the center of the nanopore aligned to the geometric center of the g-QPC. For both DNA orientations, the conductance displays a series of peaks and valleys corresponding to the passage across the graphene membrane of individual nucleotides attached to the negatively charged phosphate backbone. The variation in electrical potential on the nanopore edge due to the motion of charges on the DNA molecule during the translocation process induces a variation of the local carrier concentration along the edge of the graphene nanopore, altering its conductance [19]. The particular snapshot when a nucleotide's center of mass passes the graphene membrane is denoted with a vertical black dashed line in FIGS. 19A-19C. As can be readily seen, these snapshot locations correlate with the valleys in the conductance curve, identifying a conductance valley with the passage of a single nucleotide. The magnitude of the conductance at a particular snapshot is determined by the spatial orientation of the nucleotide within the nanopore, which can fluctuate significantly. However, the percentage change in conductance between nucleotides can be in excess of 15%, indicating the possibility to distinguish the charges of a passing nucleotide from the rest of the system.

In particular, the magnitude of the conductance variations for ssDNA-y is ~0.03 μS to ~0.05 μS, or 10 to 17% of the overall signal. These variations are approximately three times larger than those for ssDNA-x for two reasons. First, there is a larger electronic density of states in g-QPCa above and below the nanopore (along the y-direction) compared to the density of states on either side (x-direction). Secondly, the nucleotides of ssDNA-y are closer to the larger electron density compared to ssDNA-x. As a result, changes in electrical potential have a more significant effect on the conductance.

When the pore geometry is altered, such as when changing its position, shape, or size, the boundary conditions restricting the allowed electronic states in the QPC are likewise changed, so various conduction channels around the Fermi energy may open or close. Depending on the transmission probability of each of these channels, an overall larger or smaller current can arise. An in-depth discussion on the effects of geometry on the electronic states and electronic transmission is reported in [19].

In order to determine the effect of the pore position on the conductance sensitivity, we chose to study g-QPCs with a 1.2 nm diameter pore in two alternate positions, shown in FIGS. 19B-19C, where the nanopore center is offset from the QPC geometric center by 1 nm and 2 nm, respectively, along the y-direction defined in FIGS. 19A-19C. Because the trajectory of ssDNA remains unchanged for each pore position, the conductance of the QPC with a pore at position 'b' (FIG. 16) has conductance minima at the same nucleotide positions as that with the pore at 'a' (FIG. 19A). However, for ssDNA-y, the width of these variations is noticeably smaller. Similarly, for ssDNA-y, the width of the minima is further reduced for a QPC with a pore at position 'c' (FIG. 19C). This is because there is a smaller interaction between the charges on the DNA backbone and the GNR electronic conduction states as the pore is placed closer to the edge. The negative backbone charges tend to attract positive holes in the g-QPC, enhancing the hole conduction and masking the nucleotide signal. As the nanopore is placed closer to the edge, however, the influence of the backbone becomes negligible, especially when the backbone is outside of the g-QPC, as in the case of pore 'c' (FIG. 19C). As a result, the nucleotide charges are solely responsible for the conductance variation, enhancing the detection of the nucleotide passage event.

In the case of the ssDNA-x, as the pore is placed closer to the edge, the nucleotide signal becomes indiscernible. The nucleotide and the conducting holes of the GNR are too far to interact strongly, when the nanopore is far from the QPC center, and cannot to be detected. On the other hand, in the ssDNA-y orientation, the nucleotides are adjacent to the conduction charges, and the conductance dips can be clearly seen.

The most striking effect of the changing boundary conditions when varying the pore position is their influence on the conductance magnitude. When the pore is moved from the nanopore center 'a' to position 'b', the conductance is amplified by almost two orders of magnitude, while at position 'c', the conductance is reduced by a factor of ~10. Such drastic changes in the conductance magnitude with alternate pore positions suggest that the conductance magnitude is a strong function of lattice geometry. However, finer control of the conductance magnitude can be achieved by adjusting electronic carrier concentration in the g-QPC via a gate electrode [22]. It is clear that positioning the pore closer to the boundary negates the influence of the phosphate backbone on the conductance, and hence increases the ability for the current to detect only the nucleotide.

Figures 20A, 20B, 20C:
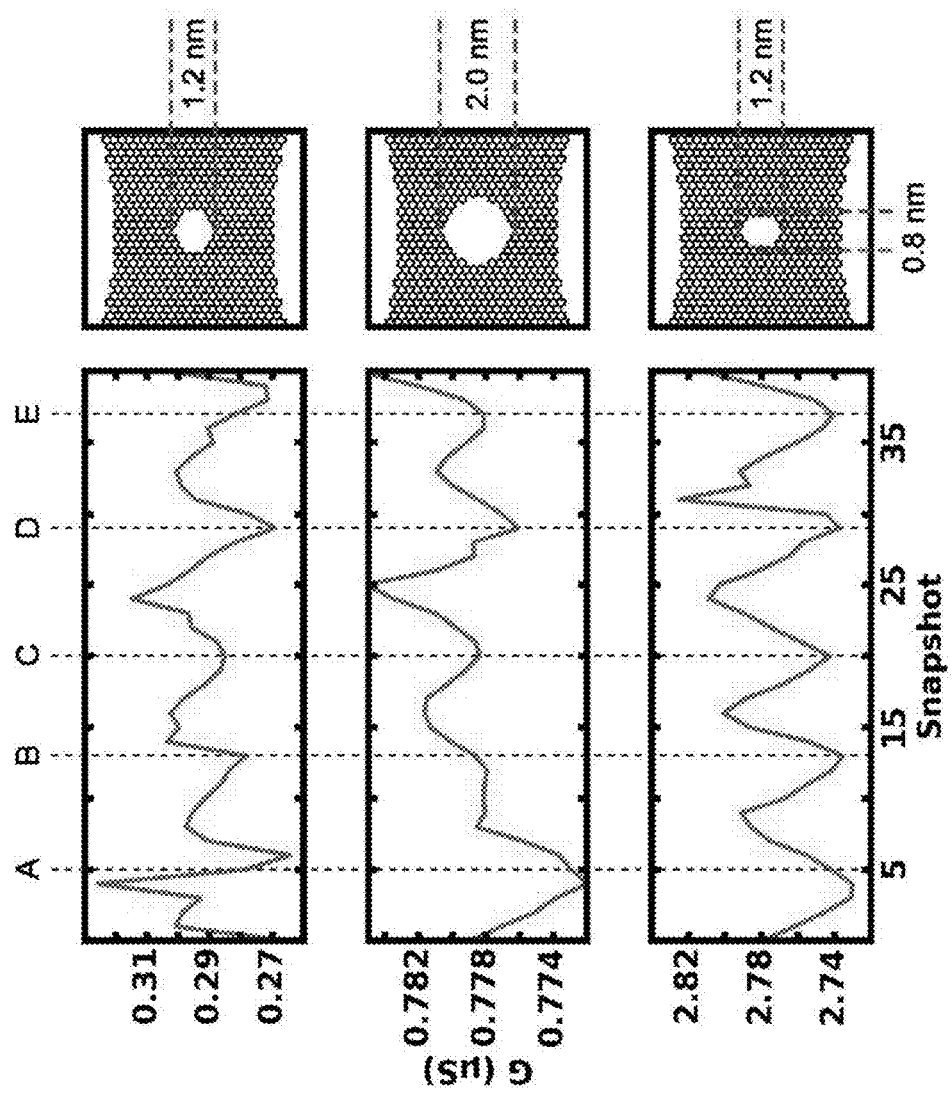
FIGS. 20A, 20B and 20C depict an influence of pore size and shape on the electronic conductance variation due to translocation of a 5 base pair long ssDNA segment in a linear ladder-like conformation. (a) circular pore with diameter=1.2 nm, (b) circular pore with diameter=2 nm, and (c) elliptical pore with major and minor axis diameters equal to 1.2 nm and 0.8 nm respectively.

In FIGS. 20A-20C we display the conductance variation due to ssDNA-y, for a 2 nm circular pore (FIG. 20B), and a 0.8 nm by 1.2 nm elliptical pore at the g-QPC center (FIG. 20C), in addition to the 1.2 nm circular pore (FIG. 20A) discussed earlier. The primary result of increasing the circular pore diameter to 2 nm is the suppression of the interaction between the ssDNA molecule and the electronic conduction states (FIG. 20B). Since the ssDNA is in the center of the pore, the electrolytic screening, with a Debye length of 0.5 nm, causes the electric potential to become significantly smaller at the pore edge. Variations can still be seen at the same locations as the 1.2 nm pore, but they are significantly smaller, varying in magnitude by 1%.

One of the main issues encountered when electrically sensing a DNA molecule, translocating through a nanopore, is the stochastic fluctuations of the DNA molecule itself, disrupting the conductance variations due to the passage of a nucleotide. Employing an elliptical pore can restrict the lateral fluctuations of translocating base pair. For this purpose we analyze the conductance due to ssDNA-y translocating in an elliptical pore with a major and minor axis diameter equal to 1.2 nm and 0.8 nm respectively (FIG. 20C). As can be seen, the conductance variations become much more uniform and well defined when the ssDNA-y is translocating through the elliptical pore. The pore edge is screened less by the electrolyte, because the phosphate backbone of the DNA is closer to the pore atoms. As a result, the conductance signal reflects the passage of the phosphate atoms more than the nucleotides themselves. The conductance variations are still significant, having a magnitude 3% of the overall conductance.

The foregoing subject disclosure outlines a comprehensive methodology for simulating a g-QPC device for the purpose of biomolecular detection and characterization for a variety of potential medical and health applications, particularly DNA identification and genome sequencing. The proposed device is capable of sensing the motion and rotational position of dsDNA and ssDNA translocating through a nanopore, the conformational changes of a dsDNA molecule under forced extension, and the passage of single nucleotides across the graphene membrane. The pore geometry, position, and size, when combined with a variable carrier concentration, play crucial roles in the sensitivity of the device to the potential induced on the membrane by the translocating molecules.

The applications of this device are not limited to those outlined in this study. For example, detection of methylated cytosine can be an early indication of particular cancers. Additionally, our method is general enough to analyze the structure of other biomolecules. In this context, many biomolecules, particularly proteins, undergo structural transformations depending on the environment, so the ability to quickly and easily characterize their structures is of fundamental interest. Furthermore, experimental nanopores can be used to investigate single molecule conformation by force spectroscopy. For instance, when a DNA molecule is stretched inside a nanopore, the DNA molecule undergoes structural conformation. Being able to detect such conformational changes electronically, as well as the ability to correlate them with measured ionic currents and force experienced by the DNA, could make nanopores more attractive in force spectroscopy measurements.

Presently, differentiating individual nucleotides from one another is a large obstacle facing this class of device. Future avenues for investigation involve the addition of control gates in a multilayer stack containing the g-QPC to adjust the position and speed of any translocating molecules, reducing stochastic fluctuations and thereby enhancing the conductance signal [19]. Statistical analysis on large data sets can also be employed to further improve the identification of nucleotides from one another.

References Cited in the Disclosure Below
1. Taber, K. A. J.; Dickinson, B. D.; Wilson, M. The promise and challenges of next-generation genome sequencing for clinical care. *JAMA Intern. Med.* 2014, 174, 275-280.
2. Schadt, E. E.; Turner, S.; Kasarskis, A. A window into third-generation sequencing. *Hum. Mol. Gen.* 2010, 19, R227-R240.
3. Branton, D.; Deamer, D. W.; Marziali, A.; Bayley, H.; Benner, S. A.; Butler, T.; Di Ventra, M.; Garaj, S.; Hibbs, A.; Huang, X. et al. The potential and challenges of nanopore sequencing. *Nat. Biotechnol.* 2008, 26, 1146-1153.
4. Venkatesan, B. M.; Bashir, R. Nanopore Sensors for Nucleic Acid Analysis. *Nature Nanotech.* 2011, 6, 615-624.
5. Schloss, J. A. How to get genomes at one ten-thousandth the cost. *Nat. Biotechnol.* 2008, 26, 1113.
6. Howorka, S.; Siwy, Z. Nanopore analytics: sensing of single molecules. *Chem. Soc. Rev.* 2009, 38, 2360-2384.
7. Marshall, M. M.; Ruzicka, J.; Zahid, O. K.; Taylor, E. W.; Henrich, V. C.; Hall, A. R. Solid-State Nanopore Characterization of Single-Strand DNA-SSB Interactions. *Biophys. J.* 2015, 108, 331a.

8. Xie, P.; Xiong, Q.; Fang, Y.; Qing, Q.; Lieber, C. M. Local electrical potential detection of DNA by nanowire-nanopore sensors. *Nature Nanotech.* 2012, 7, 119-125.
9. Gracheva, M. E.; Vidal, J.; Leburton, J.-P. p-n Semiconductor Membrane for Electrically Tunable Ion Current Rectification and Filtering. *Nano Lett.* 2007, 7, 1717-1722.
10. Gracheva, M. E.; Xiong, A.; Aksimentiev, A.; Schulten, K.; Timp, G.; Leburton, J.-P. Simulation of the Electric Response of DNA Translocation through a Semiconductor Nanopore-Capacitor. *Nanotechnology* 2006, 17, 622-633.
11. Li, J.; Gershow, M.; Stein, D.; Brandin, E.; Golovchenko, J. DNA molecules and configurations in a solid-state nanopore microscope. *Nat. Mater.* 2003, 2, 611-615.
12. Sathe, C.; Zou, X.; Leburton, J.-P.; Schulten, K. Computational investigation of DNA detection using graphene nanopores. *ACS Nano* 2011, 5, 8842-8851.
13. Skinner, G. M.; van den Hout, M.; Broekmans, O.; Dekker, C.; Dekker, N. H. Distinguishing Single- and Double-Stranded Nucleic Acid Molecules Using Solid-State Nanopores. *Nano Lett.* 2009, 9, 2953-2960.
14. Dekker, C. Solid-state nanopores. *Nature Nanotech.* 2007, 2, 209-215.
15. Wanunu, M.; Sutin, J.; McNally, B.; Chow, A.; Meller, A. DNA Translocation Governed by Interactions with Solid-State Nanopores. *Biophys. J.* 2008, 95, 4716-4725.
16. Schneider, G. F.; Kowalczyk, S. W.; Calado, V. E.; Pandraud, G.; Zandbergen, H. W.; Vandersypen, L. M. K.; Dekker, C. DNA Translocation through Graphene Nanopores. *Nano Lett.* 2010, 3163-3167.
17. Merchant, C. A.; Healy, K.; Wanunu, M.; Ray, V.; Peterman, N.; Bartel, J.; Fischbein, M. D.; Venta, K.; Luo, Z.; Johnson, A. T. C. et al. DNA translocation through graphene nanopores. *Nano Lett.* 2010, 10, 2915-2921.
18. Garaj, S.; Hubbard, W.; Reina, A.; Kong, J.; Branton, D.; Golovchenko, J. A. Graphene as a subnanometer transelectrode membrane. *Nature* 2010, 467, 190-193.
19. Liu, K.; Feng, J.; Kis, A.; Radenovic, A. Atomically thin molybdenum disulfi nanopores with high sensitivity for DNA translocation. *ACS Nano* 2014, 8, 2504-2511.
20. Kasianowicz, J. J.; Brandin, E.; Branton, D.; Deamer, D. W. Characterization of Individual Polynucleotide Molecules Using a Membrane Channel. *Proc. Natl. Acad. Sci. USA* 1996, 93, 13770-13773.
21. Zwolak, M.; Ventra, M. D. Electronic Signature of DNA Nucleotides via Transverse Transport. *Nano Lett.* 2005, 5, 421-424.
22. Girdhar, A.; Sathe, C.; Schulten, K.; Leburton, J.-P. Graphene Quantum Point Contact Transistor for DNA Sensing. *Proc. Natl. Acad. Sci. USA* 2013, 110, 16748-16753.
23. Venkatesan, B. M.; Estrada, D.; Banerjee, S.; Jin, X.; Dorgan, V. E.; Bae, M.-H.; Aluru, N. R.; Pop, E.; Bashir, R. Stacked graphene-Al2O3 nanopore sensors for sensitive detection of DNA and DNA-protein complexes. *ACS Nano* 2011, 6, 441-450.
24. Girdhar, A.; Sathe, C.; Schulten, K.; Leburton, J.-P. Tunable graphene quantum point contact transistor for DNA detection and characterization. *Nanotechnology* 2015, 26, 134005.
25. Phillips, J. C.; Braun, R.; Wang, W.; Gumbart, J.; Tajkhorshid, E.; Villa, E.; Chipot, C.; Skeel, R. D.; Kale, L.; Schulten, K. Scalable Molecular Dynamics with NAMD. *J. Comp. Chem.* 2005, 26, 1781-1802.
26. Trottenberg, U.; Oosterlee, C. W.; Schuller, A. *Multigrid*; Academic press, 2000.
27. Briggs, W. L.; McCormick, S. F. *A multigrid tutorial*; Siam, 2000.
28. Press, W. H.; Teukolsky, S. A.; Vetterling, W. T.; Flannery, B. P. *Numerical Recipes in C (2Nd Ed.): The Art of Scientific Computing*; Cambridge University Press: New York, N.Y., USA, 1992.
29. Lu, X.-J.; Olson, W. K. 3DNA: a software package for the analysis, rebuilding and visualization of three-dimensional nucleic acid structures. *Nucleic Acids Res.* 2003, 31, 5108-5121.
30. Humphrey, W.; Dalke, A.; Schulten, K. VMD—Visual Molecular Dynamics. *J. Mol. Graphics* 1996, 14, 33-38.
31. MacKerell, Jr., A. D.; Bashford, D.; Bellott, M.; Dunbrack, Jr., R. L.; Evanseck, J. D.; Field, M. J.; Fischer, S.; Gao, J.; Guo, H.; Ha, S. et al. All-atom empirical potential for molecular modeling and dynamics studies of proteins. *J. Phys. Chem. B* 1998, 102, 3586-3616.
32. Jorgensen, W. L.; Chandrasekhar, J.; Madura, J. D.; Impey, R. W.; Klein, M. L. Comparison of simple potential functions for simulating liquid water. *J. Chem. Phys.* 1983, 79, 926-935.
33. Essmann, U.; Perera, L.; Berkowitz, M. L.; Darden, T.; Lee, H.; Pedersen, L. G. A smooth particle mesh Ewald method. *J. Chem. Phys.* 1995, 103, 8577-8593.
34. Feller, S. E.; Zhang, Y.; Pastor, R. W.; Brooks, B. R. Constant pressure molecular dynamics simulation: The Langevin piston method. *J. Chem. Phys.* 1995, 103, 4613-4621.

Control of biological molecule motions inside nanopores is highly desired for widespread applications in biomedical sensing. Among such applications is nanopore DNA sequencing, where DNA molecules are translocated through nanopores in an electric field. In this study, we investigate the behavior of a double-stranded DNA inside nanopores in an electrically biased metallic membrane, by using molecular dynamics simulations. The stabilization of DNA, namely a reduction in thermal fluctuations, is observed under positive bias voltages, while at negative voltages negligible stabilization happens. For positive biases the stabilization arises from the electrostatic attraction between the negatively charged DNA backbone and the positively charged pore surface. Simulations on a teardrop-shape pore show a transverse shift of DNA position toward the sharp end of the pore under positive bias voltages, suggesting the possibility to control DNA alignment inside nanopore through geometry shaping. The present findings open a feasible and efficient route to reduce thermal noise, and in turn, enhance signal-to-noise ratio in single-molecule nanopore sensing.

In the past two decades, fast and inexpensive genome sequencing has become a rapidly growing research area.[1-6] In this context DNA sequencing using solid-state nanopores (SSNs) holds high promise for genomic applications as a potentially cost-effective, rapid and scalable technology.[6-11] SSN devices are made of a thin membrane containing one or multiple nanometer-sized pores, through which DNA molecules are translocated under an electric field across the membrane.[12-19] The passing nucleotides in the DNA molecule interact with the membrane, enabling the detection, and potentially the identification of individual nucleotides. Typical detection methods include measuring ionic current blockades from DNA dwelling in the nanopore,[20] measuring electrostatic potential changes across a membrane capacitor caused by the passage of DNA charges,[10] and monitoring transverse tunneling currents flowing through nucleotides sandwiched between two membrane electrodes.[21]

Despite the many efforts, detecting a real-time discernible signal for each nucleotide in a DNA strand, when the molecule is translocated through SSNs, is still a challenging issue. One of the primary impediments is the low signal-to-noise ratio due to thermal fluctuations of DNA bases, ions and water inside SSNs. In particular, the noise from variations in DNA structural conformation inside a nanopore may offset the signal induced by each nucleotide, largely weakening the sensing ability of the nanopore device. Therefore, in order to ensure the effective operation of a nanopore device in biosensing applications, a scenario that can minimize the thermal fluctuations of biomolecules in SSNs is highly desirable A possible solution to this problem is the use of a multi-layered membrane transistor containing a motion-control electrode layer,[22] as shown in FIG. 21A, which shapes the electrostatic landscape in the nanopore to reduce the stochastic fluctuations of the interior biomolecules. To explore this possibility, we carried out computational studies that first self-consistently solve for the electrostatic potential arising from a biased metallic layer containing two types of nanopores, one with a cylindrical cross section and a second one with a teardrop shape. We then performed a series of molecular dynamics simulations to determine the effect of the electrostatic potential on DNA motions in the nanopore. The results show that DNA fluctuations can be reduced by positive voltage biases higher than 0.5 V, suggesting a promising strategy to stabilize DNA inside nanopores. The reduction of DNA fluctuations could lower the conformational noise in the nucleotide signal measured by a secondary sensing membrane layer, and in turn, improve nucleotide detection and identification.

We first consider a nanopore with a cylindrical cross-section and 2.4 nm diameter, within a biased motion-control electrode layer within a stacked membrane, as shown in FIG. 21A. In a typical device, the motion-control layer is metallic and isolated from the sensing membrane (e.g., graphene) by an oxide layer such as $SiO_2$[17] or $Al_2O_3$.[23] The control voltage of the layer, $V_C$, is varied from $-0.75$ V to $0.75$ V by applying Dirichlet boundary conditions to the biased layer, as described in Methods. The control voltage, as well as source ($V_S$) and drain ($V_D$) voltages across the sensing membrane, are set with respect to a common ground.[22]

Figure 21D:
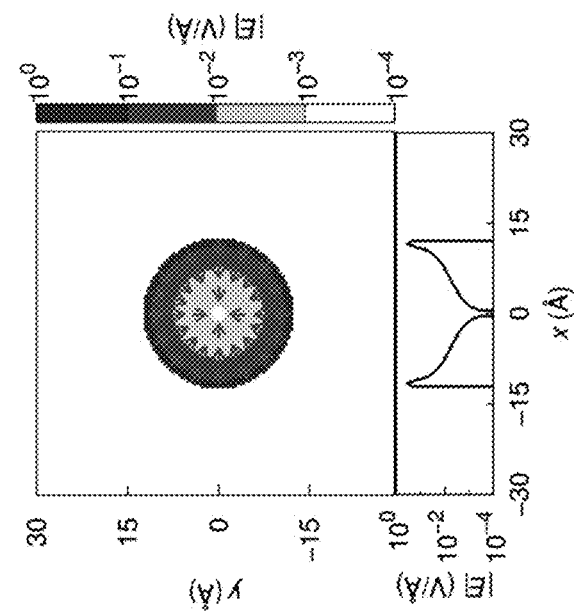
Figure 21C:
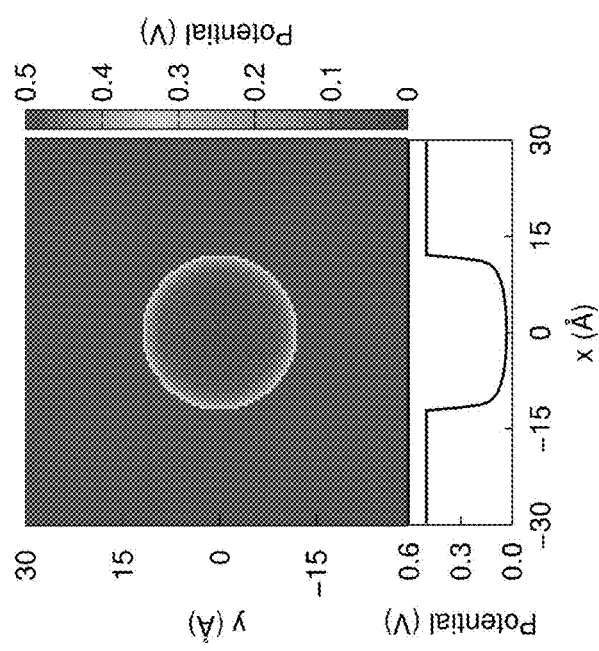

FIGS. 21C-21D show the electrostatic potential and the associated electric field in a plane perpendicular to the nanopore axis, respectively, at a biased voltage of $+0.5$ V. The potential is constant within the metallic interior, but drops rapidly after crossing the pore boundary, due to the large screening of $Cl^-$ ions that are attracted by the positively charged pore surface. The potential along a line through the center of the nanopore is shown at the bottom panel of FIG. 21C. The potential is nearly zero in most regions inside the pore, while a fast drop near the pore surface leads to a strong local electric field on the order of 0.1 V/Å (FIG. 21D). Besides, the local electric field at every point inside the pore points uniformly to the pore center (FIG. 21D). At negative electrode biases, the fields and potentials are identical in magnitude but opposite in sign to those for positive voltages.

Figures 22A, 22B:
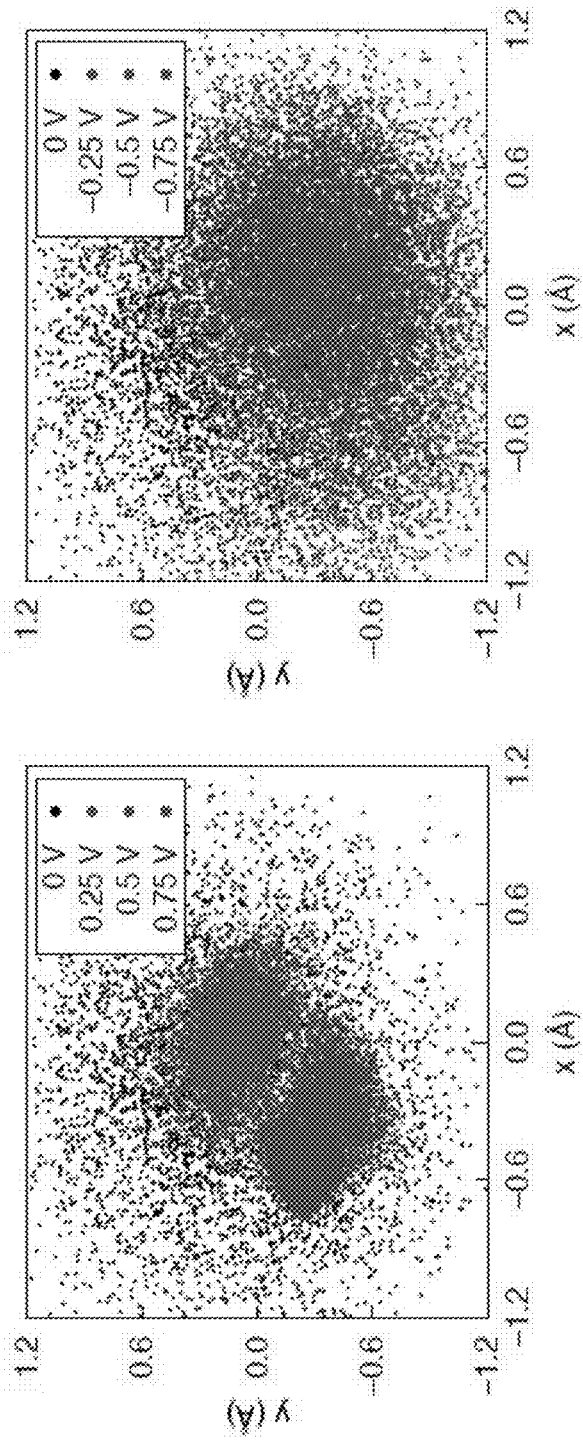
FIGS. 22A, 22B and 22C depict a scatter diagram showing center of mass positions of dsDNA in the simulation trajectory at (a) positive and (b) negative voltages. (c) Overlapped conformations of dsDNA in a 5 ns MD trajectory at 10 ps intervals under voltage biases of 0 (left), 0.5 (middle), −0.5 V (right)
Figure 22C:
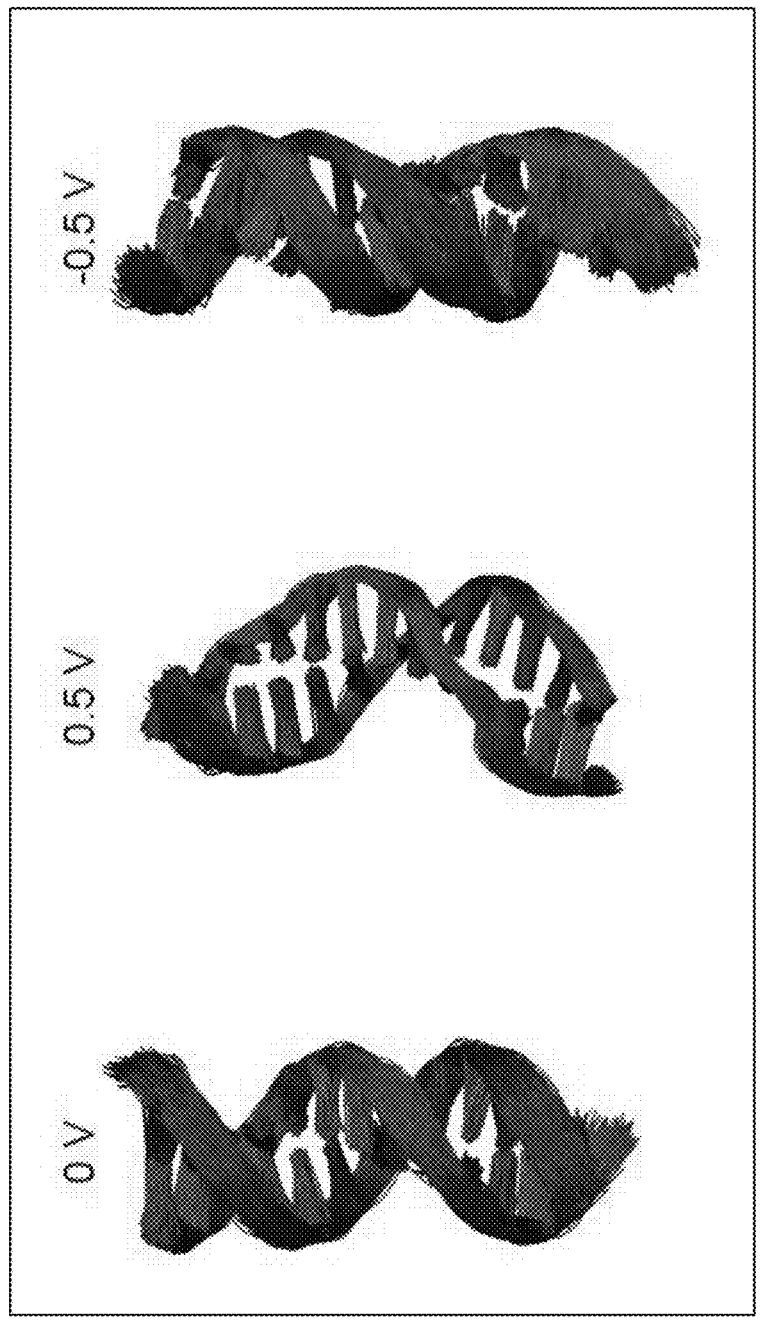

The calculated potential was then incorporated in MD simulations to determine its influence on the motion of a dsDNA molecule confined in the pore. In FIGS. 22A-22B, we show center of mass (CM) position of the DNA molecule in the xy-plane for each frame of the simulation trajectories at positive and negative voltages, respectively. At zero electrode bias, the DNA positions at different times spread almost uniformly around the center of the pore, as no significant interaction between pore and DNA atoms exists. At positive voltages (FIG. 22A), on the other hand, the DNA CM positions become more localized around a specific location in the pore, indicating damping of the DNA motion. This location is not exactly at the pore center because of the slight randomness in conformational change in response to applied voltages. The reduction of DNA fluctuations is discernible through the backbone spread in the overlapped DNA conformations obtained from the MD trajectory at 0.5 V (middle panel in FIG. 22C), which is seen to be thinner than that for the voltage-free case (left panel). Such a stabilization effect produced by positive voltages is the consequence of the attraction between the positively charged pore surface and the negatively charged DNA backbone. In addition, larger positive electrode voltages reduce the area within which the DNA CM is found (FIG. 22A), suggesting that larger voltages reduce the motion of the DNA molecule more strongly. At negative voltages, however, the DNA still fluctuates greatly, as indicated by the broad distribution of DNA CM positions (FIG. 22B) and the thicker backbone spread in the DNA conformations (right panel in FIG. 22C).

Figures 23A, 23B:
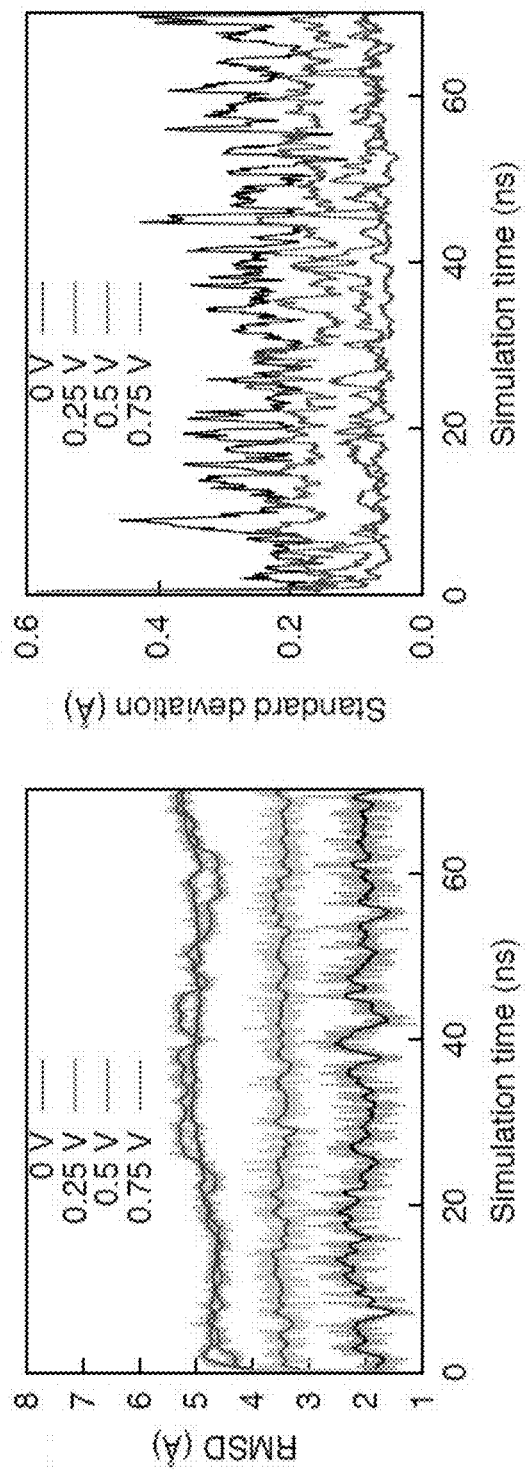
FIGS. 23A, 23B, 23C and 23D depict (a,c) RMSDs of all non-hydrogen atoms of the central portion of the dsDNA, namely nucleotides between the 6th and 17th base-pair of the 22 base-pairs, from the starting DNA conformation in MD simulations at positive (a) and negative (c) biased voltages. The thick lines represent moving average over 100 data points. (b,d) Moving standard deviation over 100 data points of RMSD for positive (b) and negative (d) voltages.
Figure 23D:
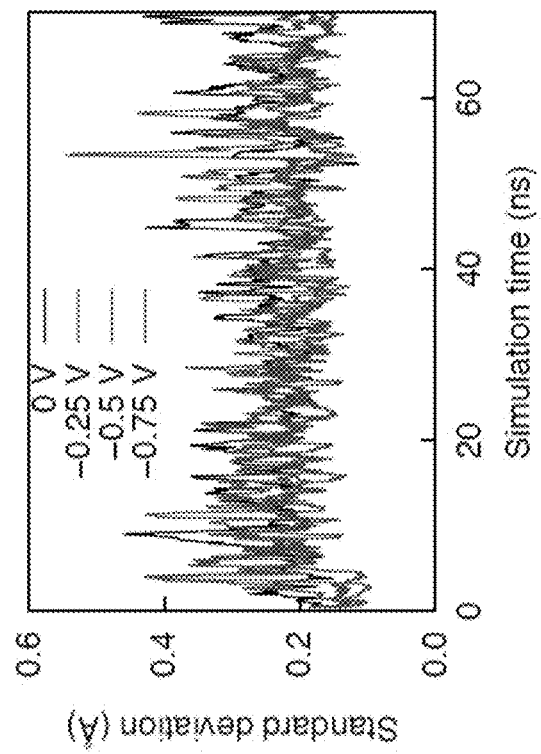
Figure 23C:
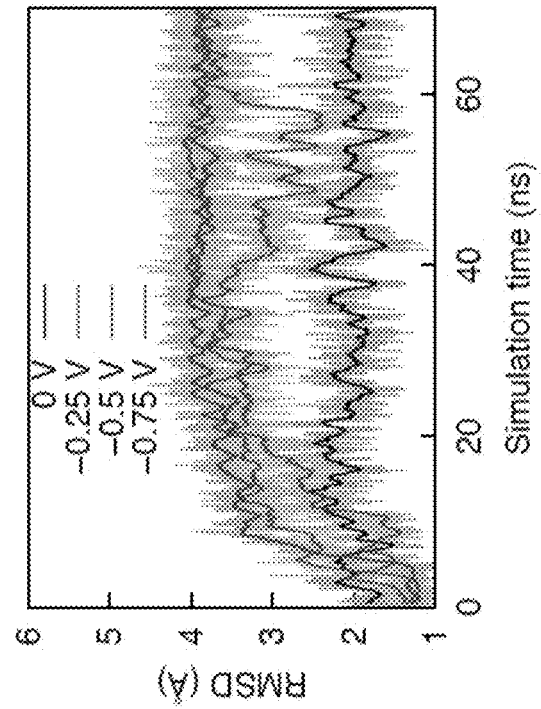

FIGS. 23A and 23C show the root mean square deviation (RMSD) profiles of all non-hydrogen atoms of the central portion of the dsDNA, namely nucleotides between the 6th and 17th base-pair of the 22 base-pairs, from the starting conformation under positive and negative electrode voltages, respectively. In the voltage-free case, the dsDNA RMSD fluctuates around an average value of 2.1 Å during the whole simulation (black curve in FIG. 23A or 23C), with a high moving standard deviation ranging from 0.2 to 0.5 Å (black curve in FIG. 23B or 23D). When a positive voltage $V_C=0.25$ V is applied to the electrode, the overall RMSD profile (red curve) fluctuates around a relatively larger average displacement of ~3.5 Å from the starting conformation of the DNA (FIG. 23A), with a moving standard deviation between 0.15 and 0.3 Å that is reduced compared to the voltage-free case (FIG. 23B). The conformational change is attributed to the lateral expansion of the dsDNA in the xy-cross-sectional plane of the cylindrical pore which is induced by the electrostatic attraction between the positive pore surface and the negatively charged backbone of dsDNA. As the positive voltage further increases to $V_C=0.5$ V, the dsDNA RMSD profile exhibits an enhanced conformational change from the starting DNA structure with an average displacement of ~4.7 Å (green curve). In parallel, the moving standard deviation of the RMSD profile at this voltage is significantly reduced compared to $V_C$ values at 0.25 and 0 V, indicating that the thermal fluctuations of dsDNA is greatly inhibited (see also middle panel in FIG. 22C). When the positive voltage is increased to 0.75 V (blue curve in FIG. 23A), the dsDNA exhibits comparable RMSD values to those at 0.5 V voltage, indicating that the lateral expansion of the dsDNA reaches a steady state. However, the decreased moving standard deviation observed at 0.75 V electrode voltage suggests that higher positive voltages achieve stronger stabilization (blue curve in FIG. 23B).

In sharp contrast to the positive electrode biases, no evident stabilization effect is observed when negative voltages are applied to the membrane, as indicated by the large fluctuations in RMSD profile for all negative voltages (FIGS. 23C and 23D). However, the RMSD values are also increased at these negative voltages from the voltage-free case, which is induced by the lateral shrinkage of dsDNA due to the electrostatic repulsion between the negatively charged pore surface and DNA backbone (see also right panel in FIG. 22C). In all cases for negative voltages, the moving standard deviation displays no significant dependence on voltage strength (FIG. 23D), further indicating that negative voltages cannot effectively stabilize the DNA.

A quick response to changes in electrode voltage is of significance in applications where real-time and precise manipulation of biological molecules is required. To assess the possibility, we simulated the response of a DNA molecule to a pulsed voltage of 0.5 V, namely a voltage turned on and off repeatedly every 30 ns, as depicted in FIG. 24A. FIGS. 24B and 24C show the moving average and standard deviation of the RMSD of a dsDNA molecule from the initial configuration, respectively. When the voltage is turned on, the lower fluctuations in RMSD profile (FIG. 24B), validated by a lower standard deviation (FIG. 24C), indicate the stabilization of DNA in the nanopore. When the voltage is turned off, the DNA reverts, as expected, to a configuration with lower RMSDs, but larger fluctuations. When the positive voltage is turned on again, the fluctuations are again suppressed. In addition, it is worth mentioning that the stabilization is achieved within 1 ns after turning on the voltage, indicating the ability of a real-time and precise manipulation to DNA motion.

Figure 25B:
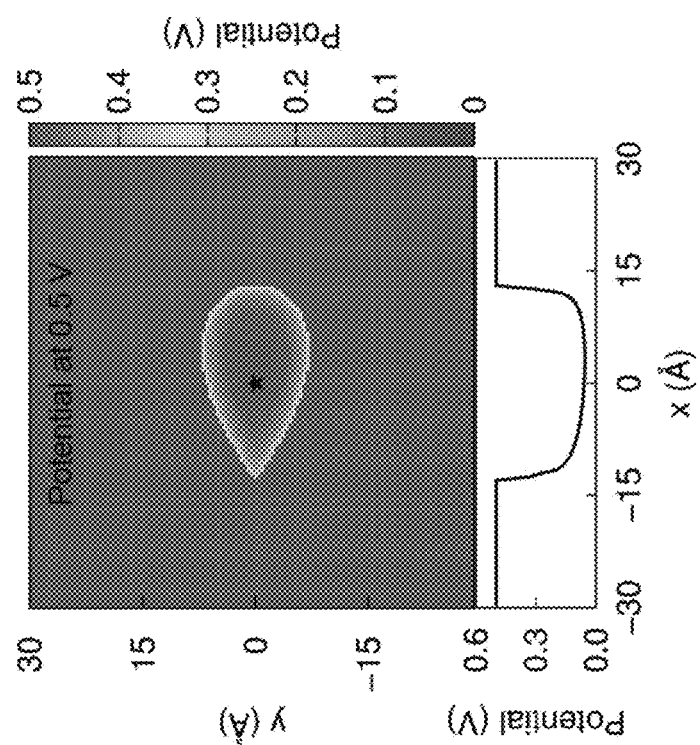
FIGS. 25A, 25B, 25C and 25D depict customized control of DNA alignment through pore geometry shaping. (a) Geometry of the cross-section of the teardrop-shape nanopore simulated in this study. (b,c) Electrostatic potential (b) and magnitude of electric field (c) of the teardrop-shape nanopore at 0.5 V electrode voltage, in the xy-cross-section plane (top panel) and along a line across the nanopore center (bottom panel). (d) Scatter diagram showing center of mass positions of dsDNA in MD trajectories at electrode voltages of 0, 0.5 and −0.5 V. The coordinate origin is depicted as a star.
Figure 25A:
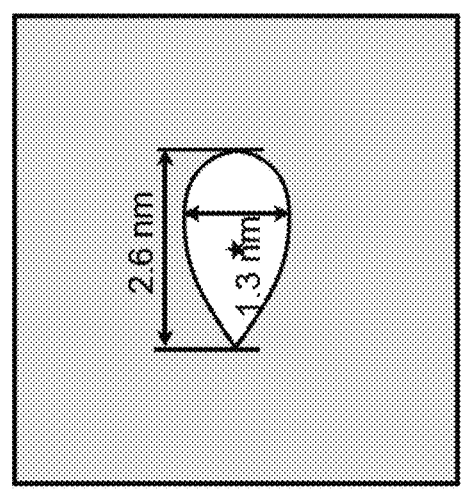
Figure 25D:
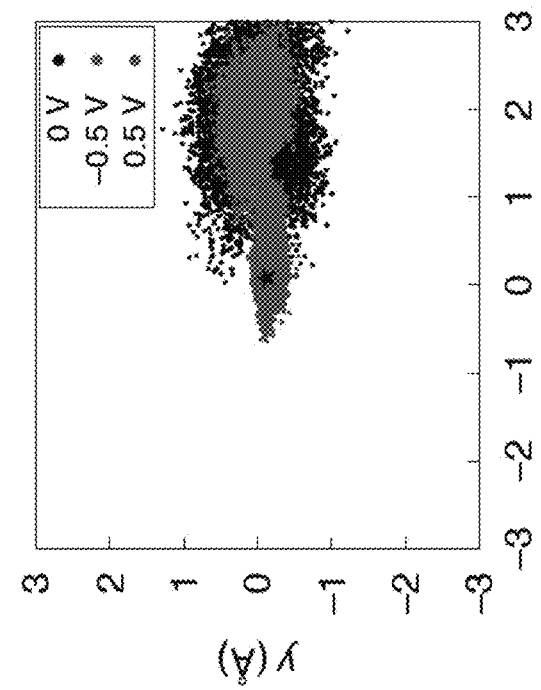
Figure 25C:
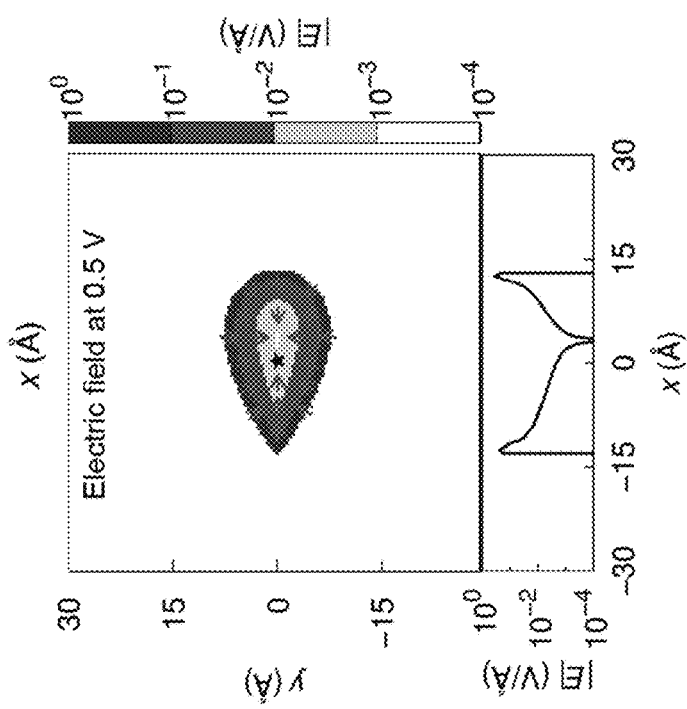

In all above simulations, a circular pore was considered to confine DNA and generate the potential landscape for DNA stabilization. As expected, the dwelling area of the DNA CM positions inside such a symmetric pore is approximately circular (FIGS. 22A-22B). In realistic experiments, however, a fabricated pore can hardly be a perfect cylinder. In this context, one may wonder if a pore with a lower spatial symmetry can achieve a customized control on the DNA conformation. For this purpose, we consider a teardrop-shape pore to assess the influence of pore geometry on the DNA behavior, as shown in FIG. 25A. In FIGS. 25B-25C, we show the electrostatic potential and electric field for a teardrop-shape nanopore, respectively, at a positive electrode voltage of 0.5 V. The potential and electric field are no longer symmetric in the x-direction, but rather, decay more slowly away from the sharp end (left) than from the smooth end (right). When the obtained potential is applied to the DNA molecule, a strong DNA localization occurs again, as seen from the concentrated distribution of CM positions (green dots in FIG. 25D) compared to the voltage-free case (black dots in FIG. 25D). In addition, it is worth noting that the DNA moves slightly leftward to approach the sharp end under the positive voltage, mainly due to the relatively higher magnitude and slower decay of the potential/electric field on the left side of the pore. At a negative voltage of $V_C=-0.5$ V, the inhibition of DNA fluctuation and the leftward movement of DNA center are insignificant compared to the positive voltage case. The demonstrated controllable alignment of DNA inside shaped nanopores is of critical importance in DNA sensing applications where a high-sensitivity DNA sensing emerges only when DNA base is aligned along a specific direction, for example, perpendicular to the flo wing direction of the transverse current.[24]

In summary, we investigate the ability of a biased nanopore to quench DNA conformational fluctuations by combining self-consistent electrostatic potential calculations and molecular dynamics simulations. We found that DNA molecules are stabilized by imposing positive voltages higher than 0.5 V on the nanopore electrodes. The reduction of DNA fluctuations is attributed to an electrostatic attraction between the negatively charged DNA backbone and the positive pore surface. No evident conformational response of DNA occurs at negative electrode voltages. The use of a teardrop-shape pore yields also a teardrop-shape distribution of DNA CM positions, which shrinks significantly and shifts slightly toward the sharp end of the pore under positive electrode voltages. The present findings open a simple and efficient route to control motions of biological molecules inside nanopores to improve the signal-signal-to-noise ratio, which is highly desirable for nanopore sensing applications.

Methods

Our methodological approach outlined below includes calculation of electrostatic potential arising from various voltage biases at the electrode layer and subsequent classic MD simulations on DNA fluctuations under the obtained potentials, which were applied to a DNA molecule via the grid force module of NAMD2.[25]

Electrostatic Potential Calculations

The electrostatic potential $\varphi$ inside a nanopore filled up with electrolytic solution was obtained by solving the Poisson equation in three dimensions $$\nabla \cdot [\varepsilon(r)\nabla\phi(r)] = -\varepsilon[c_{K^+}(r) - c_{Cl^-}(r)], \quad (1)$$

where $\varepsilon(r)$ is the position-dependent dielectric constant, i.e., $\varepsilon=78$ in water and $\varepsilon\to\infty$ at the metal electrode. The right-hand-side charge term includes ions in the solution ($K^+$ and $Cl^-$), which are described assuming a Boltzmann equilibrium, namely through[10]

$$c_{K^+}(r) = c_0\exp\left[-\frac{e\phi(r)}{k_B T}\right], \quad c_{Cl^-}(r) = c_0\exp\left[\frac{e\phi(r)}{k_B T}\right], \quad (2)$$

where $c_{K^+}$ and $c_{Cl^-}$ are the local ion concentrations $K^+$ and $Cl^-$, and $c_0$ is the molar concentration of the solution, taken to be 0.3 M.

The system was discretized within a Cartesian box onto a non-uniform, rectilnear grid. Neumann boundary conditions were imposed on the sides of the box.

$$\left.\frac{\partial\phi}{\partial x}\right|_{x=\pm L_x/2} = \left.\frac{\partial\phi}{\partial y}\right|_{y=\pm L_y/2} = 0, \quad (3)$$

while the top and bottom of the box were subjected to Dirichlet boundary conditions, $$\phi(z=\pm L_Z/2)=\phi_\pm. \quad (4)$$

$$\varphi(z=\pm L_Z/2)=\varphi_\pm. \quad (4)$$

All electrode points were also subjected to Dirichlet conditions, with the potential $\varphi$ set to the chosen biased voltage.

Eqn. 1 can be solved self-consistently using a number of methods. In the present study, we adopted a Newton-Multigrid[26-28] method that discretizes the system onto a 129×129×129 point uniform grid. Starting from the finest grid, Jacobi relaxation was performed to obtain an initial guess for the solution $\varphi$. Then, the solution was interpolated and relaxed on subsequently coarser grids to smooth out high-frequency errors Finally, the error to the solution was relaxed and interpolated on finer grids until the original, fine-grid solution was corrected. Once the solution $\varphi$ was obtained, it was re-inserted back into the Poisson equation, and this process was repeated until the desired convergence was reached. A full description of the exact procedure followed has been provided earlier.[26-28]

Molecular Dynamics Simulations

A dsDNA helix containing 22 base-pairs of dA-dT was constructed by the X3DNA program.[29] For the sake of simplicity, we placed the DNA strand, subjected to mathematical boundaries representing the confinement of DNA in a cylindrical or tear-drop shape nanopore, in a water box. Inclusion of a real material as the motion-control layer, such as copper or gold, would alter the stabilization behavior demonstrated here; in some cases, the stabilization effect may be promoted due to the strong intrinsic interaction between the pore and DNA molecule.

$K^+$ and $Cl^-$ ions were randomly added to the water box to make the system charge neutral and achieve an ion concentration at 0.3 M. All simulations were carried out with NAMD 2.9,[25] and visualized and analyzed with VMD.[30] A Langevin thermostat was adopted to maintain constant temperature at 300 K. Periodic boundary conditions were imposed to all directions and, thereby, an infinitely long nanopore was obtained in the z-direction. DNA was described with the CHARMM27[31] force field and water was modelled by the T1P3P[32] water model. A time step of 2 fs was used in all simulations. The particle-mesh-Ewald method[33] was employed to treat the long-range electrostatic interactions. van der Waals energies were calculated using a cut-off of 12 Å. After a 5000-step energy minimization, the system was initially equilibrated for 2 ns as an NPT ensemble, in which the Langevin piston method[34] was used to control the pressure at 1 atm. The calculated potential through Eqn. 1 was then applied to the DNA only in the MD simulations, as the redistribution of ions and water by the potential has already been taken into account in the Poisson-Boltzmann solution of Eqn. 1. At a given voltage, each simulation was run for 70 ns as an NVT ensemble for data analysis.

The aforementioned embodiments of the subject disclosure can be adapted to detect structural components of a biomolecule. For example, nanopores can be fabricated on solid-state membranes such as silica or graphene (known as solid state nanopores) or are naturally found in nature where pores are formed in biological membranes (known as bacterial toxin alpha-hemolysin). These pores can be used as sensors to probe small biomolecules such as DNA and proteins. The main attraction of these nanopores is that they act like sensors that can probe structures along the cross section providing an "electric response" for each region of the biomolecule inside the pore.

It will be appreciated that the nanopores referred to in the foregoing embodiments can be constructed with different techniques. For example, nanopores can be constructed with electron beam lithography. Electron beam lithography can be used to construct a circular-shaped nanopore (or other symmetric-shaped nanopore) or a non-circular-shaped nanopore (e.g., an oval-shaped nanopore, a teardrop-shaped nanopore, or an asymmetric-shaped nanopore). Other techniques can be used for constructing nanopores, which are contemplated by the subject disclosure.

Most experiments with nanopores are carried out in a solution of water with potassium and chlorine ions present. These ions are responsible for the current response to the biomolecule going through the pore (also known as translocating). A typical experimental structure of a nanopore experiment used to probe DNA (to potentially identify the different bases) is shown in FIG. 26.

Figure 26:
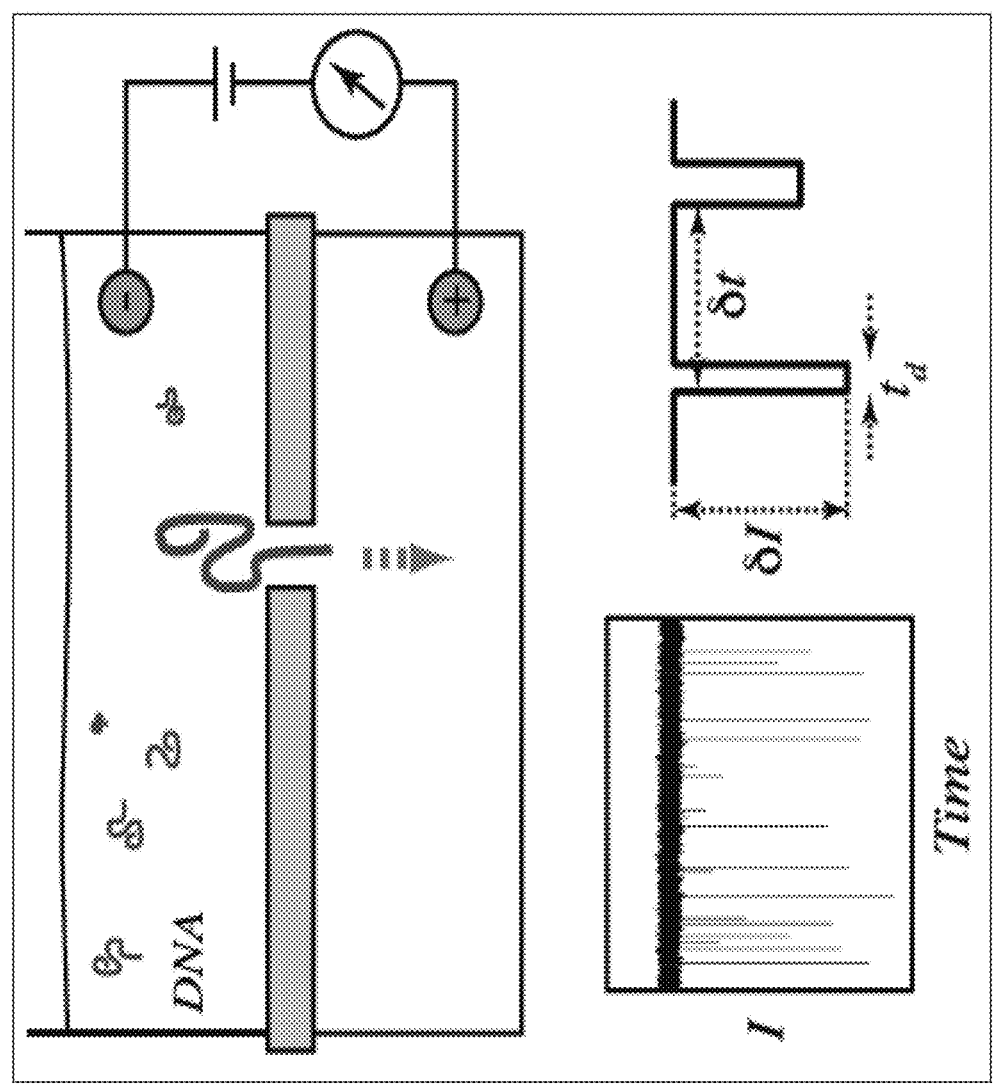
FIG. 26 depicts a system for measuring ionic currents for a pore that conducts materials such as DNA. The system is also adapted to measure blocking currents that enable the system to identify a structural part of, for example, a biomolecule.

FIG. 26 illustrates schematically a system for measuring characteristic ionic currents for a pore that conducts DNA (proteins or other substances). In the illustration of FIG. 26, a single nanopore separates two compartments filled with salt buffer and connected to Ag—AgCl electrodes. When a constant voltage is applied between these electrodes, the ions in the solution start moving towards opposite terminals (positively charged potassium ions move towards the negative electrode and vice versa). This movement of ions induces a steady-state ionic current through the pore, which is measured by an amplifier. Note that the current here, caused due to the potassium and chlorine ions moving towards the terminals through the nanopore constitutes the "ionic" current. Since, most of the biomolecules that can be probed are charged electrically, the application of the constant bias can also drive the molecule through the pore. Adding DNA (for example) to the negatively biased compartment is observed to cause transient reductions of the ionic current, like the one shown in FIG. 26. These reductions are caused because each of the individual bases of the DNA strand block the nanopore as they translocate through hindering the flow of ions in the nanopore. This reduced conductance is associated with the translocation of DNA through the pore, which partially blocks the ionic current. Resolving the duration and magnitude of each dip can be used to analyze and identify the structure of part of the biomolecule inside the pore.

Using a similar set-up, the blockage currents can be measured for a single-stranded RNA and DNA electrically driven through the transmembrane pore of an alpha-hemolysin channel, which can be suspended in a lipid bilayer. Analysis of blockage currents enables discriminating between different sequences of RNA and DNA polymers. A single nucleotide resolution has been demonstrated for DNA hairpins enabling the use of a nanopore sensor capable of reading the nucleotide sequence directly from a DNA or RNA strand. Recent advances in semiconductor nanotechnology allow one to manufacture pores with nanometer-size diameters using highly focused ion and electron beams. These nanopores have also been used as Coulter counter devices for detecting single DNA molecules, resolving their length and diameter.

FIG. 27 depicts an exemplary diagrammatic representation of a machine in the form of a computer system 2700 within which a set of instructions, when executed, may cause the machine to perform any one or more of the methods discussed above. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 2700 may include a processor 2702 (e.g., a central processing unit (CPU), a graphics processing unit (GPU, or both), a main memory 2704 and a static memory 2706, which communicate with each other via a bus 2708. The computer system 2700 may further include a video display unit 2710 (e.g., a liquid crystal display (LCD), a flat panel, or a solid state display. The computer system 2700 may include an input device 2712 (e.g., a keyboard), a cursor control device 2714 (e.g., a mouse), a disk drive unit 2716, a signal generation device 2718 (e.g., a speaker or remote control) and a network interface device 2720 communicatively coupled to a network 2726.

The disk drive unit 2716 may include a tangible computer-readable storage medium 2722 on which is stored one or more sets of instructions (e.g., software 2724) embodying any one or more of the methods or functions described herein, including those methods illustrated above. The instructions 2724 may also reside, completely or at least partially, within the main memory 2704, the static memory 2706, and/or within the processor 2702 during execution thereof by the computer system 2700. The main memory 2704 and the processor 2702 also may constitute tangible computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the operations or methods described herein are intended for operation as software programs or instructions running on or executed by a computer processor or other computing device, and which may include other forms of instructions manifested as a state machine implemented with logic components in an application specific integrated circuit or field programmable gate array. Furthermore, software implementations (e.g., software programs, instructions, etc.) including, but not limited to, distributed processing or component/object distributed processing, parallel processing, or virtual machine processing can also be constructed to implement the methods described herein. It is further noted that a computing device such as a processor, a controller, a state machine or other suitable device for executing instructions to perform operations or methods may perform such operations directly or indirectly by way of one or more intermediate devices directed by the computing device.

While the tangible computer-readable storage medium 622 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA) are contemplated for use by computer system 2700.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement which achieves the same or similar purpose may be substituted for the embodiments described or shown by the subject disclosure. The subject disclosure is intended to cover any and all adaptations or variations of various embodiments. Combinations of the above embodiments, and other embodiments not specifically described herein, can be used in the subject disclosure. For instance, one or more features from one or more embodiments can be combined with one or more features of one or more other embodiments. In one or more embodiments, features that are positively recited can also be negatively recited and excluded from the embodiment with or without replacement by another structural and/or functional feature. The steps or functions described with respect to the embodiments of the subject disclosure can be performed in any order. The steps or functions described with respect to the embodiments of the subject disclosure can be performed alone or in combination with other steps or functions of the subject disclosure, as well as from other embodiments or from other steps that have not been described in the subject disclosure. Further, more than or less than all of the features described with respect to an embodiment can also be utilized.

Less than all of the steps or functions described with respect to the exemplary processes or methods can also be performed in one or more of the exemplary embodiments. Further, the use of numerical terms to describe a device, component, step or function, such as first, second, third, and so forth, is not intended to describe an order or function unless expressly stated so. The use of the terms first, second, third and so forth, is generally to distinguish between devices, components, steps or functions unless expressly stated otherwise. Additionally, one or more devices or components described with respect to the exemplary embodiments can facilitate one or more functions, where the facilitating (e.g., facilitating access or facilitating establishing a connection) can include less than every step needed to perform the function or can include all of the steps needed to perform the function.

In one or more embodiments, a processor (which can include a controller or circuit) has been described that performs various functions. It should be understood that the processor can be multiple processors, which can include distributed processors or parallel processors in a single machine or multiple machines. The processor can be used in supporting a virtual processing environment. The virtual processing environment may support one or more virtual machines representing computers, servers, or other computing devices. In such virtual machines, components such as microprocessors and storage devices may be virtualized or logically represented. The processor can include a state machine, application specific integrated circuit, and/or programmable gate array including a Field PGA. In one or more embodiments, when a processor executes instructions to perform "operations", this can include the processor performing the operations directly and/or facilitating, directing, or cooperating with another device or component to perform the operations.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method, comprising:
    coupling a first end of a material to a first electrode;
    coupling a second end of the material to a second electrode;
    coupling a gate to the material;
    forming in the material a first through-hole having a first non-circular structure;
    forming in the gate a second through-hole;
    applying a first voltage potential to the first electrode and the second electrode coupled to the material;
    applying a second voltage potential to the gate to adjust a charge concentration of the material;
    measuring, via a sensor that includes a voltmeter, a change in electrical properties of the material responsive to a plurality of structural units of a target material traversing the first through-hole of the material, wherein the first non-circular structure of the first through-hole causes the plurality of structural units of the target material to be at least in part misaligned with a direction of a flow of current induced in the material by the first voltage potential; and
    counting the plurality of structural units of the target material according to the change in electrical properties of the material measured when each of the plurality of structural units of the target material traverses the first through-hole.

2. The method of claim 1, further comprising disposing a first insulator on a top surface of the material, and disposing a second insulator on a bottom surface of the material, wherein the first insulator comprises a third through-hole, and wherein the second insulator comprises a fourth through-hole.

3. The method of claim 2, wherein the first insulator and the second insulator comprise an oxide material or a dielectric material, and wherein the oxide material comprises an aluminum oxide, a hafnium oxide, a silicon dioxide, or any combinations thereof, and wherein the dielectric material comprises silicon nitride.

4. The method of claim 1, wherein the first through-hole or the second through-hole is constructed utilizing electron beam lithography.

5. The method of claim 1, wherein the material comprises a graphene.

6. The method of claim 1, wherein the material comprises a quantum point contact.

7. The method of claim 1, wherein the material comprises a molybdenum disulfide, a transition metal chalcogenides, or any combinations thereof.

8. The method of claim 1, wherein a state of the electrical properties of the material is controlled by the first voltage potential, the second voltage potential, the first non-circular structure of the first through-hole, a size of the first through-hole, or any combinations thereof, and wherein changes in the state of the electrical properties of the material are caused by each of the plurality of structural units of the target material traversing the first through-hole of the material.

9. The method of claim 1, wherein the second through-hole comprises a second non-circular structure that is substantially aligned with the first non-circular structure of the first through-hole.

10. The method of claim 1, wherein the first non-circular structure of the first through-hole comprises an elongated structure that extends in a direction that is at least in part misaligned with the direction of the flow of current induced in the material by the first voltage potential.

11. The method of claim 1, wherein the target material comprises a biomolecule.

12. The method of claim 11, wherein a structural unit of the plurality of structural units of the target material comprises a nucleotide, a protein, a biomolecule complex, or a combination thereof.

13. The method of claim 1, wherein the change in electric properties of the material is increased by the first non-circular structure of the first through-hole causing the plurality of structural units of the target material to be misaligned with the direction of the flow of current induced in the material by the first voltage potential.

14. The method of claim 1, further comprising:
    coupling to the material at least one control layer having a third through-hole aligned with the first through-hole and the second through-hole; and
    applying at least a third voltage potential to the at least one control layer to control movement of the plurality of structural units of the target material through the first through-hole, the second through-hole, and the third through-hole.

15. The method of claim 1, wherein the material comprises one or more atomic layers with two or less degrees of freedom of motion of charges in the material.

16. The method of claim 1, further comprising:
    constructing a control layer with a third through-hole aligned at least in part with the first through-hole of the material for controlling a translocation of the target material through the first through-hole of the material.

17. An apparatus, comprising:
a material; and
a gate coupled to the material for controlling a charge concentration of the material,
wherein the material comprises a first through-hole including an irregular structure, and a first port and a second port for conduction of charges in the material,
wherein the gate comprises a second through-hole that is at least partially aligned with the first through-hole,
wherein a first voltage potential applied to the first port and the second port, and a second voltage potential applied to the gate adjusts a charge concentration of the material,
wherein a sensor obtains a measurement of a change in electrical properties of the material caused by a structural unit of a target material traversing the first through-hole of the material and provides the measurement to a controller to count a plurality of structural units of the target material, wherein the structural unit is included in the plurality of structural units,
wherein the irregular structure misaligns the structural unit of the target material with a direction of a flow of current induced in the material by the first voltage potential, and
wherein the sensor includes a voltmeter.

18. The apparatus of claim 17, wherein the structural unit of the target material comprises a nucleotide or a protein.

19. An apparatus, comprising:
a material including a first through-hole;
a gate coupled to the material for controlling a charge concentration of the material, wherein the gate comprises a second through-hole;
a sensor that includes a voltmeter; and
a controller coupled to the material, the gate and the sensor, wherein the controller performs operations comprising:
applying a first voltage potential to the material to induce a flow of current in the material;
applying a second voltage potential to the gate to adjust the charge concentration of the material; and
receiving sensing data from the sensor responsive to a change in electrical properties of the material caused by a plurality of structural portions of a target traversing the first through-hole of the material, wherein the first through-hole causes the plurality of structural portions of the target to be misaligned with a direction of the flow of current in the material.

20. The apparatus of claim 19, wherein misalignment of the plurality of structural portions of the target with the direction of the flow of current in the material increases the change in electrical properties of the material as each of the plurality of structural portions of the target traverses the first through-hole.

* * * * *

UNITED STATES PATENT AND TRADEMARK OFFICE
CERTIFICATE OF CORRECTION

PATENT NO. : 10,345,289 B2
APPLICATION NO. : 15/063095
DATED : July 9, 2019
INVENTOR(S) : Jean-Pierre Leburton It is certified that error appears in the above-identified patent and that said Letters Patent is hereby corrected as shown below:

In the Specification

Column 6, Line 18 please delete "196949'76) investigated the influence of single-stranded" and insert --(1969-1976) investigated the influence of single-stranded--

Signed and Sealed this
Third Day of September, 2019

Andrei Iancu
*Director of the United States Patent and Trademark Office*